US011334965B2

(12) United States Patent
Ben-Haim et al.

(10) Patent No.: US 11,334,965 B2
(45) Date of Patent: May 17, 2022

(54) MAPPING BINNED MEDICAL DATA

(71) Applicant: Navix International Limited, Tortola (VG)

(72) Inventors: Shlomo Ben-Haim, Milan (IT); Eli Dichterman, Haifa (IL)

(73) Assignee: Navix International Limited, Road Town (VG)

( * ) Notice: Subject to any disclaimer, the term of this patent is extended or adjusted under 35 U.S.C. 154(b) by 0 days.

(21) Appl. No.: 16/971,336

(22) PCT Filed: Feb. 21, 2019

(86) PCT No.: PCT/IB2019/051423
§ 371 (c)(1),
(2) Date: Aug. 20, 2020

(87) PCT Pub. No.: WO2019/162874
PCT Pub. Date: Aug. 29, 2019

(65) Prior Publication Data
US 2021/0090215 A1  Mar. 25, 2021

Related U.S. Application Data

(60) Provisional application No. 62/633,119, filed on Feb. 21, 2018.

(51) Int. Cl.
*G06K 9/00* (2022.01)
*G06T 3/40* (2006.01)
(Continued)

(52) U.S. Cl.
CPC .......... *G06T 3/4038* (2013.01); *G06T 7/0012* (2013.01); *G06T 7/38* (2017.01);
(Continued)

(58) Field of Classification Search
None
See application file for complete search history.

(56) References Cited

U.S. PATENT DOCUMENTS

| 10,605,880 B2 * | 3/2020 | Bi ................... G01R 33/56509 |
| 2016/0367212 A1 | 12/2016 | Tang et al. |
| 2020/0405176 A1 * | 12/2020 | Nielsen ................ G01R 33/482 |

FOREIGN PATENT DOCUMENTS

| WO | WO 2005/093662 | 10/2005 |
| WO | WO 2007/015100 | 2/2007 |

(Continued)

OTHER PUBLICATIONS

Aitken et al., "100% efficient three-dimensional coronary MR angiography with two-dimensional beat-to-beat translational and bin-to-bin affine motion correction" (Year: 2015).*

(Continued)

*Primary Examiner* — Soo Jin Park

(57) ABSTRACT

A method of generating a combined image of a body part from a sequence of partially overlapping source images of the body part, each of the partially overlapping source images showing the body part at one of a plurality of different times, the source images being ordered in the sequence according to the different times, the method including defining a temporally coherent sequence of transformations, for registering the partially overlapping source images in the sequence with each other, registering the source images to each other using the defined temporally coherent sequence of transformations, to obtain co-registered images, and combining at least some of the co-registered images into a combined image. Related apparatus and methods are also described.

23 Claims, 22 Drawing Sheets

(51) Int. Cl.
  *G06T 7/55* (2017.01)
  *G06T 7/38* (2017.01)
  *G06T 7/00* (2017.01)
(52) U.S. Cl.
  CPC ...... *G06T 7/55* (2017.01); *G06T 2207/10016* (2013.01); *G06T 2207/10028* (2013.01)

(56) References Cited

FOREIGN PATENT DOCUMENTS

| WO | WO 2007/015199 | 2/2007 |
|---|---|---|
| WO | WO 2008/004171 | 1/2008 |
| WO | WO 2016/181316 | 11/2016 |
| WO | WO 2016/181320 | 11/2016 |
| WO | WO 2018/130974 | 7/2018 |
| WO | WO 2018/207128 | 11/2018 |
| WO | WO 2019/162874 | 8/2019 |

OTHER PUBLICATIONS

International Preliminary Report on Patentability dated Sep. 3, 2020 From the International Bureau of WIPO Re. Application No. PCT/IB2019/051423. (13 Pages).
International Search Report and the Written Opinion dated Jun. 27, 2019 From the International Searching Authority Re. Application No. PCT/IB2019/051423. (19 Pages).
Daluwatte et al. "A Robust Detection Algorithm to Identify Breathing Peaks in Respiration Signals From Spontaneously Breathing Subjects", Computing in Cardiology Conference, CinC 2015, Nice, France, Sep. 6-9, 2015, 42: 297-300, Sep. 6, 2015.
Habert et al. "Registration of Multiple Temporally Related Point Sets Using A Novel Variant of the Coherent Point Drift Algorithm: Application to Coronary Tree Matching", SPIE Medical Imaging 2013, Lake Bueno Vista, Orlando Area, Florida, USA, Mar. 13, 2013, Medical Imaging: Image Processing, Proceedings of the SPIE, 8669: 86690M-1-86690M-11, Mar. 13, 2013.
Myronenko et al. "Point Set Registration: Coherent Point Drift", arXiv Preprint arXiv:0905.2635v1, p. 1-14, May 15, 2009.
Myronenko et al. "Point Set Registration: Coherent Point Drift", IEEE Transaction on Pattern Analysis and Machine Intelligence, 32(12): 2262-2275, Published Online Feb. 25, 2010.
Wierzbicki et al. "Valdiation of Dynamic Heart Models Obtained Using Non-Linear Registration for Virtual Reality Training, Planning, and Guidance of Minimally Invasive Cardiac Surgeries", Medical Image Analysis, XP004533595, 8(3): 387-401, Available Online Jul. 17, 2004.
Wilson et al. "4D Shape Registration for Dynamic Electrophysiological Cardiac Mapping", MICCAI 2006, Proceedings of the 9th International Conference on Medical Image Computing and Computer-Assisted Intervention, Copenhagen, Denmark, Oct. 1-6, 2006, XP055474225, Part II, LNCS 4191: 520-527, Oct. 1, 2006.
Wilson et al. "Mapping of Cardiac Electrophysiology Onto A Dynamic Patient-Specific Heart Model", IEEE Transactions on Medical Imaging, XP055557455, 28(12): 1870-1880, Published Online May 5, 2009.
Zhou et al. "A Real-Time Atrial Fibrillation Detection Algorithm Based on the Instantaneous State of Heart Rate", Plos One, 10(9): e0136544-1-e0136544-16, Published Online Sep. 16, 2015.

\* cited by examiner

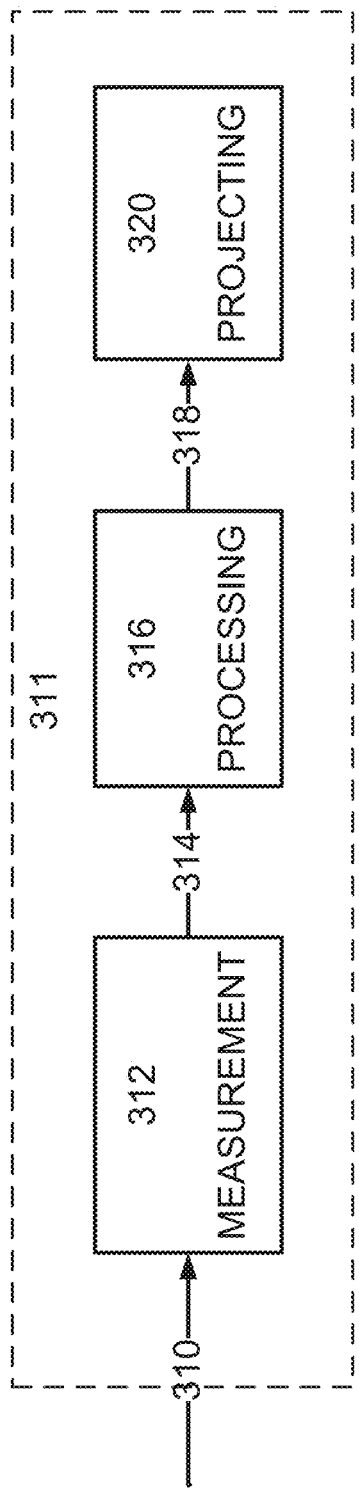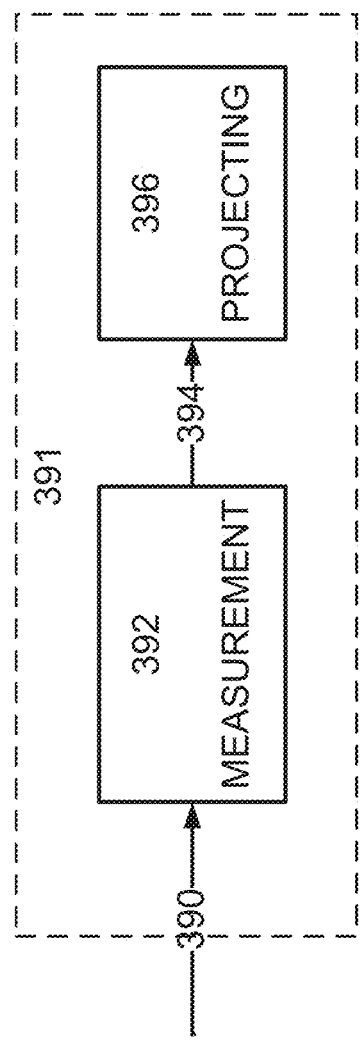

MAPPING BINNED MEDICAL DATA

RELATED APPLICATIONS

This application is a National Phase of PCT Patent Application No. PCT/IB2019/051423 having International filing date of Feb. 21, 2019, which claims the benefit of priority under 35 USC § 119(e) of U.S. Provisional Patent Application No. 62/633,119 filed on Feb. 21, 2018. The contents of the above applications are all incorporated by reference as if fully set forth herein in their entirety.

FIELD AND BACKGROUND OF THE INVENTION

The present invention, in some embodiments thereof, relates to transforming medical data captured under different circumstances to a common framework, and, more particularly, but not exclusively, to transforming values of data points obtained from an intra-body probe to a common coordinate system in order to use the data points to image and/or model anatomical structure.

Some embodiments of the present invention include modelling a structure of a body organ or portion thereof based on data received from a probe when there is mutual movement between the probe and the body organ portion to be modelled.

Some embodiments of the present invention include improvement of modelling a structure of a body organ or portion thereof based on using data received from a probe when there is mutual movement between the probe and the body organ portion to be modelled.

Embodiments of the invention may be practiced in, for example, modelling and/or imaging of cardiac structure.

Background art includes:

an article titled "A robust detection algorithm to identify breathing peaks in respiration signals from spontaneously breathing subjects", published in 2015 Computing in Cardiology Conference, DOI: 10.1109/CIC.2015.7408645;

an article titled "Registration of Multiple Temporally Related Point Sets Using a Novel Variant of the Coherent Point Drift Algorithm: Application to Coronary Tree Matching" Conference Paper in Proceedings of SPIE—The International Society for Optical Engineering, 8669: 86690M•March 2013 DOI: 10.1117/12.2004764;

an article titled "A real-time atrial fibrillation detection algorithm based on the instantaneous state of heart rate", published in PLoS ONE 10(9) e0136544, an article titled "Point Set Registration: Coherent Point Drift", published on 15 May 2009 on the world-wide-web, in arxiv(dot)org/abs/0905.2635', and an article titled "Registration of multiple temporally related point sets using a novel variant of the coherent point drift algorithm: application to coronary tree matching" published in Proc. of SPIE vol. 8669.

The disclosures of all references mentioned above and throughout the present specification, are hereby incorporated herein by reference.

SUMMARY OF THE INVENTION

The present invention, in some embodiments thereof, relates to transforming medical data captured under different circumstances to use a common framework, and more particularly, but not exclusively, to transforming electrical readings obtained from an intra-body probe to use a common framework coordinate system in order to use the electrical readings to map and/or image and/or model anatomical structure.

Some embodiments of the present invention include modelling a structure of a body organ or portion thereof based on data received from a probe when there is mutual movement between the probe and the body organ portion to be modelled.

Some embodiments of the present invention include improvement of modelling a structure of a body organ or portion thereof based on using data received from a probe when there is mutual movement between the probe and the body organ portion to be modelled.

According to an aspect of some embodiments of the present invention there is provided a method for imaging of a body organ undergoing periodic changes in at least one dimension, the method including measuring at least two partial data sets of the body organ, determining at least one corresponding data point in each one of the at least two partial data sets describing the at least one dimension of the body organ which is undergoing repetitive changes, projecting at least one of the two partial data sets into a data set having a common framework, based on the corresponding data.

According to some embodiments of the invention, the projecting at least one of the two partial data sets into a data set having a common framework includes projecting at least one of the two partial data sets into another one of the two partial data sets, based on the corresponding data.

According to some embodiments of the invention, the measuring at least two partial data sets of the body organ is performed during different time periods.

According to some embodiments of the invention, the measuring at least two partial data sets of the body organ is performed during partially-overlapping time periods.

According to some embodiments of the invention, the measuring at least two partial data sets of the body organ is performed at adjacent or partially overlapping locations of the body organ.

According to an aspect of some embodiments of the present invention there is provided a method for imaging an anatomical structure based on sensor readings, the method including receiving sensor readings from a plurality of sensors, converting the sensor readings to data points, classifying each one of the data points to as belonging to one of a plurality of data bins, identifying a set of corresponding data points in at least a first data bin and a second data bin of the plurality of data bins, calculating a transformation from the corresponding data points in the second data bin to the corresponding data points in the first data bin, projecting data points in the second data bin to data points in the first data bin using the transformation, producing a combined set of data points including the data points of the first data bin and the projected data points from the second data bin, and imaging the combined set of data points.

According to some embodiments of the invention, the sensors include electrodes and the sensor readings include electrical readings.

According to some embodiments of the invention, converting the electrical readings to data points includes converting from values of electrical readings to location values in space.

According to some embodiments of the invention, the anatomical structure includes a heart chamber.

According to some embodiments of the invention, receiving electrical readings includes receiving measurement from a plurality of electrodes on an intra-body probe.

According to some embodiments of the invention, receiving electrical reading includes receiving measurement from a plurality of electrodes on an intra-body probe and from at least one body surface electrode.

According to some embodiments of the invention, classifying the data points to a plurality of data bins produces a sparse data set in at least one of the data bins.

According to some embodiments of the invention, the classifying the data points to a plurality of data bins produces a sparse data set in each one of the data bins.

According to some embodiments of the invention, a number of data points in the combined set of data points is greater than a number of data points in the first data bin.

According to some embodiments of the invention, the receiving, the classifying, the identifying, the calculating, the projecting and the producing a combined set of data points is performed for more than two data bins.

According to some embodiments of the invention, the converting is from electrical readings to dielectric values.

According to some embodiments of the invention, receiving sensor readings further includes receiving physical measurements selected from a group consisting of electric potential, electric current, electric permittivity, time, location, pressure, blood pressure, nasal air flow, blood chemical concentration, and temperature.

According to some embodiments of the invention, the data points include a dimension selected from a group consisting of time, location in space, pressure, temperature, phase in cardiac cycle, phase in breathing cycle, amplitude of breathing motion, category of cardiac rhythm, phase in cycle of adjacent heart chamber, and category of breathing type.

According to some embodiments of the invention, the second data bin belongs to a same dimension as the first data bin.

According to some embodiments of the invention, the second data bin belongs to a different dimension than the first data bin.

According to some embodiments of the invention, the transformation includes a transformation from a data bin including data points of a chaotic cardiac rhythm to a data bin including data points of a non-chaotic cardiac rhythm.

According to some embodiments of the invention, the classifying each one of the data points to as belonging to one of a plurality of data bins includes classifying at least some of the data points as belonging to at least one atrial fibrillation (AF) data bin.

According to some embodiments of the invention, the classifying each one of the data points to as belonging to one of a plurality of data bins includes classifying at least some of the data points as belonging to at least one arrhythmia data bin.

According to some embodiments of the invention, the transformation includes a transformation from a data bin including data points of a cardiac rhythm classified as atrial fibrillation (AF) to a data bin including data points of a non-AF cardiac rhythm.

According to some embodiments of the invention, the transformation includes a plurality of transformations selected from a group consisting of (a) a transformation from a data bin including data points of a first cardiac rhythm category to a data bin including data points of a second cardiac rhythm category, (b) a transformation from a data bin including data points of a first breathing rhythm category to a data bin including data points of a second breathing rhythm category, and (c) a transformation from a data bin including data points of a first cardiac rhythm category to a data bin including data points of a second cardiac rhythm category.

According to some embodiments of the invention, the transformation includes a sequence of transformations starting with transformation (a), then (b), then (c).

According to some embodiments of the invention, the combined set of data points includes less dimensions than a number of dimensions of the data points of a combination of the data points of the first data bin and the data points of the second data bin.

According to some embodiments of the invention, the transformation includes a multi-dimensional scaling (MDS) transformation.

According to some embodiments of the invention, the transformation includes a non-rigid transformation.

According to some embodiments of the invention, the transformation includes a rigid transformation.

According to some embodiments of the invention, the transformation includes a Coherent Point Drift (CPD) transformation.

According to some embodiments of the invention, the CPD transformation is based on identifying the set of corresponding data points in at least the first data bin and the second data bin of the plurality of data bins.

According to some embodiments of the invention, the transformation includes best-fit transformation.

According to some embodiments of the invention, the transformation further includes imposing spatial coherence on the transformed measurements.

According to some embodiments of the invention, the transformation further includes imposing temporal coherence on the transformed measurements.

According to an aspect of some embodiments of the present invention there is provided apparatus for imaging an anatomical structure based on electrical readings, the apparatus including a measurement component for receiving measurements from a plurality of electrodes, a processing component for classifying the measurements to a plurality of data bins, and a mapping component for identifying a set of corresponding data points in at least a first data bin and a second data bin of the plurality of data bins, calculating a transformation from the corresponding data points in the second data bin to the corresponding data points in the first data bin, projecting data points in the second data bin to data points in the first data bin using the transformation, producing a combined set of data points including the data points of the first data bin and the projected data points from the second data bin.

According to an aspect of some embodiments of the present invention there is provided a method for imaging an anatomical structure based on electrical readings, the method including receiving electrical readings from a plurality of electrodes, converting the electrical readings to data points, classifying each one of the data points as belonging to one of a plurality of data bins, identifying a set of corresponding data points in at least a first data bin and a second data bin of the plurality of data bins, projecting data points in the second data bin to data points in the first data bin using a transformation, producing a combined set of data points including the data points of the first data bin and the projected data points from the second data bin, and imaging the combined set of data points.

According to an aspect of some embodiments of the present invention there is provided apparatus for imaging an anatomical structure based on electrical readings, the apparatus including a data input component for receiving electrical readings from a plurality of electrodes, a processing component for converting the electrical readings to data points, a classifying component for classifying each one of the data points as belonging to one of a plurality of data bins, an identifying component for identifying correspondence of a set of data points in at least a first data bin and a second data bin of the plurality of data bins, a projecting component for projecting data points in the second data bin to data points in the first data bin using a transformation, a combining component for producing a combined set of data points including the data points of the first data bin and the projected data points from the second data bin, and an imaging component for producing an image from the combined set of data points. Producing an image may include converting data into a format suitable for display. In some embodiments the apparatus includes a display for displaying the image.

According to an aspect of some embodiments of the present invention there is provided a method for imaging an anatomical structure based on electrical readings, the method including receiving data points measured from a plurality of electrodes, classifying each one of the data points as belonging to one of a plurality of data bins, identifying a set of corresponding data points in at least a first data bin and a second data bin of the plurality of data bins, projecting data points in the second data bin to data points in the first data bin using a transformation, producing a combined set of data points including the data points of the first data bin and the projected data points from the second data bin, and imaging the combined set of data points.

According to an aspect of some embodiments of the present invention there is provided apparatus for imaging an anatomical structure based on electrical readings, the apparatus including a data input component for receiving data points measured from a plurality of electrodes, a classifying component for classifying each one of the data points as belonging to one of a plurality of data bins, an identifying component for identifying a set of corresponding data points in at least a first data bin and a second data bin of the plurality of data bins, a projecting component for projecting data points in the second data bin to data points in the first data bin using a transformation, a combining component for producing a combined set of data points including the data points of the first data bin and the projected data points from the second data bin, and an imaging component for producing an image from the combined set of data points, e.g., by converting the data points into a format suitable for display. In some embodiments the apparatus includes a display for displaying the image.

According to an aspect of some embodiments of the present invention there is provided a method for imaging an anatomical structure based on electrical readings, the method including receiving electrical readings from a plurality of electrodes, converting the electrical readings to data points, classifying each one of the data points as belonging to one of a plurality of data bins, projecting data points in a second data bin to data points in a first data bin using a transformation, producing a combined set of data points including the data points of the first data bin and the projected data points from the second data bin, and imaging the combined set of data points.

According to an aspect of some embodiments of the present invention there is provided apparatus for imaging an anatomical structure based on electrical readings, the apparatus including a data input component for receiving electrical readings from a plurality of electrodes, a processing component for converting the electrical readings to data points, a classifying component for classifying each one of the data points as belonging to one of a plurality of data bins, a projecting component for projecting data points in a second data bin to data points in a first data bin using a transformation, a combining component for producing a combined set of data points including the data points of the first data bin and the projected data points from the second data bin, and an imaging component for producing an image from the combined set of data points. In some embodiments the apparatus includes a display for displaying the image. Here, and in other embodiments that include an imaging component and a display, the imaging component preferably produces the image in a format suitable for display on that display.

According to an aspect of some embodiments of the present invention there is provided a method for imaging an anatomical structure based on electrical readings, the method including receiving data points measured from a plurality of electrodes, classifying each one of the data points as belonging to one of a plurality of data bins, projecting data points in a second data bin to data points in a first data bin using a transformation, producing a combined set of data points including the data points of the first data bin and the projected data points from the second data bin, and imaging the combined set of data points.

According to an aspect of some embodiments of the present invention there is provided apparatus for imaging an anatomical structure based on electrical readings, the apparatus including a data input component for receiving data points measured from a plurality of electrodes, a classifying component for classifying each one of the data points as belonging to one of a plurality of data bins, a projecting component for projecting data points in a second data bin to data points in a first data bin using a transformation, a combining component for producing a combined set of data points including the data points of the first data bin and the projected data points from the second data bin, and an imaging component for producing an image from the combined set of data points. In some embodiments the apparatus includes a display for displaying the image produced by the imaging component.

According to an aspect of some embodiments of the present invention there is provided a method of generating a combined image of a body part from a sequence of partially overlapping source images of the body part, each of the partially overlapping source images showing the body part at one of a plurality of different times, the source images being ordered in the sequence according to the different times, the method including defining a temporally coherent sequence of transformations, for registering the partially overlapping source images in the sequence with each other, registering the source images to each other using the defined temporally coherent sequence of transformations, to obtain co-registered images, and combining at least some of the co-registered images into a combined image.

According to some embodiments of the invention, the body part undergoes a periodic change, and the source images are ordered in the sequence according to their phase in a cycle of the periodic change.

According to some embodiments of the invention, the method includes setting one of the source images to be a master image, and the rest of the source images to be non-master images, defining for the non-master images, a temporally coherent sequence of transformations, each transformation registering a respective non-master image to the master image, transforming each non-master image, using the transformation defined for the non-master image, to obtain a corresponding transformed image, and combining at least some of the transformed images and the master image into a single combined image.

According to some embodiments of the invention, a difference between any two transformations defined for two consecutive source images is spatially coherent.

According to some embodiments of the invention, each transformation of the temporally coherent sequence of transformations is spatially coherent.

According to some embodiments of the invention, the temporally coherent sequence of transformations is defined using a cost function penalizing for spatial incoherence of a transformation in the sequence.

According to some embodiments of the invention, the temporally coherent sequence of transformations is defined using a cost function penalizing for spatial incoherence of a difference between sequential transformations in the sequence.

According to some embodiments of the invention, each one of the source images in the sequence shows the body part as imaged during a different time window, and time windows of at least some of the source images in the sequence partially overlap.

According to some embodiments of the invention, time windows of each two consecutive source images in the sequence partially overlap.

According to some embodiments of the invention, each one of the source images includes points representing values of electrical measurements, and the method further includes transforming the combined image into a transformed combined image including points representing locations in space.

According to some embodiments of the invention, each one of the source images in the sequence includes points representing locations in space.

According to some embodiments of the invention, each one of the source images is a point cloud, and the combining the co-registered images produces a combined point cloud, and further including reconstructing the combined image from the combined point cloud.

According to some embodiments of the invention, the reconstructing the combined image from the combined point cloud includes using a ball pivoting algorithm.

According to some embodiments of the invention, a specified location is marked on a plurality of the source images, and the transformations are defined to transform the location marked on the plurality of the source images to a same location.

According to some embodiments of the invention, the method further includes bringing an intra-body probe into the body part or to a vicinity thereof, receiving measurements from the intra-body probe, and generating the sequence of partially overlapping source images based on the measurements received from the intra-body probe.

According to an aspect of some embodiments of the present invention there is provided a non-transient computer readable medium containing program instructions for causing a computer to perform the method of any one of the above methods.

According to an aspect of some embodiments of the present invention there is provided a method of generating an image of a moving body part, the method including receiving a stream of measurements indicative of structure of partially overlapping portions of the body part, binning the stream of measurements to a sequence of bins, each bin including a set of measurements taken during a different time window, the time window partially overlapping with a time window of a sequential bin, generating, from the sequence of bins, a sequence of partially overlapping source images of the body part, and generating from the sequence of partially overlapping images a combined image.

According to some embodiments of the invention, classifying the stream of measurements to two or more groups of measurements, each group corresponding to a different movement mode of the body part, and for at least one of the groups binning the measurements to a sequence of bins, each including a set of measurements taken in a different time window, generating, from the sequence of bins, a sequence of partially overlapping source images of the body part, and generating a combined image from the source images.

According to some embodiments of the invention, the binning, generating a sequence of partially overlapping source images, and generating a combined image, is carried out for two or more of the groups, to generate two or more combined images.

According to some embodiments of the invention, the method includes registering the two or more combined images to each other.

According to some embodiments of the invention, the generation of the combined image is by a method according to any one of the above-mentioned methods.

According to some embodiments of the invention, the body part is a heart or a portion thereof, and the movement modes include a cardiac rhythm selected from a sinusoidal beat, and atrial fibrillation.

According to some embodiments of the invention, the method further includes bringing an intra-body probe into the body part or to a vicinity thereof, receiving measurements from the intra-body probe, and generating the sequence of partially overlapping source images based on the measurements received from the intra-body probe.

According to an aspect of some embodiments of the present invention there is provided a non-transient computer readable medium containing program instructions for causing a computer to perform any one of the above methods.

According to an aspect of some embodiments of the present invention there is provided a method of generating a movie of a beating heart, the method including receiving a sequence of partially overlapping images of the beating heart, each image based on data collected during a different time window, the images being ordered in the sequence according to a time order of the time windows, generating a single movie frame for each one of the images, and ordering the single movie frames according to the ordering of the images in the sequence of images to obtain the movie, wherein generating a single movie frame for each one of the images includes setting the one of the images to be a master image, and the rest of the images to be non-master images, defining a temporally coherent sequence of transformations, each registering a corresponding non-master image to the master image, transforming each non-master image according to the transformation defined therefor to obtain a corresponding transformed image, combining the transformed images and the master image into the single movie frame for the one of the images.

According to some embodiments of the invention, a difference between any two transformations defined for two consecutive images is spatially coherent.

According to some embodiments of the invention, each of the transformations defined is spatially coherent.

According to an aspect of some embodiments of the present invention there is provided a non-transient computer readable medium containing program instructions for causing a computer to perform any one of the above-mentioned method.

According to an aspect of some embodiments of the present invention there is provided a system configured to carry out any one of the above-mentioned methods.

According to an aspect of some embodiments of the present invention there is provided a method for combining data sets, each indicative of a structure of a body organ, the method including receiving two data sets, each data set including information indicative of a structure of the body organ, wherein at least some data points in each set are indicative of structure of a same portion of the body organ, determining a first data point in each one of the two data sets, the first data points being indicative of the structure of the same portion of the body organ, and projecting a first one of the two data sets into a data set having a common coordinate system with a second one of the two data sets, based on the first data points determined in each one of the two data sets.

According to some embodiments of the invention, the projecting the first one of the two data sets into a data set having a common coordinate system includes projecting the first one of the two data sets into the second one of the two data sets.

According to some embodiments of the invention, at least some data in the two data sets was measured during partially-overlapping time periods.

According to an aspect of some embodiments of the present invention there is provided a method of imaging an anatomical structure based on sensor readings, the method including receiving sensor readings from a plurality of sensors, converting the sensor readings to data points, classifying each one of the data points as belonging to one of a plurality of data bins, identifying a first set of data points in a first data bin and a second set of data points in a second data bin of the plurality of data bins, each point in the first set corresponding to a point in the second set, calculating a transformation from the second set of data points to the first set of data points, projecting data points in the second data bin to data points in the first data bin using the transformation, producing a combined set of data points including the data points of the first data bin and the projected data points from the second data bin, and imaging the anatomical structure based on data included in the combined set of data points.

According to some embodiments of the invention, the sensors include electrodes, the sensor readings include electrical readings, and converting the electrical readings to data points includes converting from values of electrical readings to location values in space.

According to some embodiments of the invention, the anatomical structure includes a heart chamber.

According to some embodiments of the invention, receiving electrical reading includes receiving measurements from a plurality of electrodes on an intra-body probe and from at least one body surface electrode.

According to some embodiments of the invention, receiving sensor readings further includes receiving measurements selected from a group consisting of electric potential, electric current, electric permittivity, time, location, pressure, blood pressure, nasal air flow, blood chemical composition, and temperature.

According to some embodiments of the invention, the data points include a dimension selected from a group consisting of time, location in space, pressure, temperature, phase in cardiac cycle, phase in breathing cycle, amplitude of breathing motion, category of cardiac rhythm, phase in cycle of adjacent heart chamber, and category of breathing type.

According to some embodiments of the invention, the classifying each one of the data points as belonging to one of a plurality of data bins includes classifying at least some of the data points as belonging to at least one data bin selected from a group consisting of an atrial fibrillation (AF) data bin, an arrhythmia data bin.

According to some embodiments of the invention, the transformation includes a transformation from a data bin including data points of a cardiac rhythm classified as atrial fibrillation (AF) to a data bin including data points of a non-AF cardiac rhythm.

According to some embodiments of the invention, the transformation includes a transformation selected from a group consisting of (a) a transformation from a data bin including data points of a first cardiac rhythm category to a data bin including data points of a second cardiac rhythm category, (b) a transformation from a data bin including data points of a first breathing rhythm category to a data bin including data points of a second breathing rhythm category, and (c) a transformation from a data bin including data points of a first cardiac rhythm category to a data bin including data points of a second cardiac rhythm category.

According to some embodiments of the invention, the transformation includes a transformation selected from a group consisting of a multi-dimensional scaling (MDS) transformation, a non-rigid transformation, a rigid transformation, a Coherent Point Drift (CPD) transformation, and a best-fit transformation.

According to some embodiments of the invention, the transformation further includes imposing spatial coherence on the transformed measurements.

According to some embodiments of the invention, the transformation further includes imposing temporal coherence on the transformed measurements.

According to an aspect of some embodiments of the present invention there is provided apparatus for imaging an anatomical structure based on electrical readings, the apparatus including an intra-body electrode, a measurement component configured to receive measurements from the intra-body electrode, a processor configured to classify the measurements to a plurality of data bins, and a mapping component configured to identify a set of corresponding data points in at least a first data bin and a second data bin of the plurality of data bins, calculate a transformation from the corresponding data points in the second data bin to the corresponding data points in the first data bin, project data points in the second data bin to data points in the first data bin using the transformation, and produce a combined set of data points including the data points of the first data bin and the projected data points from the second data bin.

According to an aspect of some embodiments of the present invention there is provided a method of imaging an anatomical structure based on electrical readings, the method including receiving electrical readings from a plurality of electrodes, converting the electrical readings to data points, classifying each one of the data points as belonging to one of a plurality of data bins, identifying a set of corresponding data points in at least a first data bin and a second data bin of the plurality of data bins, projecting data points in the second data bin to data points in the first data bin using a transformation, producing a combined set of data points including the data points of the first data bin and the projected data points from the second data bin, and imaging the anatomical structure based on data included in the combined set of data points.

According to an aspect of some embodiments of the present invention there is provided apparatus for imaging an anatomical structure based on electrical readings, the apparatus including an intra-body electrode, a data input component configured to receive electrical readings from the intra-body electrode, a processing component configured to convert the electrical readings to data points, a classifying component configured to classify each one of the data points as belonging to one of a plurality of data bins, an identifying component configured to identify correspondence of a set of data points in at least a first data bin and a second data bin of the plurality of data bins, a projecting component configured to project data points in the second data bin to data points in the first data bin using a transformation, a combining component configured to produce a combined set of data points including the data points of the first data bin and the projected data points from the second data bin, and an imaging component configured to image the combined set of data points.

According to an aspect of some embodiments of the present invention there is provided a method for imaging an anatomical structure based on electrical readings, the method including receiving data points measured from a plurality of electrodes, classifying each one of the data points as belonging to one of a plurality of data bins, identifying a set of corresponding data points in at least a first data bin and a second data bin of the plurality of data bins, projecting data points in the second data bin to data points in the first data bin using a transformation, producing a combined set of data points including the data points of the first data bin and the projected data points from the second data bin, and imaging the anatomical structure based on data included in the combined set of data points.

According to an aspect of some embodiments of the present invention there is provided apparatus for imaging an anatomical structure based on electrical readings, the apparatus including a data input component for receiving data points measured from a plurality of electrodes, a classifying component for classifying each one of the data points as belonging to one of a plurality of data bins, an identifying component for identifying a set of corresponding data points in at least a first data bin and a second data bin of the plurality of data bins, a projecting component for projecting data points in the second data bin to data points in the first data bin using a transformation, a combining component for producing a combined set of data points including the data points of the first data bin and the projected data points from the second data bin, and an imaging component for imaging the combined set of data points.

According to an aspect of some embodiments of the present invention there is provided a method for imaging an anatomical structure based on electrical readings, the method including receiving electrical readings from a plurality of electrodes, converting the electrical readings to data points, classifying each one of the data points as belonging to one of a plurality of data bins, projecting data points in a second data bin to data points in a first data bin using a transformation, producing a combined set of data points including the data points of the first data bin and the projected data points from the second data bin, and imaging the combined set of data points.

According to an aspect of some embodiments of the present invention there is provided apparatus for imaging an anatomical structure based on electrical readings, the apparatus including a data input component for receiving electrical readings from a plurality of electrodes, a processing component for converting the electrical readings to data points, a classifying component for classifying each one of the data points as belonging to one of a plurality of data bins, a projecting component for projecting data points in a second data bin to data points in a first data bin using a transformation, a combining component for producing a combined set of data points including the data points of the first data bin and the projected data points from the second data bin, and an imaging component for imaging the combined set of data points.

According to an aspect of some embodiments of the present invention there is provided a method for imaging an anatomical structure based on electrical readings, the method including receiving data points measured from a plurality of electrodes, classifying each one of the data points as belonging to one of a plurality of data bins, projecting data points in a second data bin to data points in a first data bin using a transformation, producing a combined set of data points including the data points of the first data bin and the projected data points from the second data bin, and imaging the combined set of data points.

According to an aspect of some embodiments of the present invention there is provided apparatus for imaging an anatomical structure based on electrical readings, the apparatus including a data input component for receiving data points measured from a plurality of electrodes, a classifying component for classifying each one of the data points as belonging to one of a plurality of data bins, a projecting component for projecting data points in a second data bin to data points in a first data bin using a transformation, a combining component for producing a combined set of data points including the data points of the first data bin and the projected data points from the second data bin, and an imaging component for imaging the combined set of data points.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product.

Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert, who wanted to manually perform similar tasks, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWING(S)

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

Figure 4A:
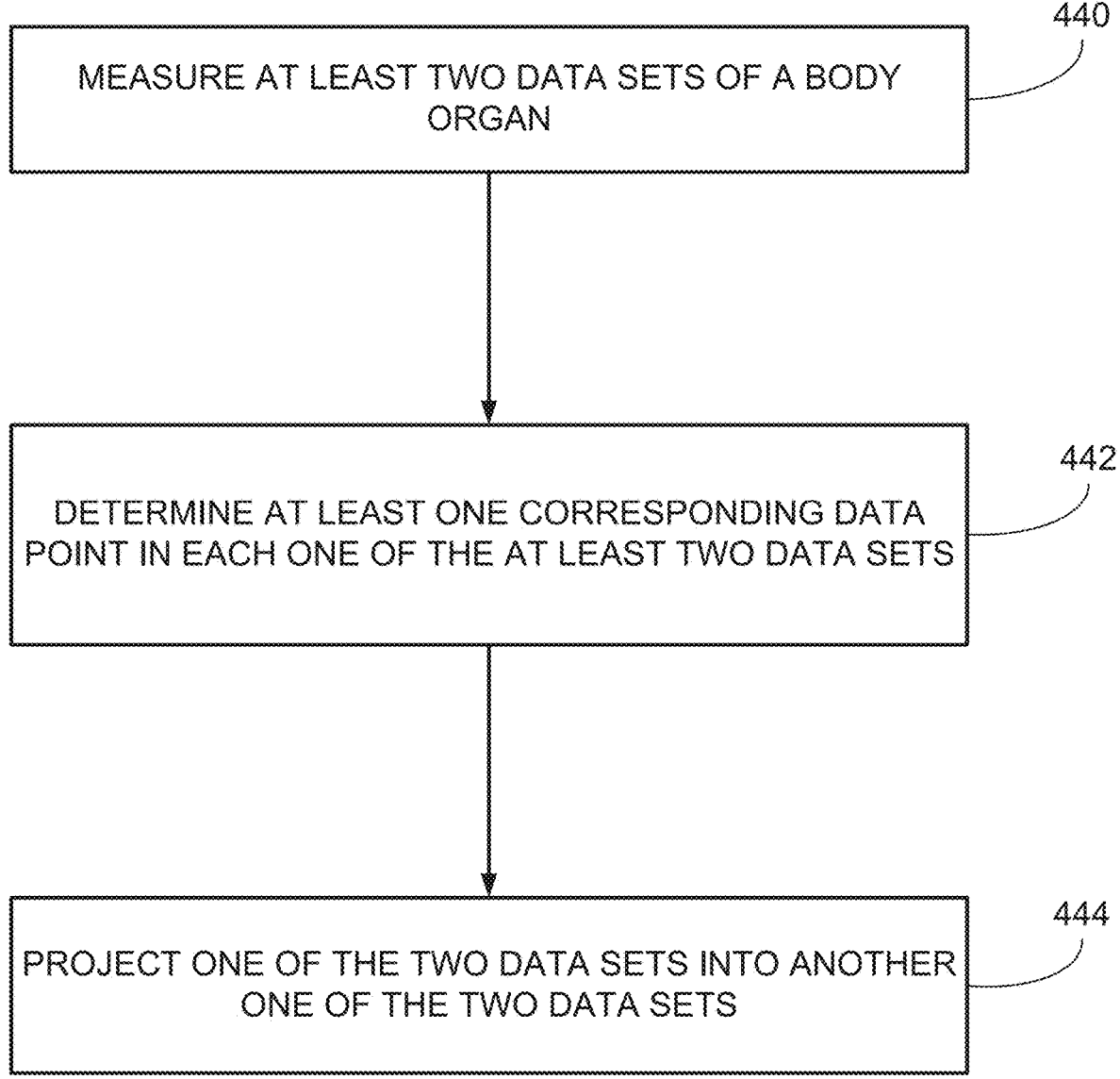
Figure 4B:
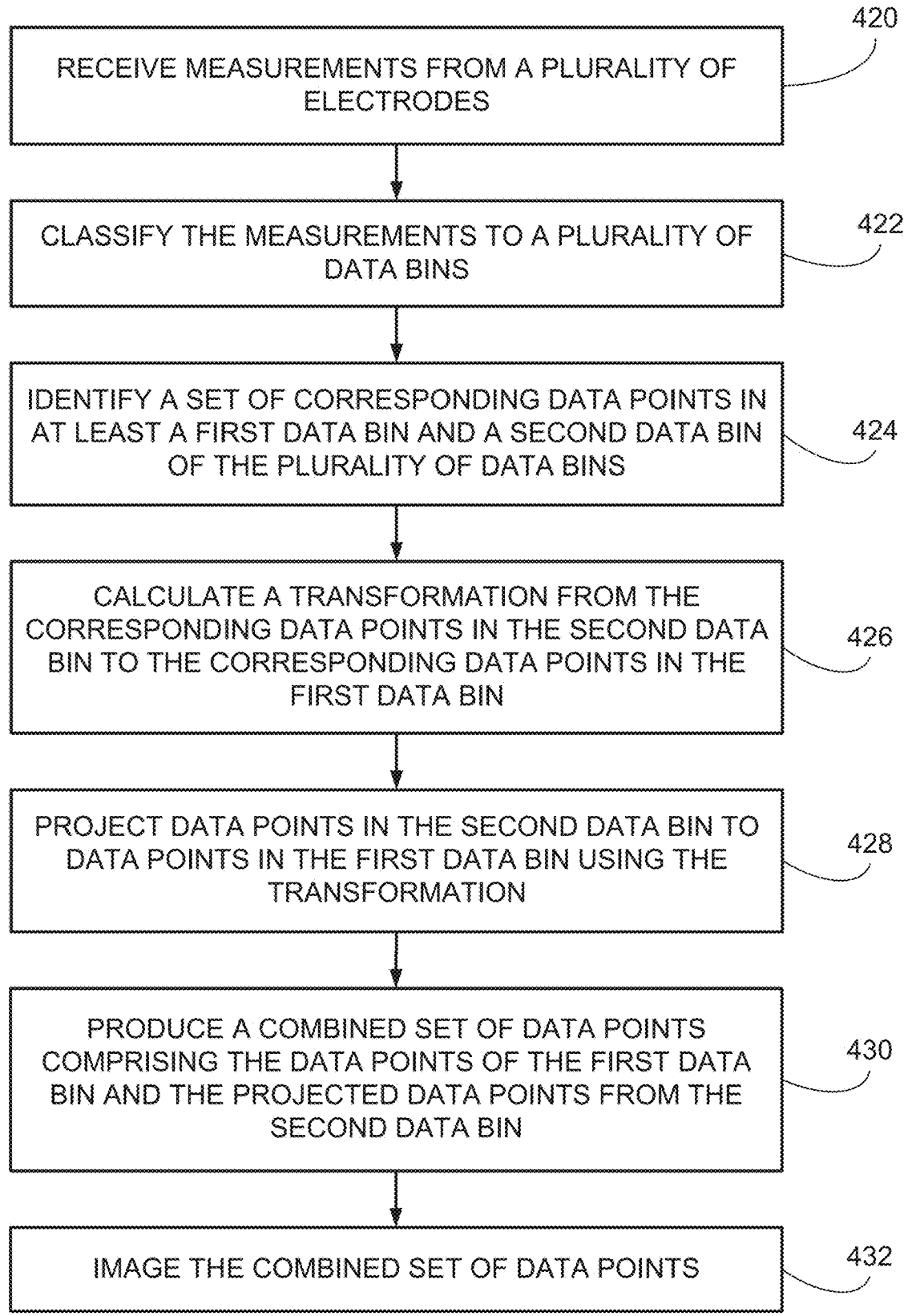
Figure 5B:
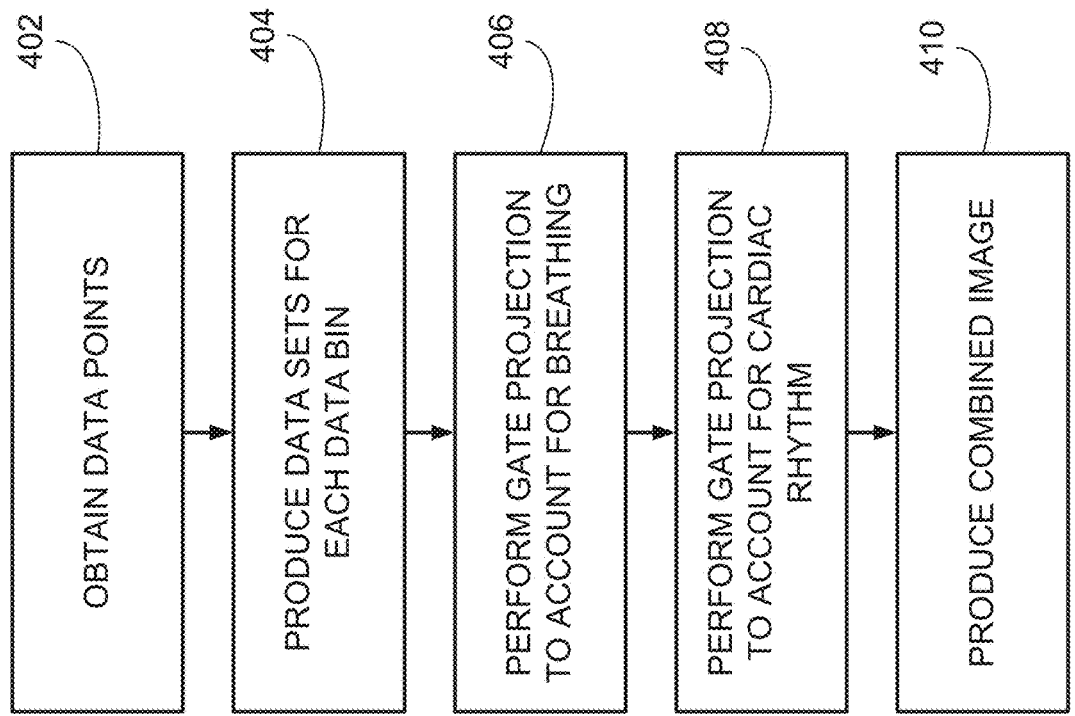
Figure 5A:
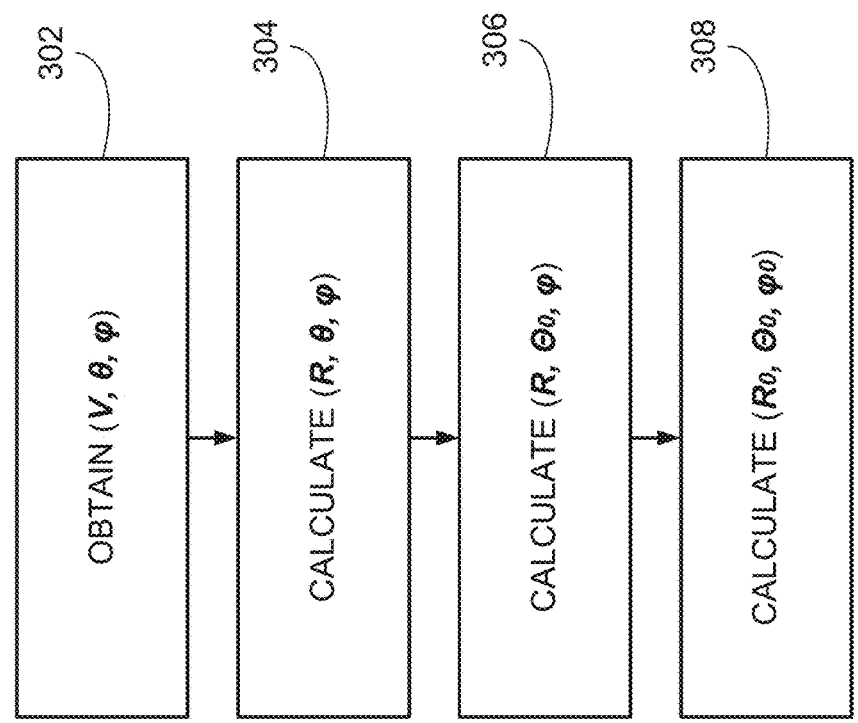
Figure 6A:
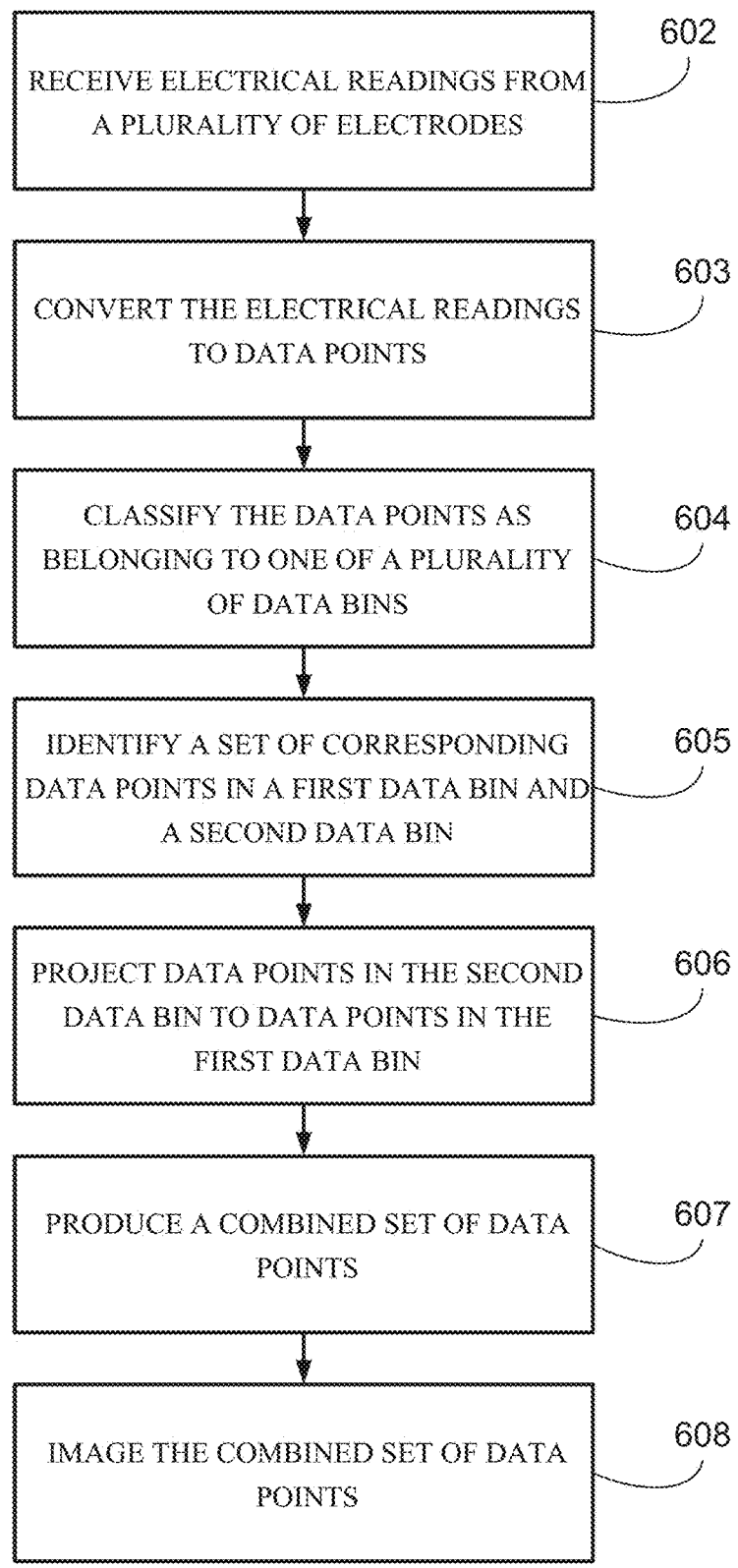
Figure 6B:
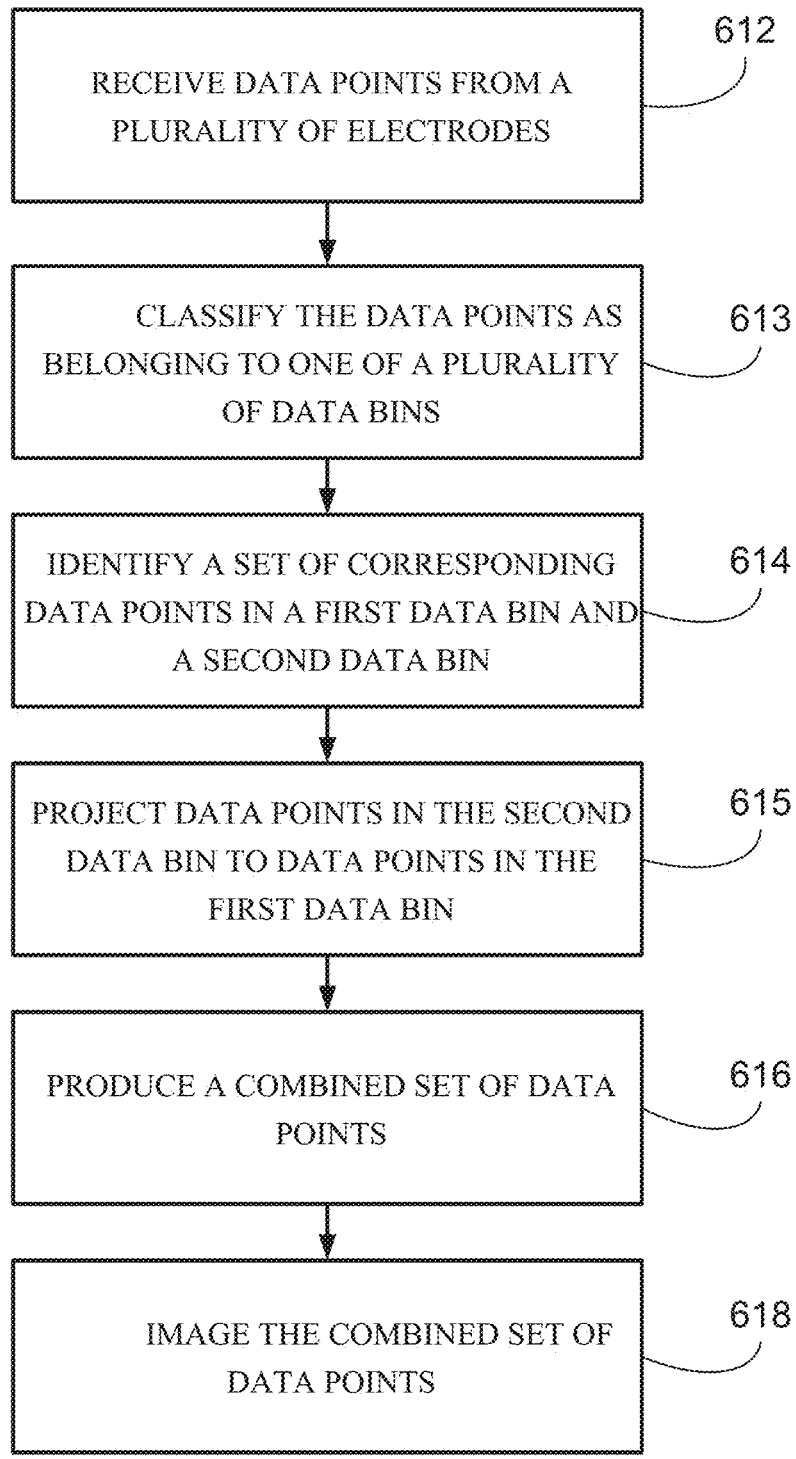
Figure 6C:
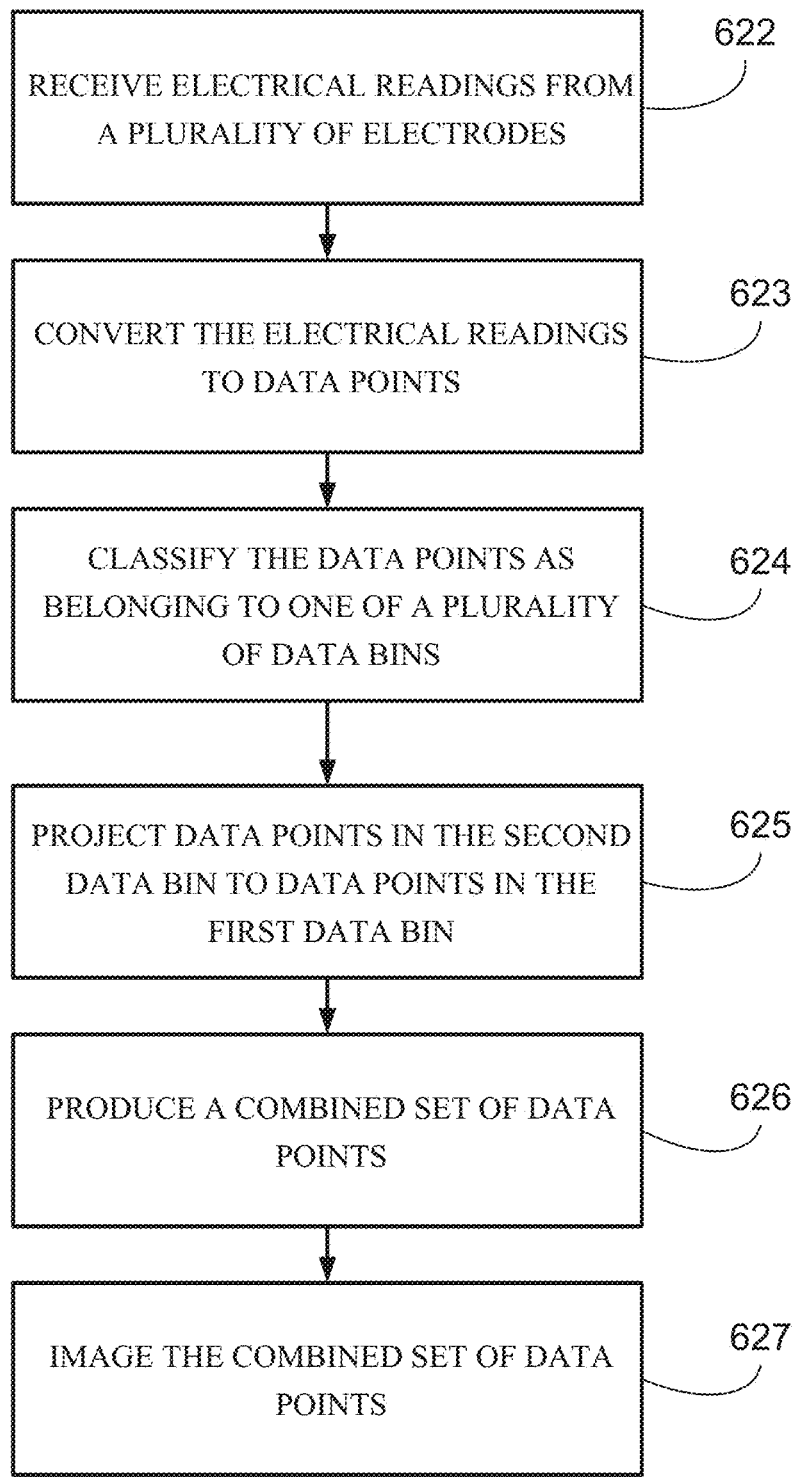
Figure 6D:
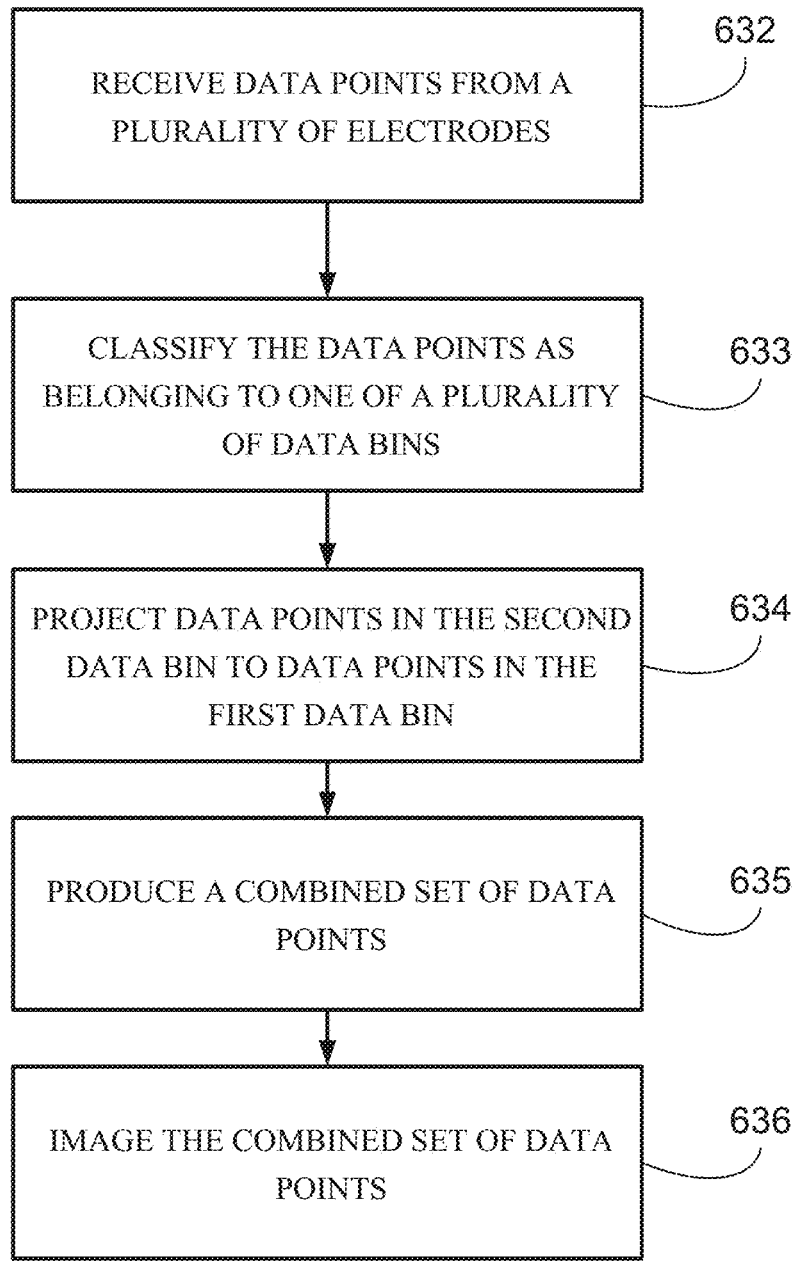
Figure 7A:
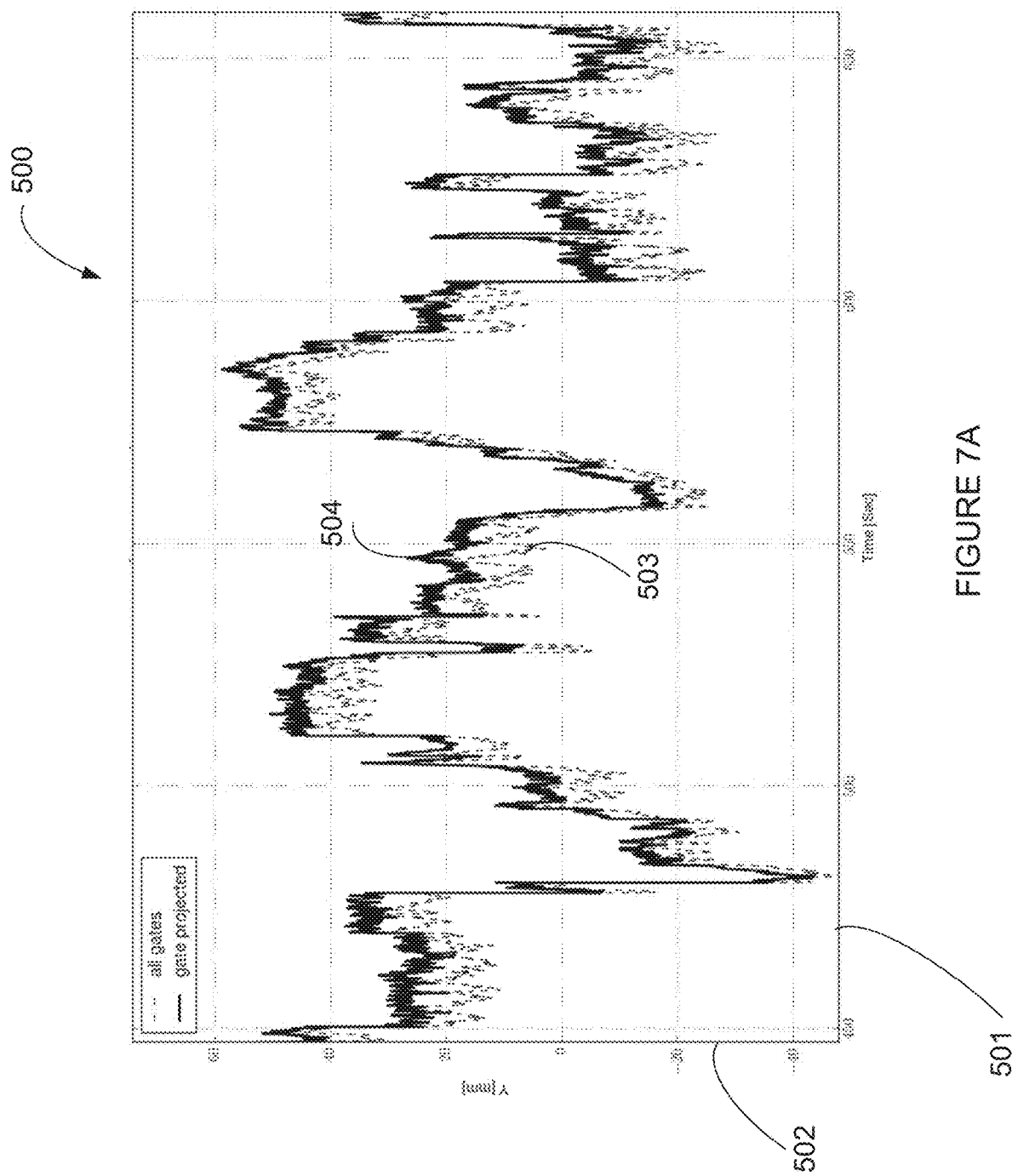
Figure 7B:
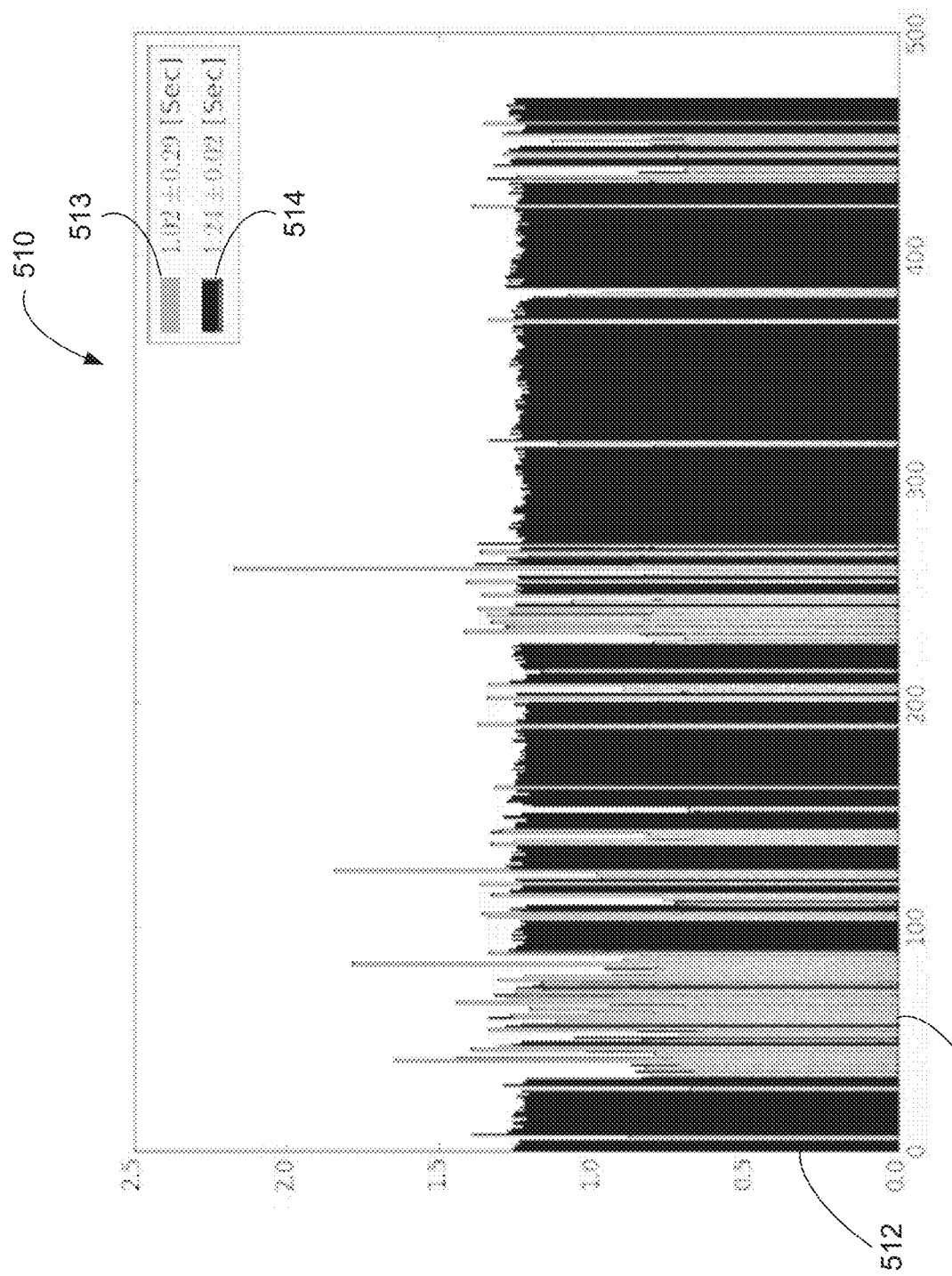
Figure 8:
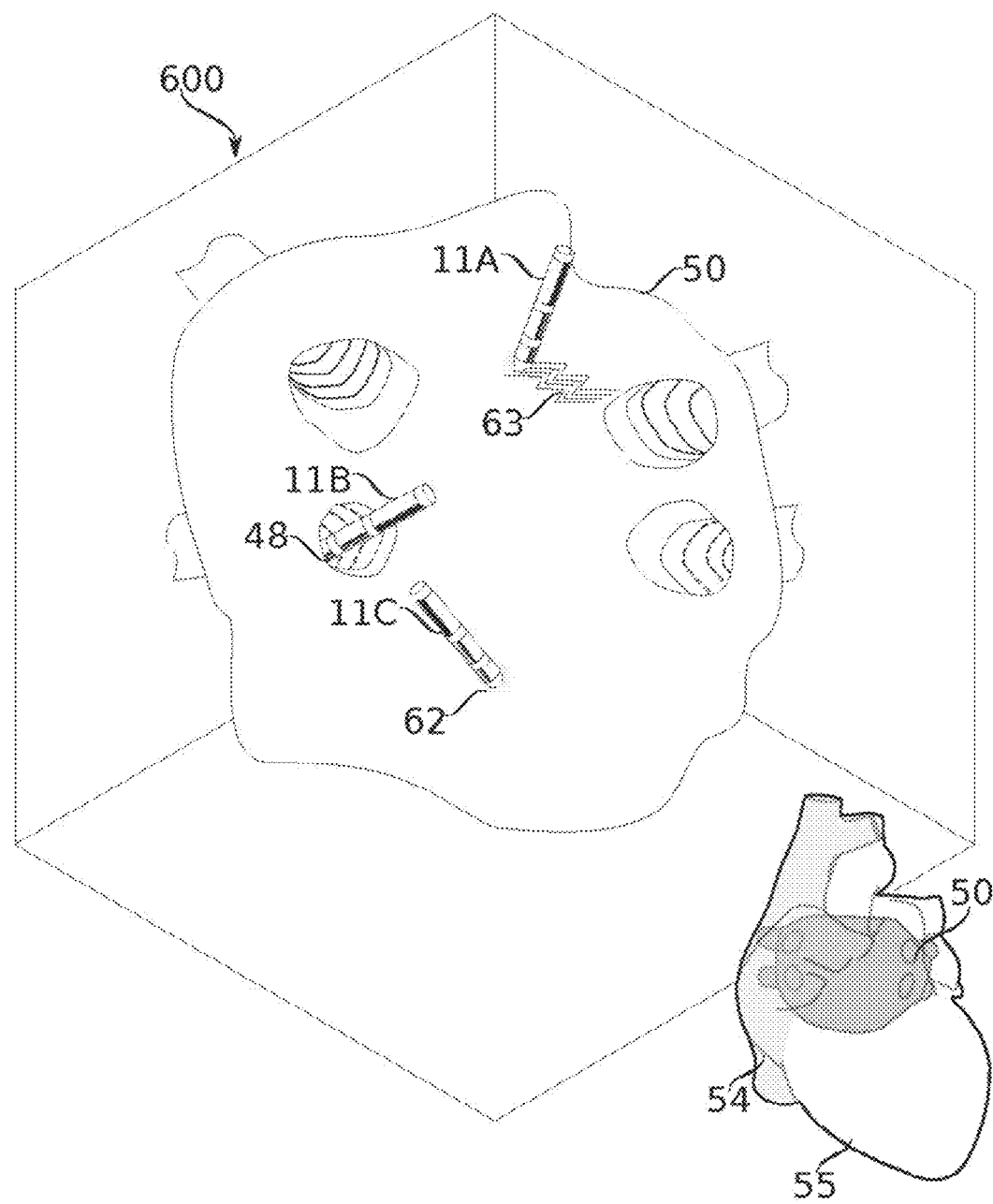
Figure 9:
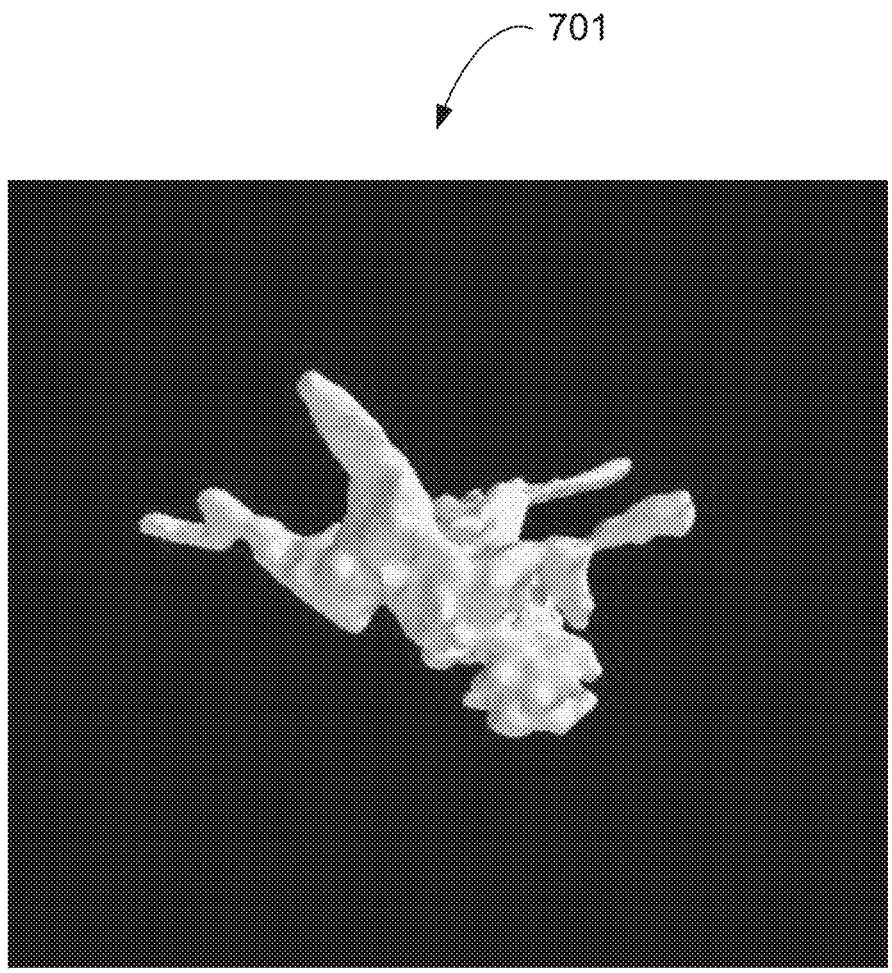
Figure 10A:
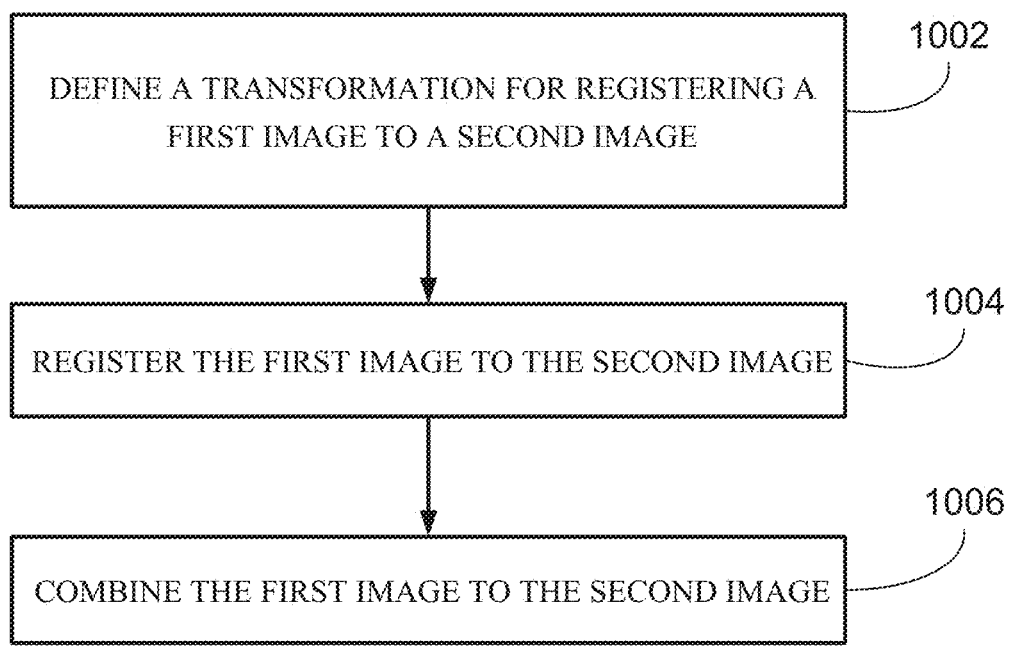
Figure 10B:
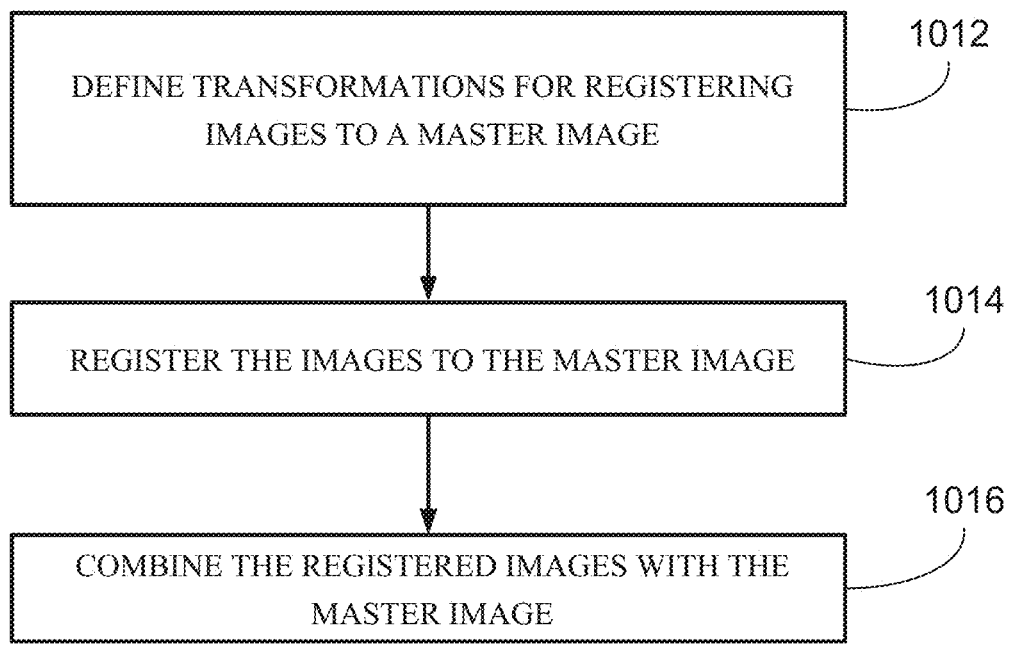
Figure 11A:
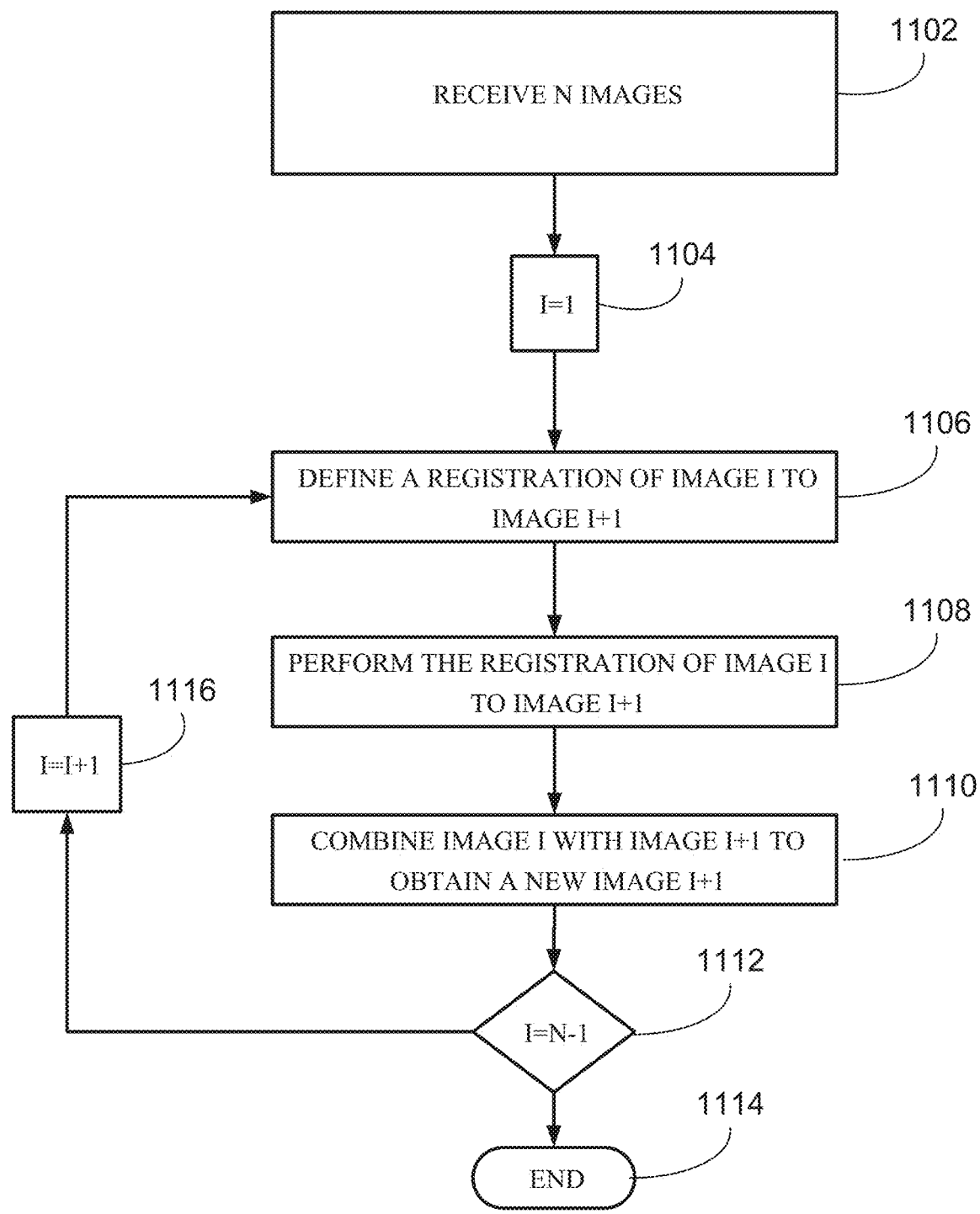
Figure 11B:
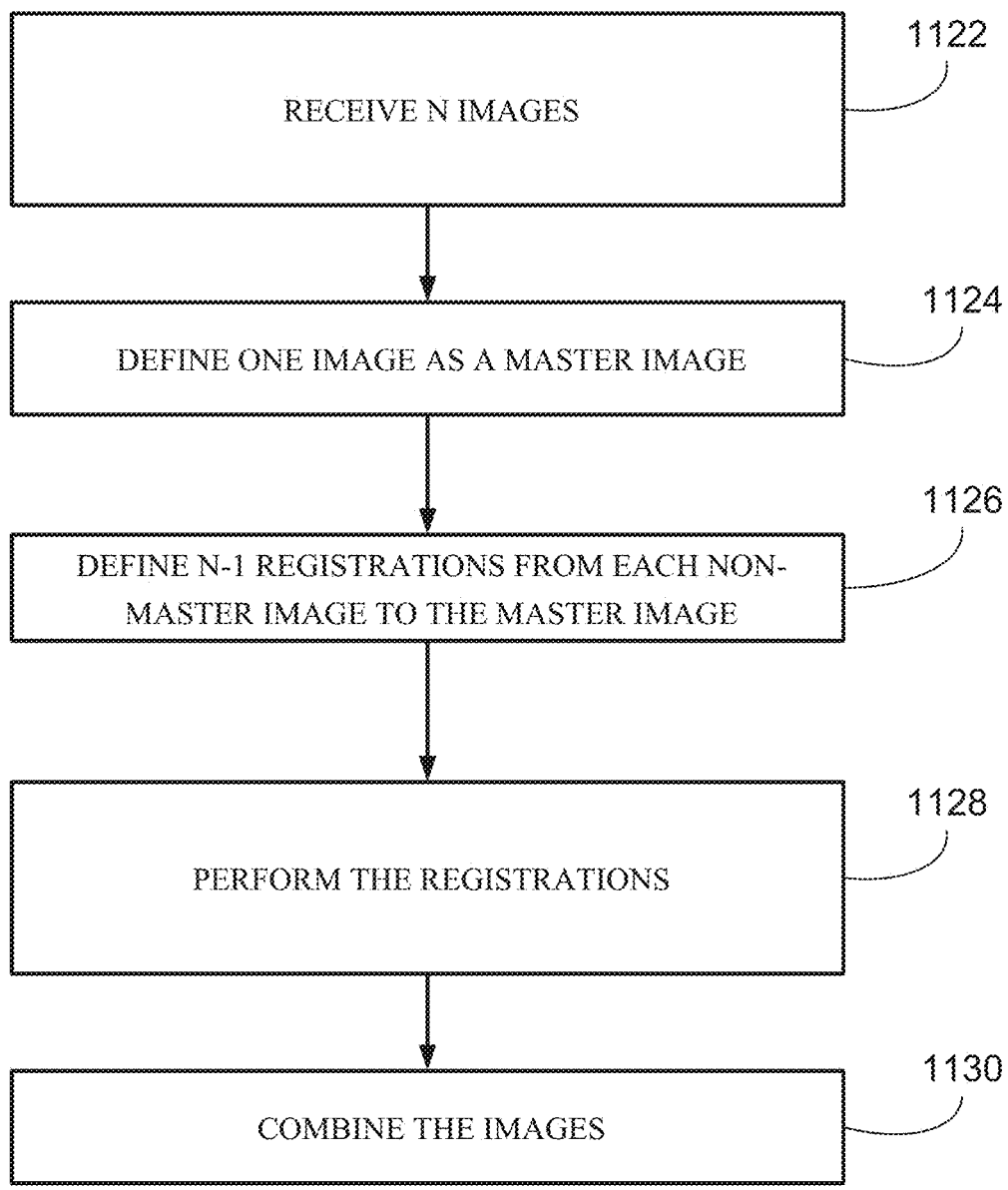
Figure 11C:
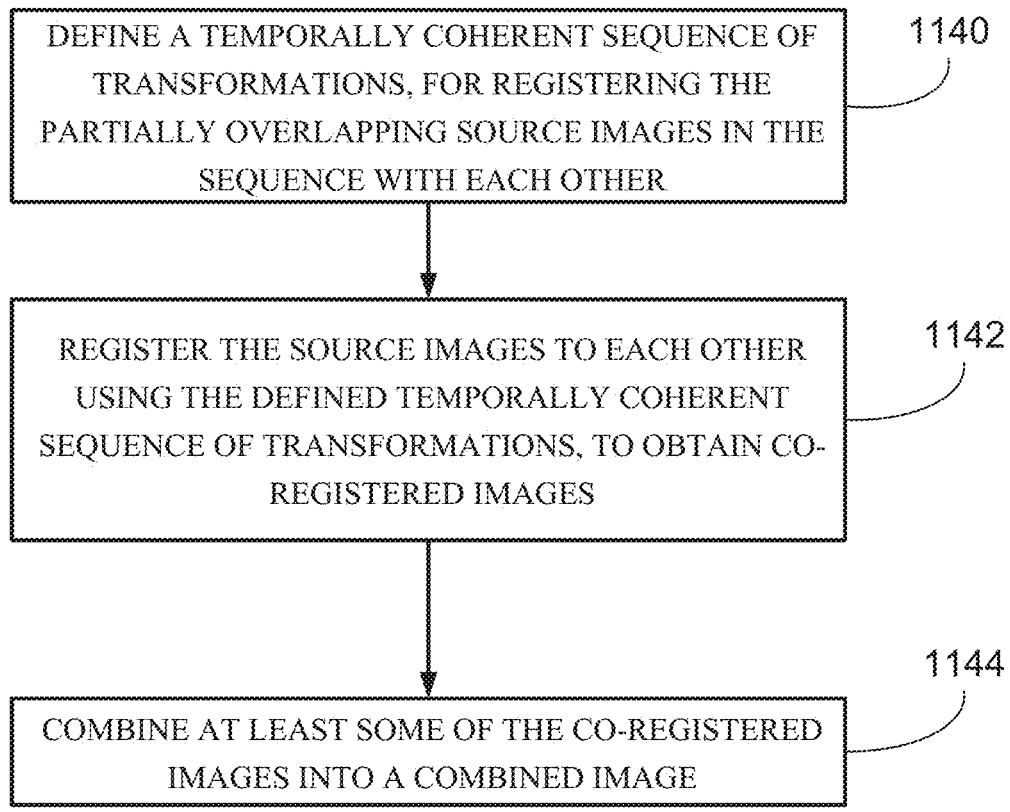
Figure 12:
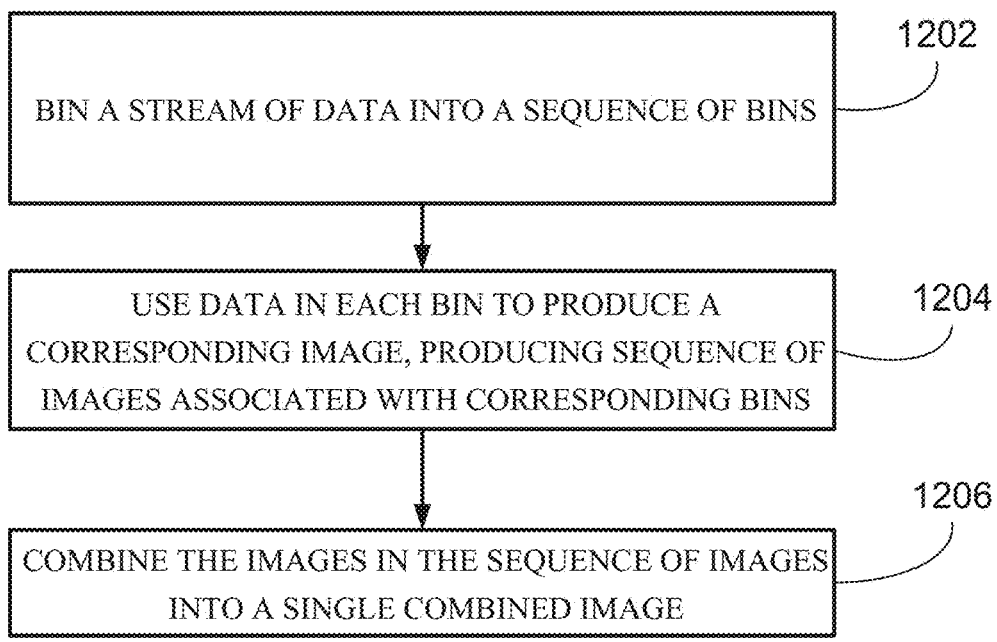
Figure 13:
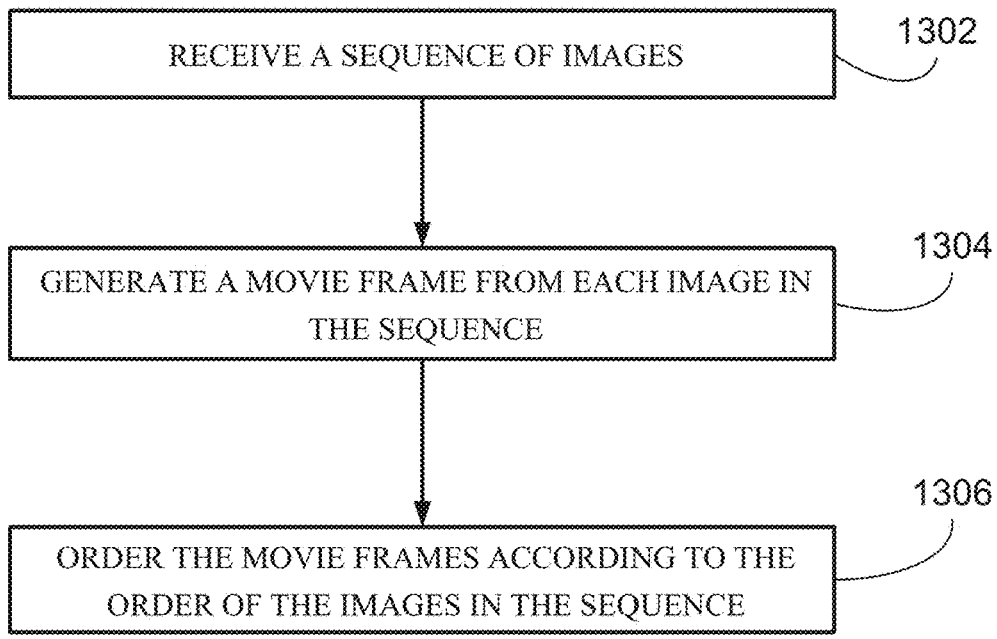

Each of FIGS. 3C, 3D, 3E, and 3F is a simplified block diagram illustration of a system for imaging an anatomical structure based on electrical readings according to some embodiments of the invention;

FIG. 4A is a simplified flowchart illustration of a method for producing a model of a body organ based on electrical readings according to some embodiments of the invention;

FIG. 4B is a simplified flowchart illustration of a method for imaging a patient organ based on electrical readings according to some embodiments of the invention;

FIG. 5A is a simplified flowchart illustration of a method for combining gate-projected data points according to some embodiments of the invention;

FIG. 5B is a simplified flowchart illustration of a method for combining gate-projected data points to produce a combined image according to some embodiments of the invention;

FIG. 6A is a simplified flowchart of a method for imaging an anatomical structure based on electrical readings according to an exemplary embodiment of the invention;

FIG. 6B is a simplified flowchart of a method for imaging an anatomical structure based on electrical readings according to an exemplary embodiment of the invention;

FIG. 6C is a simplified flowchart of a method for imaging an anatomical structure based on electrical readings according to an exemplary embodiment of the invention;

FIG. 6D is a simplified flowchart of a method for imaging an anatomical structure based on electrical readings according to an exemplary embodiment of the invention;

FIG. 7A is a graph showing an example effect of gate-projection on data points according to some embodiments of the invention;

FIG. 7B is a graph showing a normal cardiac rhythm and an abnormal cardiac rhythm differentiated according to some embodiments of the invention;

FIG. 8 is a simplified line drawing illustration of methods of gathering position-identifying information using intra-body probes according to some embodiments of the invention;

FIG. 9 is an image of a heart produced following gate projection of several data bins into one common reference data bin according to some embodiments of the invention;

FIG. 10A is a flowchart illustration of a method of generating an image of a body part according to an exemplary embodiment of the invention;

FIG. 10B is a flowchart illustration of a method of generating an image of a body part according to an exemplary embodiment of the invention;

FIG. 11A is a simplified flowchart illustration of a method of combining N images into one according to an exemplary embodiment of the invention;

FIG. 11B is a simplified flowchart illustration of a method of combining N images into one according to an exemplary embodiment of the invention;

FIG. 11C is a simplified flowchart illustration of a method of generating a combined image of a body part from a sequence of partially overlapping source images of the body part according to an exemplary embodiment of the invention;

FIG. 12 is a simplified flowchart illustration of a method of generating an image from a stream of data according to an exemplary embodiment of the invention; and FIG. 13 is a simplified flowchart illustration of a method for producing a movie of a beating heart from a sequence of images of the beating heart according to an exemplary embodiment of the invention.

DESCRIPTION OF SPECIFIC EMBODIMENTS OF THE INVENTION

The present invention, in some embodiments thereof, relates to transforming medical data captured under different circumstances to a common framework, and, more particularly, but not exclusively, to transforming values of data points obtained from an intra-body probe to a common coordinate system in order to use the data points to image and/or model anatomical structure.

Some embodiments of the present invention include modelling a structure of a body organ or portion thereof based on data received from a probe when there is mutual movement between the probe and the body organ portion to be modelled.

Some embodiments of the present invention include improvement of modelling a structure of a body organ or portion thereof based on using data received from a probe when there is mutual movement between the probe and the body organ portion to be modelled.

The term "image" is used throughout the present specification and claims to mean a visual representation of a structure, potentially suitable for display by a display device. The term "image" when used as a verb—to image—is used throughout the present specification and claims to mean to produce or generate an image.

The term "model" is used throughout the present specification and claims to mean a data set which includes one or more data values that represent a structure of one or more location(s) in a patient's body. The term "model" when used as a verb—to model—in all its grammatical forms is used throughout the present specification and claims to mean to produce or generate a model or to edit data in a model.

In various embodiments, the medical data optionally includes values of location (e.g. spatial coordinates), time (e.g. clock time and/or time along a heartbeat cycle), electrical readings (e.g. current and/or electric potential values); values computed based on the electrical readings (e.g. impedance, various other dielectric properties); and additional physical data (e.g. pH, color, pressure).

An example field in which embodiments of the invention may be practiced is construction of a model of an anatomical structure (e.g., body cavity). Construction of the model of an anatomical structure may include mapping data, e.g., electrical readings, to positions within the structure. In some embodiments an image of the model of an anatomical structure is optionally made. In some embodiments the image is optionally displayed.

In some embodiments, mapping electrical readings to positions within the structure is performed based on knowing, for at least some electric readings, to which element or position in the structure the electrical readings belong. For example, some locations in a heart are known to provide higher electrical readings than other locations. One such example is the openings of the pulmonary veins to the left atrium, where blood is exceptionally rich in oxygen, and this oxygen content is reflected in marked impedance values. In some embodiments a transition between low electrical reading to higher electrical reading is optionally mapped to a location in the heart where such transition is known to occur.

In some embodiments, mapping electrical readings to locations in the structure is performed based on knowing, for at least some electric readings, to which location in the structure the electrical readings belong. For example, some locations in a heart are known to provide higher electrical readings than other locations. In some embodiments a transition between low electrical reading(s) to higher electrical reading(s) is optionally mapped to a location in the structure where such transition is known to occur.

In some embodiments, mapping readings from other sensors to locations in space is optionally performed based on knowing, for at least some of the readings from the other sensors, to which location in space or in the structure the readings belong. For example, some locations in a body lumen, such as intestines for example, are known to provide different pH readings than other locations. In some embodiments a transition between values of pH reading(s) is optionally mapped to a location in space, or location in the structure, where such transition is known to occur.

An example field in which embodiments of the invention may be practiced is, by way of a non-limiting example, construction of a model of cardiac structure and/or cardiac imaging.

An example field in which embodiments of the invention may be practiced is cardiac imaging and/or construction of a model of cardiac structure, optionally as part of a cardiac ablation procedure.

Introduction

According to some embodiments, data may be collected at different times during a medical treatment to compose an image and/or map and/or construct a model of an anatomical structure (e.g., a body cavity). As used herein, the language "constructing a model of an anatomical structure" is used to describe producing a set of data describing the anatomical structure, optionally in one, two or three dimensions, optionally including physical attributes such as conductance, electric potential, color, pH and so on.

In some embodiments, the model is constructed based on measurements made at different times, and at different times different details were observed and/or different measurements were made. In some such embodiments, a frozen model is made by registering all the details to a common framework, such as to a common coordinate system, and then combining the details together into a frozen model, which includes details measured at different times. In some embodiments, spatial relationships between details which were measured only some of the time, are kept in the frozen model even when a modeled body part deforms during the measurements. In some embodiments a time of measurement is associated with the measurements and optionally included in dataset which contains the measurements.

As used herein, the language "imaging an anatomical structure" is used to describe producing an image of the anatomical structure, optionally in one, two or three dimensions.

In exemplary embodiments where a set of data is used to image the anatomical structure, the language "imaging an anatomical structure" is used to describe producing a set of data suitable for displaying an image of the anatomical structure, optionally in one, two or three dimensions, optionally additionally including time in the set of data.

In cardiac imaging and/or in using a roving catheter inside a heart chamber to construct a model of cardiac structure, data may be collected at different times (e.g., when the catheter roves at different locations inside the heart) to compose an image and/or map and/or construct a model of the heart.

The data may include, inter alia, catheter locations, locally sensed information (e.g. pressure, voltage, impedance, activation times, temperature, conduction, etc.) and information sensed from outside a body. The data collected (i.e. in the temporal or spatial domains) is optionally used for forming a map or model of the body cavity; such as a heart chamber.

Cardiac ablation procedures may include use of catheterized intra-body ablation probes (for example, RF ablation probes). Such procedures are performed, for example, in the treatment of cardiac arrhythmia.

One form of catheter ablation known as RF ablation relies on heating caused by interaction between a high-frequency alternating current (e.g., 350-500 kHz) introduced to a treatment region, and a dielectric material (e.g., tissue) in the treatment region. One variable affecting the heating is a frequency-dependent relative permittivity K of tissue being treated. A (unit-less) relative permittivity of a material (herein, κ or dielectric constant) is a measure of how the material of the tissue reduces an electrical field imposed across it (storing and/or dissipating energy of the electrical field). Relative permittivity is commonly expressed as $$\kappa = \varepsilon_r(\omega) = \frac{\varepsilon(\omega)}{\varepsilon_0}, \text{ where } \omega = 2\pi f,$$

and f is the frequency (of an imposed voltage signal). In general, $\varepsilon_r(\omega)$ is complex valued; that is: $\varepsilon_r(\omega)=\varepsilon'_r(\omega)+i\varepsilon''_r(\omega)$.

The real part $\varepsilon'_r(\omega)$ is a measure of how energy of an applied electrical field is stored in the tissue (at a given electrical field frequency), while the imaginary part $\varepsilon''_r(\omega)$ is a measure of energy dissipated. It is this dissipated energy that is converted, for example, into heat for ablation. Loss in turn is optionally expressed as a sum of dielectric loss $\varepsilon''_{rd}$ and conductivity a as $$\varepsilon''_r(\omega) = \varepsilon''_{rd} + \frac{\sigma}{\omega \cdot \varepsilon_0}.$$

Any one of the above parameters, namely κ, ε, $\varepsilon'_r$, $\varepsilon''_r$, σ, and/or $\varepsilon''_{rd}$, may be referred to herein as a dielectric parameter. The term dielectric parameter encompasses also parameters that are directly derivable from the above-mentioned parameters, for example, loss tangent, expressed as $$\tan \sigma = \frac{\varepsilon''_r}{\varepsilon'_r},$$

complex refractive index, expressed as $$n = \sqrt{\varepsilon_r},$$

and impedance, expressed as $$Z(\omega) = \sqrt{\frac{i\omega}{\sigma + i\omega\varepsilon_r}} \text{ (with } i = \sqrt{-1}\text{)}.$$

Herein, a value of a dielectric parameter of a material may be referred to as a dielectric property of the material. For example, having a relative permittivity of about 100,000 is a dielectric property of a 0.01 Molar KCl solution in water at a frequency of 1 kHz, at about room temperature (20°, for example; it should be noted that some dielectric properties exhibit temperature dependence). Optionally, a dielectric property more specifically comprises a measured value of a dielectric parameter. Measured values of dielectric parameters are optionally provided relative to characteristics (such as bias and/or jitter, for example) of a particular measurement circuit or system. Values provided by measurements should be understood to comprise dielectric properties, even if influenced by one or more sources of experimental error.

Measurement(s) during a cardiac treatment are potentially affected by the heartbeat (cardiac cycle), the respiration (respiratory cycle) and the rhythm(s) of the cardiac and/or respiratory cycles as well as other factors. Typically, data collected is assigned to an associated phase (e.g., a phase within the respiratory cycle or cardiac cycle) and/or condition of the heart (e.g. state of adrenergic stimulation, state post fast pacing, state post infusion of volume of saline, etc.) for correctly mapping the heart.

For example, conventional technologies use cardiac gating to collect data acquired from a roving catheter only at a specific point in the cardiac cycle (e.g. during an R wave of the body surface ECG—denoting the ventricular activation). The gating creates a data set, R-wave gated in this example, which is a sub-set of a complete data set that was potentially possible to acquire in the procedure. However, this gating algorithm has a limitation of potentially not gathering or not using of most of the data acquired (the non R-wave gate(s)). Similarly, a method that gates respiration by using a trigger that identifies a repetitive discrete indication of the respiratory cycle (beginning of inspiration for example), will improve usability of data acquired but will reduce even further the size of a useable data set for purpose of accurate construction of a model. Conventional technologies for data gating may potentially reduce the size of the useable data even more when they require simultaneous gating of more than one periodic cycle (e.g. cardiac and respiration).

To overcome such a limitation, conventional technologies sometimes widen the time window during which data is acquired and is used for construction of a model of a heart structure. By widening the time window, these technologies potentially reduce significantly the quality (sharpness, clarity, etc.) of a composed image.

Furthermore, conventional technologies may face a problem when attempting to compose an image or construct a model of a chamber when the chamber is operating at rhythms additional to the respiratory and cardiac rhythms that are to be accounted for when composing the image. Such rhythms include, for example, rhythms during various cardiac states such as during an arrhythmia, atrial fibrillation, ventricular fibrillation (VF); and during modes of cardiac activation (e.g. pacing), drugs, etc.

An aspect of some embodiments of the invention relates to transforming medical data captured under different circumstances to a common framework, registered to a common coordinate system.

In the present specification and claims, the term model is used to describe a set of structural features and spatial relationships between them. For example, in some embodiments, a structural feature that appears in a source image or model at certain spatial relationships to other features, is transformed to appear in a target image in the same spatial relationship to the other features, as the feature appeared in the source image.

For example, if a feature appears in the source image at halfway between the lower and upper left pulmonary vein ostia, or approximately there, after a transformation into a common framework in a target image, the feature will appear in the target image half way between the lower and upper left pulmonary vein ostia or approximately there. This will still be the case even if the distance between the lower and upper left pulmonary vein ostia is substantially different between the source image and the target image.

In some embodiments, such a transformation is achieved by registering the source image to the target image. In some embodiments the registration includes finding an optimal transformation between the features that appear in the source image and the features that appear in the target image. Optionally, the transformation is "optimal" in the sense that the transformation minimizes a predetermined cost function, which penalizes for unwanted characteristics of the transformation. In some embodiments, the transformation minimizes a cost function having a term that penalizes more heavily the larger an unwanted characteristic of the transformation becomes.

One such unwanted characteristic may be a large misfit. Misfit may be defined as a parameter indicative of the difference between features on the target image and features on the transformed source image, and may be quantitatively measured by a mean square of differences between locations of transformed features and locations of the same features in the target image. That is, if after transformation the features in the two images perfectly overlap, the misfit is minimal, and the misfit increases as differences between features in the target image and the transformed source image increase. Thus, an optimal transformation may be found by searching for a transformation that minimizes a cost function that panelizes for misfit. In some embodiments, the misfit penalty may be the only penalty term in the cost function. Alternatively, the cost function may include a plurality of penalty terms, in which case, the misfit is usually one of the penalty terms.

Another unwanted characteristic of a transformation may be spatial incoherence. Spatially incoherent transformation transforms nearby features in the source image to far apart features in the target image. Spatially coherent transformation, on the other hand, transforms nearby features in the source image to nearby features in the target image, and features that are far apart from each other in the source image—to features far apart from each other on the target image. Optionally, the distances are measured using units of the above-mentioned coordinate system, for instance, in units of a distance between two features, like between the two ostia in the above example.

Thus, in some exemplary embodiments, an optimal transformation may be found by searching for a transformation that minimizes a cost function that penalizes for spatial incoherence.

In some embodiments, a probe that measures a structure of the body organ moves in respect to the body organ. For example, the probe may be a catheter that moves inside a blood vessel to be modeled. In some embodiments, the probe may be stationary in the heart, and the heart may move in respect to the probe, expanding and contracting in accordance with the cardiac cycle. In some embodiments, the probe may move inside a beating heart. In all the above examples, the movement between the organ and the probe may cause the probe to measure different portions of the body organ at different times. Often, the body organ portions measured at the different times partially overlap with each other. The data received from the probe may be binned according to the time at which the data was gathered, for example, in bins of 0.1 sec, 0.5 sec, 1 sec, 5 seconds, 10 seconds, or any other time window. In some embodiments, sequential time windows may overlap, for example, the first bin may include data collected through seconds 0 to 10, the second bin may include data collected through seconds 3 to 13, etc. In some embodiments, every two sequential time windows partially overlap with each other.

In some embodiments, each bin of data may be used to form an image, by any method known as such in the field, for example, in the manner described in International Publication of PCT Application WO 2018/130974, the content of which is incorporated by reference herein in its entirety. The images may be registered to one another, as described below.

The images are registered to one another, so that at an end of a registration process, some or all the features that appear in the source images, including features that appear only in one or some of the source images, are included in a target image, and appear in the target image retaining their spatial relationships to other features in the modeled body organ portion. In some embodiments some measure of the differences between spatial relationships in the source image and the target image is minimized. The measure may be, for example, a mean square of the differences.

In some embodiments, a sequence of the source images is transformed and combined into a single combined target image by a sequence of transformations. Each transformation in the sequence of transformations may transform an associated image in the sequence of the images. In some embodiments, the sequence of transformations is required to be temporally coherent. In this context, temporal coherency of a sequence of transformations is achieved if each transformation continues a trend of the previous transformation. For example, a point that is displaced in a certain direction by one transformation is displaced in a similar direction by the next transformation in the sequence. One non-limiting exemplary method to ensure that a set of transformations is temporally coherent is by verifying that a transformation obtained by subtracting any one of the transformations in the sequence from the one before (or after) it in the sequence, is spatially coherent.

Thus, in some embodiments, a sequence of transformations is defined by searching for a sequence of transformations which minimizes a cost function that penalizes for temporal incoherence. Such a penalty may be in addition to a penalty on spatial incoherence of each of the transformations in the sequence.

In some embodiments, the movement of the body part in respect to the probe is periodic. For example, the cardiac cycle and the respiratory cycle may each introduce a periodic movement between a probe and a body organ, e.g., the heart. As in each period the heart may go through the same stages (at least when the cardiac cycle is normal), it is reasonable to expect that images of the same body organ portion, taken at the same phase of the cycle, should be substantially the same. Therefore, in some embodiments, the source images and the transformations are ordered in accordance with their position on the cardiac cycle (also referred to as cardiac phase) and/or their position on the respiratory cycle (also referred to as respiratory phase). The ordering potentially enables combining source images taken during different heart beats into a combined target image, potentially maintaining the spatial relationships between the features in the different images.

In some cases, the movement of the body part changes rhythm, for example, a heart can change its beating rate, from beating at a first sinusoidal rate to beating at a second sinusoidal rate, or to atrial fibrillation. In some embodiments, each such mode of movement (e.g., the first rate, the second rate, and the atrial fibrillation), is treated separately. That is, a plurality of images is taken from each movement mode separately, and a separate combined image is generated for each mode. Optionally, the combined images may be further combined with each other to a single combined image, e.g., by conventional registration methods.

In some embodiments, a sequence of single, combined, images is formed and presented as a movie, with each image in the single being a frame in the movie. In some such embodiments, each frame in the movie is a combined image obtained by transforming and combining the very same set of images. Preferably, the images are constructed from data bins of measurements, each measured within a specific time window, with a substantial overlap between time windows. The larger is the overlap, the smoother a movement seen in the movie. For example, each of the time windows may have 90% overlap with a preceding time window in the sequence and with a subsequent time window in the sequence. For example, the time window of the first bin may be between 0 and 100 msec; the next: between 10 and 110 msec; the next between 20 and 120 msec, etc. Images formed from each data bin, that is, each time window, are optionally registered to one of the images, referred to herein as a master-image, by a sequence of temporally coherent transformations. For example, if image #1 is the master image, the sequence of transformations register image #2 to image #1, image #3 to image #1, image #4 to image #1, etc. All the transformed images are optionally combined to a single image, referred to herein as frame #1.

In some embodiments, the same process is repeated with image #2 as the master-image, to form frame #2. When all the frames are ready, they may be displayed as a movie. It was found that such a movie describes the movement that the heart underwent when the data was collected. Each frame in movie prepared this way may be based on the same information, except for having a different image as the master-image.

In some embodiments, a bin of data is treated as if it forms an image. For example, each data point in the bin representing values of measurements in a measurement space may be linearly transformed to form an image. For example, in some embodiments, voltage values of one, two, three electromagnetic fields, or even more, are optionally measured, simultaneously. In some embodiments each electromagnetic field being characterized by a different frequency. A data point in the bin may be a set of three voltage values, simultaneously measured at the three frequencies. An image of the data in the data bin may include points shown on a Cartesian coordinate system. In some embodiments the length of the axes may be, for example 1 cm (or some other length) for each measured mV. In such embodiments, after the images are registered and combined as described above, the obtained combined image may be used to form an image in real space (rather than in measurement space), by any way known as such in the field, for example, in the method described in the above-mentioned PCT Application WO 2018/130974.

In some embodiments, the above-mentioned image may be a point cloud. In some embodiments, point clouds (in measurement space or in real space) from different data bins are transformed and combined to obtain a single combined point cloud, and the combined point cloud is then optionally used to reconstruct an image in which the points are connected, e.g., by a smooth surface. The reconstruction may be by any method known as such in the field for constructing images from point clouds, for example, by using a ball pivoting algorithm.

In some embodiments, an image of a received sequence of images includes an indication of where a certain predefined region is present in the image. For example, in an embodiment where the imaged body part is the right atrium, data points corresponding to the fossa ovalis may be marked on each of the images of the sequence. In such embodiments, a search may be for a sequence of transformations that transform marked regions (i.e., regions defined by marked data points) in source images, to marked regions in a target image. A requirement for transforming marked regions to marked regions may expedite the search for the transformations. Similarly, in some embodiments, a physician keeps the probe steady at one point for one or more sequential periods of movement of the body part (e.g., the probe may be pushed against an arbitrary point on the heart wall for several heart beats). Readings of the same values during several periods may be marked, and such marking may be used for defining a sequence of transformations that transform the marked regions to marked regions, expediting the search for an adequate sequence of transformations.

In some embodiments the common framework is a common geometric, spatial framework, where data points include geometric locations using a common spatial coordinate system. For example, in some embodiments when locations of electric measurements such as voltage measurements are known, the locations may use a common spatial coordinate system, for example measured in units of distance relative to some origin location in space.

In some embodiments the common coordinate system includes a common temporal coordinate, where data points include temporal location described in the common temporal coordinate. By way of a non-limiting example, electric values measured during two different cardiac cycles may be combined into one data set based on their temporal coordinates, such as a time along a cardiac contraction cycle or phase of the cardiac contraction cycle. By way of a non-limiting example, electric values measured during movement of a probe along an artery may be combined into one data set based on their temporal coordinates, that is, time measured since a specific time origin. In some embodiments the data from the different circumstances is used to produce an image, based on having the common geometric and/or temporal coordinate systems. Different circumstances optionally include different cardiac pulse phases, different cardiac pulse pathologies, different breathing phases, and different breathing rates. Many times using different coordinate systems affects measured values.

An example scenario of medical data captured under different circumstances is described below. The scenario is not intended to limit the scope of the invention, but to explain the issue of capturing medical data under different circumstances. Persons skilled in the art are able to understand the application of the example under additional scenarios.

When collecting medical data, by way of a non-limiting example in a living, breathing patient, the patient or portions of the patient for which the medical data is collected, may be moving. In many cases the medical data acquires different values when the patient is moving; breathing; his heart is beating, and so on.

Collecting medical data may include, by way of a non-limiting example, measuring one or more electrical readings, for example: (optionally simultaneous) electric voltage readings or electric field readings in an intra-body probe or catheter. In some embodiments, the probe includes several electrodes, and provides several simultaneous measurements. As used herein, "electrical readings" are interchangeable with "electric measurements" and represent direct electrical measurements such as voltage and current, as well as values calculated based on the direct electrical measurements such as impedance (electric) and other electric and/or dielectric parameters. Collecting medical data may also include non-electrical readings, by way of some non-limiting examples magnetic readings, location data, pH data.

As used herein, electric measurements may include any measured electric parameters and/or dielectric parameters, either directly measured or calculated from the measured parameters, for example: voltage, current, conductivity, resistivity, reactance, admittance, etc. Electric measurements may be obtained by one or more electrodes, which may be carried, for example, on an intra-body probe; for example an ablation catheter; a split tip catheter; a balloon catheter; a coronary sinus catheter, a lasso catheter, a multi-prong catheter; a basket catheter Optionally, each such probe may carry one or more, for example 2, 3, 4, 10 or 20 electrodes. In some embodiments, the electrodes may include electrodes outside the body, for example, ECG body surface leads; body-surface patch electrodes, etc.

Electric and dielectric measurements may be obtained by one or more electrodes provided on an ablating catheter. Electric measurements may be obtained by one or more sensors provided on a dedicated intra-body probe, e.g., used solely for such electric measurements. Electric measurements may be obtained at a single frequency or at a plurality of frequencies. In some embodiments, electric measurements include measurement at various frequencies, e.g., from about 10 kHz to about 1 MHz. In some embodiments, electric measurements may include complex values. In some embodiments, electric measurements may include impedance measurements including measurements of impedance between different electrodes on the ablation catheter (e.g., between a tip electrode on a probe of the ablation catheter and another electrode on the same catheter), between one or more electrodes on the ablation catheter and one or more electrodes on another catheter, and/or between one of more of the ablation electrodes and one or more body surface electrodes.

Collecting the medical data may include, by way of a non-limiting example, measuring one or more simultaneous electric voltage readings or electric field readings from an external electrode placed on a patient's body. In some embodiments, several electrodes are placed on the patient's body, and optionally provide several simultaneous measurements.

By way of a non-limiting example, in cardiac imaging, a heart changes shape over a heartbeat. In fact, many patients' hearts may change shape differently in case of different types of heartbeat. A heartbeat which exhibits atrial fibrillation changes a shape of a heart differently, and may develop differently over time, than a heartbeat which does not exhibit atrial fibrillation.

In some methods of collecting medical data, one uses gating to compensate for heart beat and respiration. In such methods, medical data is captured, or used, only when the medical data is within a specific gate of time during which the data does not change much. Medical data outside the specific gate of time is either not captured, or, if captured, not used together with data from another timing gate.

However, not using medical data from different gates of time means using less data. By way of a non-limiting example, using less data may cause a loss in resolution of a medical image, and/or a loss in accuracy, and/or not imaging a portion of a desired image, and/or taking more time to produce a desired image.

By way of a non-limiting example, when using intra-body electrical readings to construct an anatomical structure of a heart, one or both of an intra-body electric probe and the heart are moving, and data captured may pertain to different portions of a heart at different times. Constructing anatomical structure of a heart is described, for example, in above-mentioned PCT Application WO 2018/130974.

By way of a non-limiting example a scenario as described in the above paragraph may use 6-8 time windows to bin data for movement over a heartbeat cycle, and 4-6 gates to bin data for movement over a breathing cycle. Using medical data from just one heartbeat data bin or breathing data bin means leaving some or even most of the collected data unused.

In some embodiments data is not necessarily binned. In some such embodiments, each data point has associated with it a phase indicator, which may include values indicative of time the data point was captured from beginning of heartbeat cycle and/or phase of heartbeat cycle at which the data point was captured, and/or time from beginning of breathing cycle to the capture of the data point and/or phase of breathing cycle at which the data point was captured. The value is optionally used to transform data points to share a common temporal coordinate system, that is, to refer to a common time of beginning of the heartbeat cycle. In some embodiments the value is optionally used to group data points with similar values to be transformed together without data points being divided or stored into actual data bins.

If no data gating or binning is used, images (e.g., heart image or portions thereof) generated using data from different cardiac contraction phases and/or different respiratory phases may cause blurring of the images.

In cardiac electrophysiology (EP) medical procedures, acquisition of electrical readings and/or medical data can extend over several seconds, several minutes, and even several hours. In such cases a cardiac image may be updated, for example during the medical procedure; such that new data may be collected and calculated 'offline' to create a new or updated image; e.g. to compensate for changes during the procedure. Furthermore, patients may be suffering from cardiac arrhythmias; and during the procedure the patients' hearts may switch between different rhythms, many of the rhythms presenting a different shape for different data bins when compared to a shape of a heart in normal rhythm. Therefore, heart maps or images produced during EP procedures may be misleading as they may contain information acquired during one heart rhythm which has little resemblance to another rhythm during which an operator currently navigates in a heart.

Some challenges that are faced when imaging a heart with a roving catheter are:

a. The heart beats—the heart shape and size changes its geometry during the cardiac cycle and the heart electrical properties;

b. The patient breathes—which changes the geometry of the heart and electrical properties of the chest during the breathing cycle;

c. The heart can change its activation and contraction (activation pattern—causing the contraction pattern).

An aspect of some embodiments of the invention relates to transforming data (e.g., electrical readings) obtained from an intra-body probe to use a common coordinate system in order to use the data to image anatomical structure. Example scenarios of the transforming are described herein. The scenarios are not intended to limit an extent of the concept of transforming of medical data captured under different circumstances to use a common coordinate system, but to explain. Persons skilled in the art are able to understand the transformation for additional scenarios.

According to some embodiments of this invention, medical data from more than one bin is used to create an image.

In some embodiments, medical data from one data bin is transformed, and the transformed data is combined with medical data of a second data bin. The combined data is optionally used to create an image. The image may be a static image or a dynamic image.

In some embodiments, the image is optionally dynamically updated during a medical procedure, producing a dynamic, potentially changing and/or updating image.

In some embodiments, new medical data is optionally collected and calculated to produce a new static image.

In some embodiments, medical data is optionally collected for many or even all data bins and is optionally transformed to maintain a correspondence between data from different data bins, such transformation of data from one data bin to another is termed herein "gate projection".

An aspect of some embodiments of the invention relates to means and methods for synthesis of an image originating from data from multiple data bins in a phase and/or state corrected manner.

In some embodiments, the medical data of each bin potentially corresponds to data suitable for synthesizing multiple, potentially co-located images. In some embodiments the multiple images are separate discrete images.

An aspect of the invention relates to a method to use all or a majority of data (e.g., medical data) acquired while imaging or mapping the heart with a roving catheter. The roving catheter data acquisition potentially creates a sparse data set which means that in part of the locations that the catheter visits the catheter collects data that was captured at a different phase or mode of a breathing cycle, or a different mode of a cardiac cycle.

In some embodiments of the invention, a method is used to project, based on producing a transformation, data from several bins into one existing bin or one new bin which serves as a common reference bin, and use more of the data that was acquired, and in some embodiments all of the data that was acquired.

It is noted that medical data may have various dimensions, for example time, location, cardiac cycle phase, pressure phase, temperature, and a phase in the breathing cycle.

An aspect of some embodiments of the invention relates to producing a transformation of data that transforms data from one data bin to another data bin within a same dimension, and transforms data from one data bin to another between dimensions. In some embodiments, the transformation is a rigid transformation of some or all of the data from one data bin to another data bin.

By way of a non-limiting example, a location of a catheter is known based on at least two points during a cardiac cycle, a transformation is optionally produced that accepts a phase of the cardiac cycle and provides a location of the roving catheter at that phase.

In some embodiments, the transformation operates on a multi-dimensional sparse matrix of acquired data.

In some embodiments, the transformation generates an optimal transformation within each of the dimensions.

In some embodiments, the transformation generates a transformation which in some embodiments, the transformation generates an optimal transformation within each of the dimensions. In some embodiments an image is produced by using transformed data. In some embodiments, the transformation generates an optimal transformation within each of the dimensions.

In some embodiments, an optimal transformation is optionally generated within all or part of the dimensions simultaneously.

In some embodiments, the transformation is applied to the sparse matrix and optionally fills in missing data by interpolation.

In some embodiments, the data populates a multi-dimensional matrix. For example, each type of measurement is optionally a dimension, and/or different bins may optionally be defined as dimensions of a measurement. In some embodiments, when projecting from a multidimensional matrix to a specific point in the cardiac cycle a reduction of at least one dimension in dimensionality of the data is achieved, by eliminating the cardiac cycle dimension.

In some embodiments, the projection is used to reduce one or more dimensions of the multi dimension data.

In some embodiments, the projection is used to transform data to share a common geometric coordinate system, optionally transforming geometric coordinates associated with data points of a data bin to have a same geometric coordinate system as data points of another data bin.

In some embodiments, the projection is used to transform data to share a common temporal coordinate system, optionally transforming time measurements associated with data points of a data bin to have a same temporal coordinate system as data points of another data bin. By way of a non-limiting example, data points captured during different heartbeats may optionally be transformed to be associated with duration since a beginning of a heartbeat rather than clock time. By way of another non-limiting example, data points captured during different breathing cycles may optionally be transformed to be associated with duration since a beginning of a breathing cycle rather than clock time.

The term "sparse data set" in all its grammatical forms is used throughout the present specification and claims to mean a data set in a data bin in which the ratio of filled to empty spaces is low. By way of a non-limiting example, for a given spatial resolution, the data set is sparse when entries for some locations in the second data bin are missing from the first data bin.

In some embodiments, temporal coherence facilitates a search for correspondence between extremely sparse (and potentially disjoint) data sets.

Figure 1:
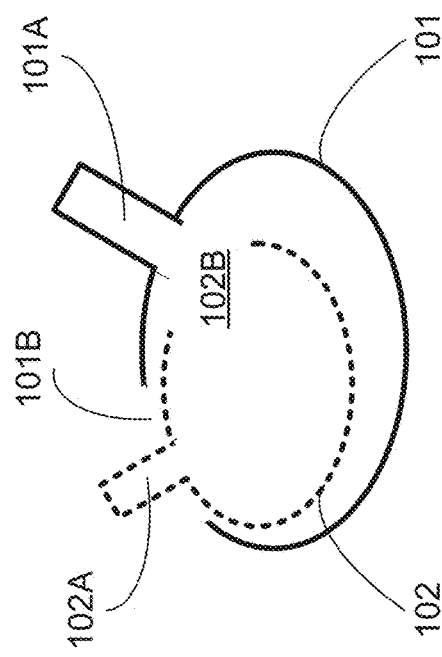
FIG. 1 is a simplified line drawing illustration of images produced of a portion of a heart at two time points according to a prior art method of imaging.

For purposes of better understanding some embodiments of the present invention, reference is first made to FIG. 1, which is a simplified line drawing illustration of images produced of a portion of a heart at two time points according to a prior art method of imaging.

FIG. 1 illustrates a problem with imaging the heart when the heart is moving due to breathing, changing size and shape due to the heart beating, and optionally using an imaging modality which does not necessarily capture an entire image of the heart at one point in time.

FIG. 1 shows a first line drawing illustration of an example first image 101 of a portion of a heart, for example an atrium, at a first point in time, and a second line drawing illustration of an example second image 102 of the very same heart atrium at a second point in time.

The first image 101 is shown larger than the second image 102, to illustrate that the atrium may have contracted at the second point in time. The first image 101 is shown shifted in space relative to the second image 102, to illustrate that the atrium may have moved within the patient's chest, possibly due to breathing, between the first point in time and the second point in time.

By way of a non-limiting example, the first image 101 is shown displaying a section 101A which the second image 102 does not display, and not displaying a section 101B which the second image 102 does display. The second image 102 is shown displaying a section 102A which the first image 101 does not display, and not displaying a section 102B which the first image 101 does display.

FIG. 1 shows images of the atrium during points in time T0 and T1.

Data for producing the image 101 may have been captured when an intra-body probe was in a position to capture data for the section 101A, and not capture data for the section 101B, and similarly for data for producing the image 102.

In prior art imaging, the difference in dimensions such as shape, size, physical location in space between the first image 101 and the second image 102 would cause the data for producing the second image 102 to be unused, so as not to attempt to produce a combined image which is smeared or distorted, resulting in a smeared image. Combining data from time T1 to data from time T0 would potentially distort and/or blur the combined image.

Data captured under different conditions, for example at different times, is sometimes kept separate, and the separation is sometimes termed "gating" or "binning".

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In some embodiments of the invention, data for producing the second image 102 is optionally transformed by registering to the first image 101. In some embodiments, the transform is by a transformation based on portions of the anatomical features common to both the first image 101 and the second image 102.

In some embodiments, the transformation is based on all the portions of both images. In some such embodiments the transformation is performed without first identifying common portions in both images.

In some embodiments the transformation is optionally a rigid transformation of some or all of the data points associated with anatomical features in the second image 102 which are common to the first and second images.

Optionally, the transformation, rigid or not, is determined so that a good fit is achieved of an image or mapping of the data points in the second image 102 which are common to the first image 101. Some non-limiting examples of what is optionally considered good fit include: small misfit between features in the image obtained by transforming image 102 and in image 101; spatial coherence of the transformation; a smoothness of a shape of an object imaged by the transformed data points; a correct or approximately correct volume of an object imaged by the transformed data points; a number and/or size and/or relative location of fixed anatomical structures (e.g. veins, arteries, valves) in an image which was produced by the transformed data points; and fulfilling expectations of an expected change to an anatomical structure due to an altered rate or rhythm—for example, a size of a chamber is typically smaller at higher cardiac rates, the size of the chamber is typically larger during fibrillation.

In some embodiments, the transformation is optionally a rigid transformation of some or all of the data points associated with anatomical features in the second image 102 which are common to the first image 101 and the second image 102.

In some embodiments a transformation is optionally an affine transformation that minimizes displacement between a transformed shape and a target shape and/or transformed points and a target shape.

Figure 2:
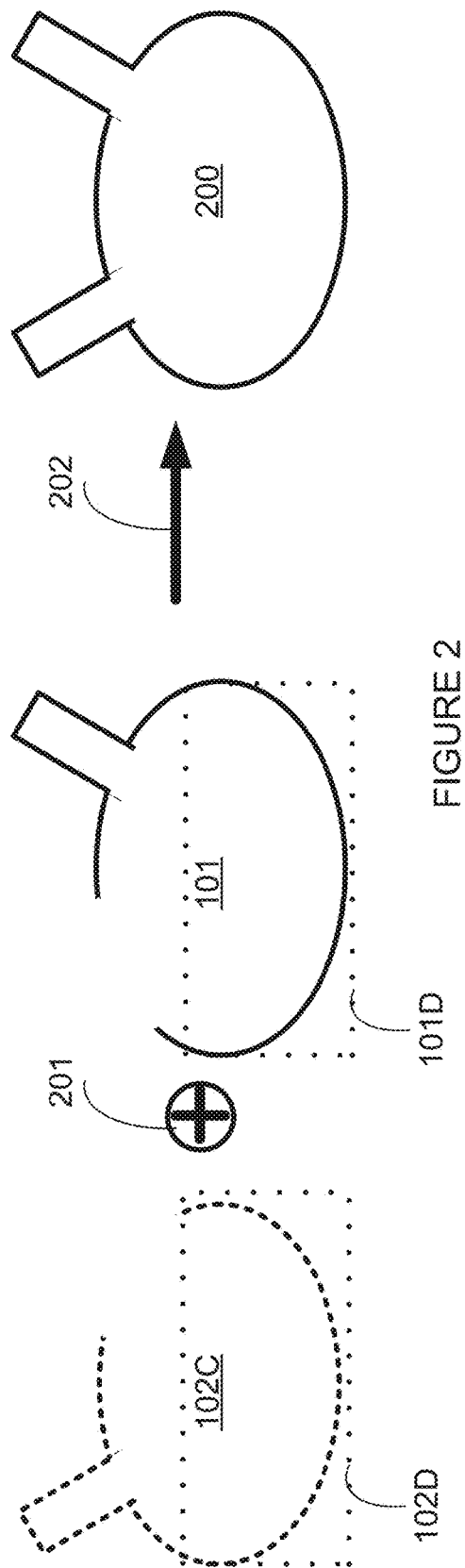
FIG. 2 is a simplified line drawing illustration of transforming data points from one data bin to another data bin, and using data points from both data bins to produce an image, according to some embodiments of the invention.

Reference is now made to FIG. 2, which is a simplified line drawing illustration of transforming data points from one data bin to another data bin, and using data points from both data bins to produce an image, according to some embodiments of the invention.

FIG. 2 shows a first line drawing illustration of the example first image 101 as described above with reference to FIG. 1, and a second line drawing illustration of an example second image 102C. The second image 102C is optionally produced based on the second image 102 described above with reference to FIG. 1, which has been transformed by a resizing transformation and/or a rotation transformation and/or a shifting transformation, so that at least a portion 102D is transformed by a transformation T to correspond to a portion 101D of the first image 101.

FIG. 2 shows a third line drawing illustration 200 produced 202 by combining 201 the example first image 101 and the second image 102C.

A transformation which transforms data points from one data bin, for example that used to produce the second image 102 of FIG. 1, to a transformed set of data points, for example that used to produce the second image 102C of FIG. 2, is termed herein "gate projection" and "bin projection".

Collecting Data

In some embodiments medical data is received. Some data is physical data, such as time and location/space measurements. Some data is processed data, such as a decision whether a data point belongs to an ECG measurement of a chaotic heartbeat or a non-chaotic heartbeat.

In some embodiments receiving the data is practically continuous, such as time and location/space measurements. In such cases actual measured values may be recorded even if the values are eventually collected into bins, such as time-window bins.

Binning Data

In some embodiments medical data is arranged in time domain data bins, that is, data measured at different times is arranged according to the time the data was collected, optionally in time windows. In some embodiments, the data arranged in time domain data bins corresponds to a sequence of images, or movie frames.

In some embodiments Electro-Cardio-Gram (ECG) measurements are gated or binned based on belonging to an identified phase in the cardiac rhythm—e.g. binned according to one or more of: P segment, PR interval, PR segment, Q, R, S, QRS complex, ST segment, QT interval, and T.

In some embodiments, measurements indicative of the structure of the body part to be imaged are gated or binned according to an identified phase in the cardiac rhythm, during which the measurement were taken. Optionally, measurements taken during different phases are used to produce different single images. The single image of a cardiac phase may be generated from images based on measurements made during a plurality of time windows, all within the same phase, even if not of the same cycle. For example, data from the P segment (or any other segment) of one heartbeat may be binned into the same bin, and used to generate a same source image, as the P segment of another heartbeat (e.g., a sequential heartbeat). In some embodiments, the source images are ordered in the sequence according to their phase in a cycle of the periodic change that the imaged body part undergoes, for example, according to their phase in heartbeat.

In some embodiments, after a single image is generated for each of two or more phases, the single images are registered to each other and combined to provide a combined image showing details observed during different phases.

In some embodiments ECG measurements are optionally binned to one or more data bins belonging to a normal rhythm (e.g., sinusoidal) and to one or more data bins belonging to an abnormal rhythm (e.g., atrial fibrillation). Similarly to the above, data measured during a normal rhythm may be binned separately than data measured during an abnormal rhythm, and a different single image may be generated for each rhythm type.

In some embodiments ECG measurements are optionally binned to one or more data bins belonging to a cardiac rhythm types including: a chaotic beat; an atrial fibrillation beat; a first type of dominant beat; a second type of dominant beat; and a third type of dominant beat.

In some embodiments, dominance of a beat is based on a ratio of beats that belong to a specific rhythm or form, where form is a type of beat, such as sinus beat, atrial premature beat, ventricular premature beat, post premature beat, bigeminy, blocked beat, etc. Measurements made during different types of dominant beats may be binned to different data bins.

In some embodiments ECG measurements are optionally processed to identify R-wave in the ECG measurements. The ECG measurements are optionally evaluated from time points starting at the R-wave, whether a heartbeat belongs to a chaotic heart rhythm or a normal heart rhythm. In some embodiments if a heartbeat belongs to a chaotic heart rhythm, such as, by way of some non-limiting examples, an atrial fibrillation (AF) rhythm and some premature beats, measurements belonging to the chaotic heartbeat are optionally binned in a "chaotic" data bin.

In some embodiments if a heartbeat does not belong to a chaotic heart rhythm, measurements belonging to the non-AF heartbeat are optionally additionally processed, and additional segmentation of the beats in the non-AF rhythm is optionally performed. In some embodiments a covariance-based classifier is optionally used to select three classes of non-AF heart beats. A first type of dominant beats are optionally binned to a first bin, for example termed bin A, and a second type of dominant beats to a second bin, for example termed bin B, and other non-AF beats are optionally binned to a third bin, for example termed bin C.

In some embodiments, measurements are binned based on their phase within a breathing cycle, where each measurement is binned according to a breathing phase in which the measurement was taken. In some embodiments phases in a breathing cycle may be identified based on body-surface impedance measurements.

In some embodiments body-surface impedance measurements are gated or binned based on belonging to an identified phase in a breathing rhythm.

In some embodiments a signal from body-surface impedance is optionally processed to identify phases in a breathing cycle.

Alternatively or additionally, measurements may be binned according to the breathing cycle during which they were measured, without relation to breathing phase. For example, a cycle may be identified and binned to a number of bins of equal duration (e.g., of 0.1 second, 0.5 second, 0.8 second, 1 second, 3 seconds, 6 seconds, 10 seconds, 20 seconds, or intermediate number of seconds).

In some embodiments peak detection in a signal of a sensor measuring breathing is optionally performed to identify a start of a breathing cycle (BB), defined as time between consecutive breaths. An exemplary method for detecting breathing peaks may be found in the article "A robust detection algorithm to identify breathing peaks in respiration signals from spontaneously breathing subjects", published in 2015 Computing in Cardiology Conference, DOI: 10.1109/CIC.2015.7408645, the disclosure of which is incorporated herein by reference.

In some embodiments a covariance classifier is used to segment BB signals into a first data bin, e.g. breathing bin A, for base respirations, a second data bin, e.g. bin B, for short breathing cycles, and a third data bin, e.g. bin C, for long, for example sigh-type, breathing cycles.

Reference is now made to FIG. 3A, which is a simplified block diagram illustration of a system for measuring medical data, classifying and/or binning the medical data, and transforming the medical data to use a common coordinate system according to some embodiments of the invention.

FIG. 3A shows components in a system 311 constructed according to an exemplary embodiment of the invention.

The system optionally includes one or more measurement component(s) 312 for collecting measurements 310 from a patient's body. Measurement components 312 may include, for example, body surface electrodes and/or intra-body electrodes. The measurements optionally include patient-related signals with information regarding one or more periodic signals, for example body surface ECG or intra-cardiac electrograms, chest wall dimension, and optional physical measurements such as time, location in space (e.g., of the intra-body electrodes), temperature (e.g., in vicinity to an ablation site), pressure (e.g., of a catheter against a tissue or blood pressure measured by a sensor on a catheter) and so on.

In some embodiments, measurement component(s) 312 may not be part of system 311, and the measurements may be otherwise provided to system 311, e.g. through one or more interfaces connecting external measurement components to processing component 316 and/or projecting component 320.

An output 314 of the measurement component(s) 312 is optionally a signal and/or digital data which is affected by a patient's physiology, for example a body-surface ECG, data of occurrence times of R waves, data of the occurrence times of initiation of respiration, body surface impedance (optionally continuous), instantaneous heart rate, amplitude of respiration, $CO_2$ content or concentration in the breath, acoustic signal of the chest, etc.

The output 314 optionally serves as input to a processing component 316 which may be, for example, a computer or a central processing unit. Thus, output 314 may also be referred to as input 314.

In some embodiments, processing component 316 receives output 314 of the measurement component(s) 312 in units of voltage, and calculates values of resistivity, reactance, or other dielectric properties based on the voltage. The values may optionally include a discrete time series of values measured during one or more rhythms, and/or analog values in a continuous measure of the rhythm, for example a blood pressure wave, nasal airflow, etc.

The processing component 316 optionally calculates one or more classification values associated with one or more rhythms in patient's physiology and/or associated with different stages in the rhythms. Such associated classification values may be referred to herein as descriptors.

In some embodiments, the processing component 316 receives output 314 of the measurement component(s) 312, and calculates whether the electric signal corresponds to a sinus cardiac rhythm or to an arrhythmia based on the voltage values, and/or a phase of cardiac rhythm to the received output. In some embodiments, processing component 316 may calculate its output based on a time that elapsed from a beginning of the cardiac rhythm. Optionally, the beginning of the cardiac rhythm is also detected by the processing component based on data input 314.

In some embodiments, the processing component 316 optionally processes separately data collected in different states. The different states may include, for example, normal heart beating or arrhythmia, such as atrial fibrillation. Different states may also be different types of breathing, such as calm breathing, strenuous breathing, shallow breathing, deep breathing, etc. For this end, in some embodiments, the processing component 316 optionally produces a classification of a physiological state (e.g. sinus cardiac rhythm or arrhythmia, normal breathing or strenuous breathing, atrial fibrillation or ventricular fibrillation, etc.) associated with the data input 314, such that data collected in a given state is optionally processed separately from data collected in other states.

In some embodiments the state classification may be input into the processing component 316 from the measurement component 312 or electronically fed directly to the processing component 316.

In some embodiments, state classification is optionally generated in the processing component 316 to classify a continuous signal associated with the state.

Processing component 316 outputs an output 318 in the form of data (e.g., in case output 318 is digital) or a signal (e.g., in case output 318 is analog). Output 318 is optionally input to a projecting component 320. In some embodiments, the projecting component 320 may be part of the processing component 316.

In some embodiments, projecting component 320 and/or processing component 316 may be configured to implement methods described in reference to FIGS. 4A, 4B, 5A, 5B, 6A-6D, 10A-10B, 11A-11C, 12 and 13.

In some embodiments, processing component 316 optionally classifies the output 314 as belonging to a specific state, such as output indicative of measurements performed during a specific state of rhythmic change, such as change in heartbeat rate, type of heart rhythm—sinus, arrhythmic, type of breathing—shallow or deep, and so on.

In some embodiments input to the projecting component 320 may optionally also include input from one or more electrodes (not illustrated) optionally from an intra-body probe, optionally collecting data for building a map of a heart chamber, including, by way of a non-limiting example, instantaneous locations, voltages, impedances etc., as well as the output from the processing component 316.

In some embodiments, measurement component(s) 312 may be configured to measure electrical readings or other medical data. Measurement component(s) 312 may include one or more electrodes and/or one or more sensors provided, for example, on an ablating catheter. Output 314 of the measurement component(s) 312 is optionally a signal and/or digital data which includes electrical readings and/or other medical data.

In some embodiments, projecting component 320 accepts as input 318 raw data signals measured during brief overlapping time windows, the time windows optionally having a duration shorter than 5 msec, 10 msec, 50 msec, 100 msec, 250 msec 500 msec, 1 sec, 5 sec, 10 sec 20 sec or 30 sec. The projecting component 320 optionally transforms the overlapping data sequences (fragments) so that the overlapping time windows are transformed to coincide with each other. In some embodiments, some or even all of the data in the time windows of input 318 is transformed to produce data which describes a combined time period potentially extending longer than the separate time windows, and using a same time scale.

In some embodiments, the projecting component 320 optionally assigns correspondences between the overlapping segments (fragments), and optionally recovers a transformation that maps between the overlapping segments.

Qualitatively, a requirement that a transformation maintains spatial coherence may be understood as a requirement that the transformation displaces points that are near each other to new positions that are near each other, and points that are far from each other to new positions that are far from each other. The displacements of points that are near each other are thus along paths of similar directions and similar lengths. The further the points being transformed are from each other, their displacements may become less similar. An example of a registration algorithm designed to provide coherent transformation is the Coherent Point Drift (CPD) method, such as described in an article titled "Point Set Registration: Coherent Point Drift", published on 15 May 2009 on the world-wide-web, in arxiv(dot)org/abs/0905.2635, the disclosures of which is incorporated herein by reference.

Qualitatively, a requirement that a transformation maintains temporal coherence may be understood as a requirement that the transformation displaces data points along a sequence of time periods in a smooth manner.

One non-limiting exemplary method to obtain a spatially coherent transformation is to minimize a cost function, with less coherent transformations being assigned a higher cost. The coherence may be estimated, for example, by decomposing the transformation to its spatial frequency components, and associate a high cost for high frequency components.

One non-limiting exemplary method to obtain a temporally coherent sequence of transformations is to require spatial coherence from a difference between each two transformations that transform successive images. An alternative way to obtain temporally coherent transformation(s) is described in detail in the article "Registration of multiple temporally related point sets using a novel variant of the coherent point drift algorithm: application to coronary tree matching" published in Proc. of SPIE vol. 8669, incorporated herein by reference.

The term "adjacent" in all its grammatical forms is used throughout the present specification and claims to mean next to or adjoining something else, abutting, bordering (on), contiguous with, touching, having a common vertex or a common side.

In some embodiments, a variation of the CPD method is optionally used to calculate the correspondence between different values of the output 318 of the processing component. In some such embodiments, when the fragments overlap over a larger duration than the sampling rate, the method optionally connects fragments using the overlap to force a correct correspondence between fragments that are close to each other spatially and/or temporally. In some embodiments, the coherence is optionally applied in the spatial domain. In some embodiments the coherence is optionally applied in the temporal domain. In some embodiments, the coherence is optionally applied in both the spatial and the temporal domain.

A brief description of CPD is now provided. CPD refers to a family of methods, which can be used to solve a correspondence determination of sparse data matrices. Point set registration is a component in many computer vision tasks. A goal of point set registration is to assign correspondences between two sets of points and to recover a transformation which maps one point set to the other. Multiple factors, including an unknown rigid and/or non-rigid spatial transformation, a large dimensionality of a point set, noise and outliers, make point set registration a challenging problem.

In some embodiments, a probabilistic method, called a Coherent Point Drift (CPD) method, is introduced for both rigid and non-rigid point set registration. An alignment of two point sets is taken as a probability density estimation problem.

In some embodiments Gaussian Mixture Model (GMM) centroids are optionally fit, representing a first point set, to data (a second point set), by maximizing likelihood. The GMM centroids are optionally forced to move coherently as a group to preserve topological structure of the point sets.

In a rigid case, the coherence constraint is imposed by re-parametrization of the GMM centroid locations with rigid parameters, and a closed form solution of the maximization step of the EM algorithm in arbitrary dimensions is derived.

In a non-rigid case, the coherence constraint is optionally imposed by regularizing a displacement field and using variational calculus to derive an optimal transformation.

In some embodiments, a best-fit transformation is optionally used for rigid and/or non-rigid point set registration. An alignment of two point sets is taken as a best-fit estimation problem. In some embodiments best-fit is calculated based on minimizing a mean-square-error between corresponding points in a first data set projected onto a second data set. A best-fit transformation is termed herein a method which provides minimal mean-square-error between corresponding points in a first data set projected onto a second data set. The mean square error may also be referred to herein as one exemplary form of "misfit".

In some embodiments a fast algorithm is introduced that reduces the computation method complexity.

In some embodiments time complexity of the computation method is optionally reduced by using a small number of base functions to represent the transformation. The number of base functions can be smaller than the number of points being transformed, and produce smooth transformations.

In some embodiments the projecting component 320 produces a transformation vector. The transformation vector transforms one or more of locations of a roving catheter, time of measurement, relevant mapped properties such as measured electrical values or calculated values based on the measured values, to other locations, times of measurement and mapped properties.

In some embodiments the projecting component 320 accepts a phase during which values were measured, and optionally uses the transformation vector to calculate relevant mapped values.

In some embodiments the projecting component 320 provides a location of a same part of, for example, a heart chamber, later in a rhythmic movement. For example, one can provide input to the projecting component 320 of a location of the left atrial ridge (or some other site) that was acquired at a specific point in the cardiac cycle, and/or a specific point in the respiratory cycle, and/or during a specific heart rhythm, and the projecting component 320 uses the transformation to determine, and in some embodiments display, or "play", where the next locations of the left atrial ridge will be in following times. In some embodiments, the transformation is optionally used to make projections not only for a future location but for future relevant sensed properties such as electric measurements and/or dielectric measurements and/or anatomical structure shape extrapolation.

In some embodiments, the projecting component 320 produces an interpolator, optionally based on a transformation vector. In some embodiments the interpolator is a transformation which minimizes misfit, for example minimizes mean-square-error of differences between features on a target image and features on a transformed source image.

In some embodiments, the projecting component 320 uses the transformation vector to map data sets measured under different conditions, that is transform data values in the data sets, to each other; where the different conditions can be in a spatial domain, and/or temporal domain.

In some embodiments, the projecting component 320 makes use of consecutive, overlapping segmented data streams (e.g., electrical readings) acquired at a tip of a roving catheter. The data in the data streams describes, for example, consecutive locations of the tip of the roving catheter together with simultaneously recorded body-surface ECG and voltages measured inside a heart chamber, for example, in touch with a heart chamber wall. The data streams are optionally spliced in an overlapping manner to yield spliced sections that have a total duration of L msec. An operator is optionally navigating the catheter inside a heart chamber, and wishes to construct the shape of the chamber, for example, during an "end systole". The roving catheter visits at an "end systole" only a fraction of the time during which the catheter is roving within the heart chamber. According to an embodiment of the invention, the location of the roving catheter tip is optionally recorded together with the simultaneous body surface ECG. The recorded data stream is optionally segmented into consecutive L msec slices, for example 5 msec slices, every N msec, for example every 1 msec, such that consecutive slices have for example 4 msec of overlapping data. An ensemble of catheter tip locations at each point in the cardiac cycle, including the desired "end systole" point, provides a sparse set of data points.

In some embodiments, data measured at consecutive times, for example not at "end systole", are optionally mapped to yield a series of consecutive models, each modelling the heart chamber structure at a different, potentially close, point in time. A Coherent Point Drift (CPD) method is optionally applied to the consecutive partially overlapping models to register structure of the heart chamber at one time to its structure at another time. In some embodiments the transformation performs an extrapolation from a data point measured at one location in space and/or instant in time to another point close in space and/or time.

It is noted that data points captured at a specific instant may include multiple dimensions and/or variables. Some of the dimensions/variables may be continuous and some of the dimensions/variables discrete.

Gate projection, transforming data point values from one data bin to another data bin, or to a common reference bin, may optionally reduce a dimensionality of the data, in a sense that data which was captured at a point in time T, which may include N dimensions, for example 3 location dimensions, one time dimension, M voltage readings, and so on, be recorded as N-dimensional data, but after transformation, for example if all time-window bins are transformed into one time-window bin, the data dimensionality may be reduced, for example, by 1. In the above-mentioned non-limiting example the time dimension is eliminated from the data, as all data is transferred to a same time-window bin.

Reference is now made to FIG. 3B, which is a simplified block diagram illustration of a system for measuring medical data in several frameworks and transforming the medical data to use a common framework according to some embodiments of the invention.

FIG. 3B shows components in a system 391 constructed according to an exemplary embodiment of the invention.

FIG. 3B shows a system which accepts input of measurements 390 and does not include a processing component such as the processing component 316 of FIG. 3A. FIG. 3B does include a projecting component 396 to project at least some of the measurements from a first data bin to a second data bin. In some embodiments, a value describing which data bin the input measurements 390 belong to may be accepted together with the input measurements 390. In some embodiments, the data bin may be determined by the projecting component 396, for example by analyzing the accepted values. For example, electrical values may be classified to chaotic rhythms and sinusoidal rhythms by algorithms known in the field, for example, as described in the article titled "A real-time atrial fibrillation detection algorithm based on the instantaneous state of heart rate", PLoS ONE 10(9) e0136544, the contents of which is incorporated herein by reference.

The system 391 optionally includes one or more measurement component(s) 392 for collecting measurements 390 from a patient's body. Measurement components 392 may include, for example, measurement components such as described above with reference to FIG. 3A.

In some embodiments, the measurement component(s) 392 may not be part of the system 391, and the measurements may be otherwise provided to the system 391, e.g. through one or more interfaces connecting external measurement components to a projecting component 320.

An output 394 of the measurement component(s) 392 is optionally a signal and/or digital data as described above with reference to the output 314 of FIG. 3A.

The output 394 optionally serves as input to a processing component 396 which may be, for example, a computer or a central processing unit.

Figure 3C:
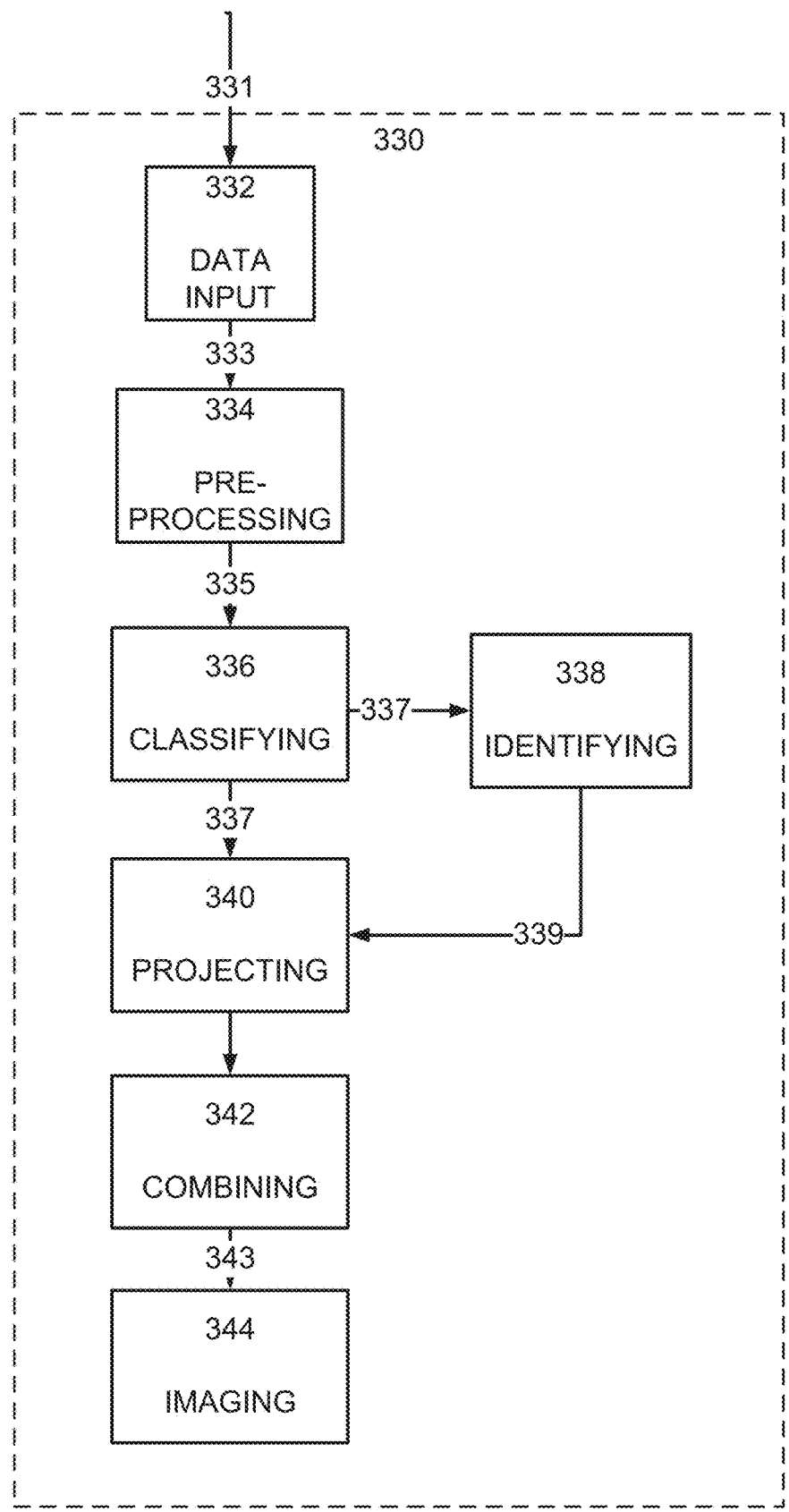
FIG. 3A is a simplified block diagram illustration of a system for measuring medical data, classifying and/or binning the medical data, and transforming the medical data to use a common framework according to some embodiments of the invention.
FIG. 3B is a simplified block diagram illustration of a system for measuring medical data in a first framework and transforming the medical data to a second framework according to some embodiments of the invention.

Reference is now made to FIG. 3C, which is a simplified block diagram illustration of a system for imaging an anatomical structure based on electrical readings according to some embodiments of the invention.

FIG. 3C shows components in a system 330 constructed according to an exemplary embodiment of the invention.

The system 330 optionally includes:

a data input component 332 for receiving electrical readings 331 from a plurality of electrodes (not shown);

an optional pre-processing component 334 for converting output 333 from the data input component 332 to data points 335;

a classifying component 336 for classifying each one of the data points as belonging to one of a plurality of data bins, producing classified data point 337;

an identifying component 338 for identifying correspondence of a set of classified data points 337 in at least a first data bin and a second data bin of the plurality of data bins;

a projecting component 340 for projecting data points in the second data bin to data points in the first data bin using a transformation;

a combining component 342 for producing a combined set of data points 343 comprising the data points of the first data bin and the projected data points from the second data bin; and an optional imaging component 344 for imaging the combined set of data points.

The data input component 332 may include electrodes and/or sensors as described herein, optionally in or on an intra-body probe.

The optional pre-processing component 334 may include a circuit for converting output 333 from the data input component 332 to the data points 335. In some embodiments the optional processing circuit may be a simple circuit for converting an electric reading such as current to a dielectric value such as resistivity, or other electric readings to dielectric values. In some embodiments the optional pre-processing component 334 may be a data processor as is known in the art. In some embodiments the optional pre-processing component 334 may be a software module operating on a data processor as is known in the art.

In some embodiments the optional pre-processing component 334 is used for processing input measurements to data points, not including the projection of data points from one data bin to another.

In some embodiments, the classifying component 336 classifies each one of the data points as belonging to one of a plurality of data bins, and optionally provides the classified data point, to the identifying component 354. The identifying component 354 optionally accepts both the data in the data point and the classification or bin to which the data point belongs, identifies a set of data points in at least a first data bin as corresponding to a set of data points in a second data bin of the plurality of data bins, and provides output 339 of the correspondence of the data points, for example a list of pairs of data points. Alternatively, the identifying component provides only indication as to which points correspond to each other, while the points themselves are delivered directly from the classifying component to the projecting component.

In some embodiments one or more of the processing component 334, the classifying component 336, the identifying component 338, the projecting component 340 and the combining component 342 may include or be included in a data processor as is known in the art, specifically programmed to carry out one or more of the processing, classifying, projecting, and/or combining. In some embodiments the one or more of the pre-processing component 334, the classifying component 336, the identifying component 338, the projecting component 340 and the combining component 342 may be a software module operating on a data processor as is known in the art.

In some embodiments the imaging component 344 may be an image display, whether a two-dimensional display such as a computer display screen or a three-dimensional display as is known in the art.

FIG. 3C describes an exemplary embodiment which includes an optional pre-processing component 334 for converting output 333 from the data input component 332. In such an embodiment the data being classified may be processed electrical readings. For example, the data measured may be voltage values measured by an electrode, and the data classified may be resistivity values calculated by pre-processing component 334 based on the voltage values, and optionally based on further input or inputs.

Figure 3D:
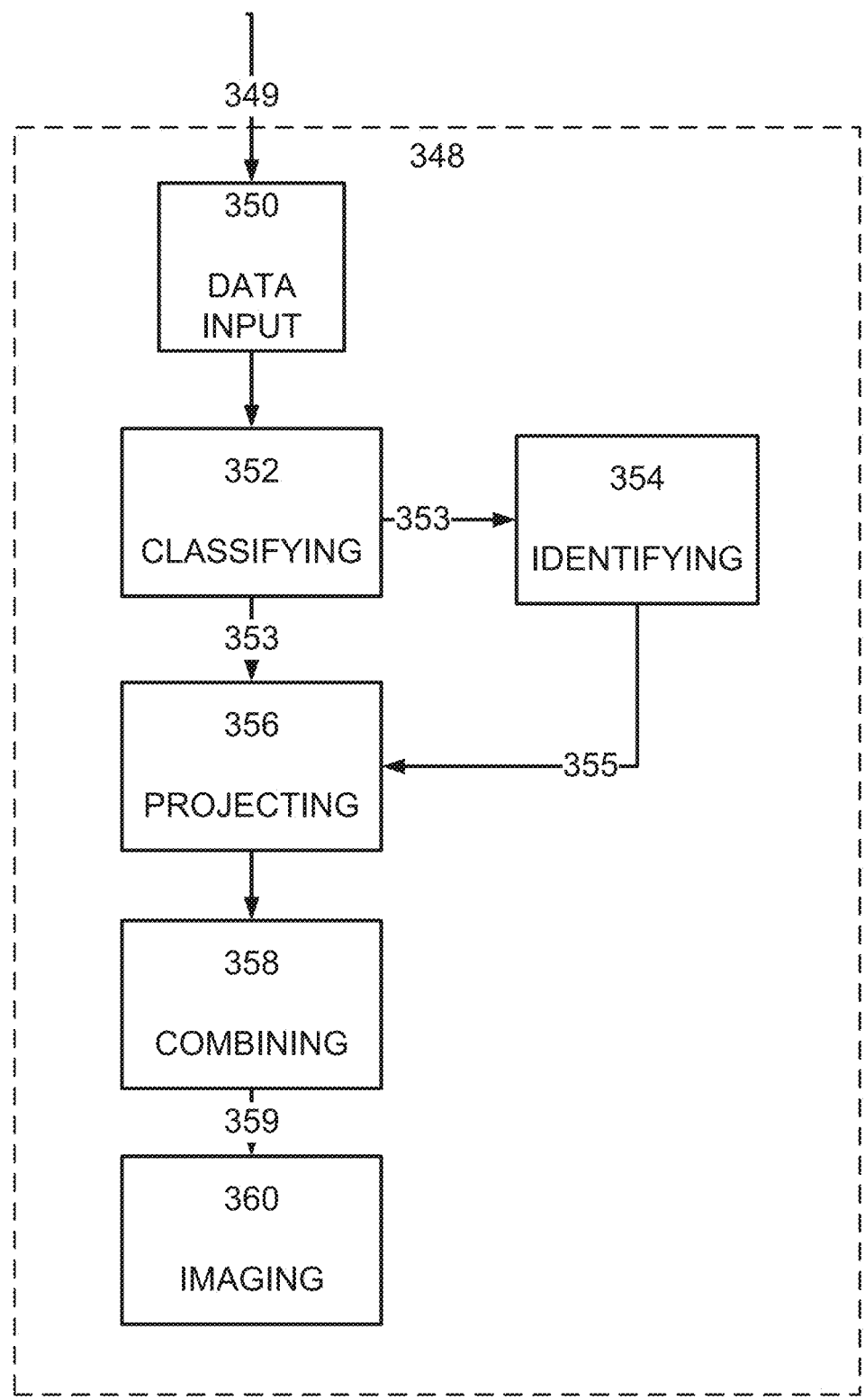

Reference is now made to FIG. 3D, which is a simplified block diagram illustration of a system for imaging an anatomical structure based on electrical readings according to some embodiments of the invention.

FIG. 3D shows components in a system 348 constructed according to an exemplary embodiment of the invention.

The system 348 optionally includes:

a data input component 350 for receiving data points 349 measured from a plurality of electrodes (not shown);

a classifying component 352 for classifying each one of the data points as belonging to one of a plurality of data bins, producing classified data points 353;

an identifying component 354 for identifying 355 a set of corresponding data points in at least a first data bin and a second data bin of the plurality of data bins;

a projecting component 356 for projecting data points in the second data bin to data points in the first data bin using a transformation;

a combining component 358 for producing a combined set of data points 359 comprising the data points of the first data bin and the projected data points from the second data bin; and an imaging component 360 for imaging the combined set of data points.

FIG. 3D describes an exemplary embodiment which does not include a processing component for converting output from the data input component. In such an embodiment the data being classified may be electrical readings which do not require additional processing—by way of a non-limiting example, the data being classified may be voltage as measured by an electrode.

Figure 3E:
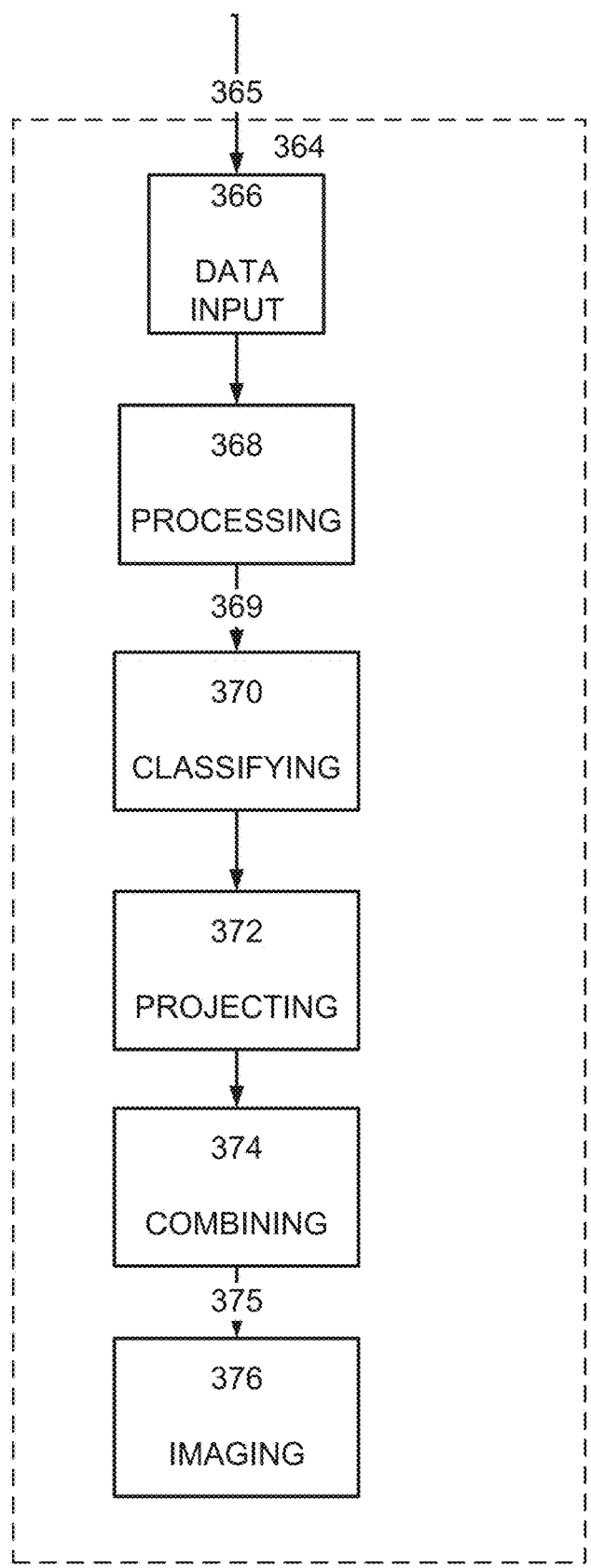

Reference is now made to FIG. 3E, which is a simplified block diagram illustration of a system for imaging an anatomical structure based on electrical readings according to some embodiments of the invention.

FIG. 3E shows components in a system 364 constructed according to an exemplary embodiment of the invention.

The system 364 optionally includes:

a data input component 366 for receiving electrical readings 365 from a plurality of electrodes (not shown);

a pre-processing component 368 for converting the electrical readings to data points 369;

a classifying component 370 for classifying each one of the data points 369 as belonging to one of a plurality of data bins;

a projecting component 372 for projecting data points in a second data bin to data points in a first data bin using a transformation;

a combining component 374 for producing a combined set of data points 375 comprising the data points of the first data bin and the projected data points from the second data bin; and an image generating component 376 for generating an image of the combined set of data points.

FIG. 3E describes an exemplary embodiment which does not include an identifying component for identifying correspondence between classified data points. In such an embodiment the data may be classified as belonging to a specific physiological rhythm, such as a sinus cardiac rhythm, an atrial fibrillation cardiac rhythm, a breathing rhythm. In some embodiments the classification of the data may not affect the projecting from one data bin to another, and the points may be projected from one bin to the other based on, for example, time data or location data, without taking into account a priori correspondence between an identified set of points in one data bin to an identified set of points in the second data bin.

Figure 3F:
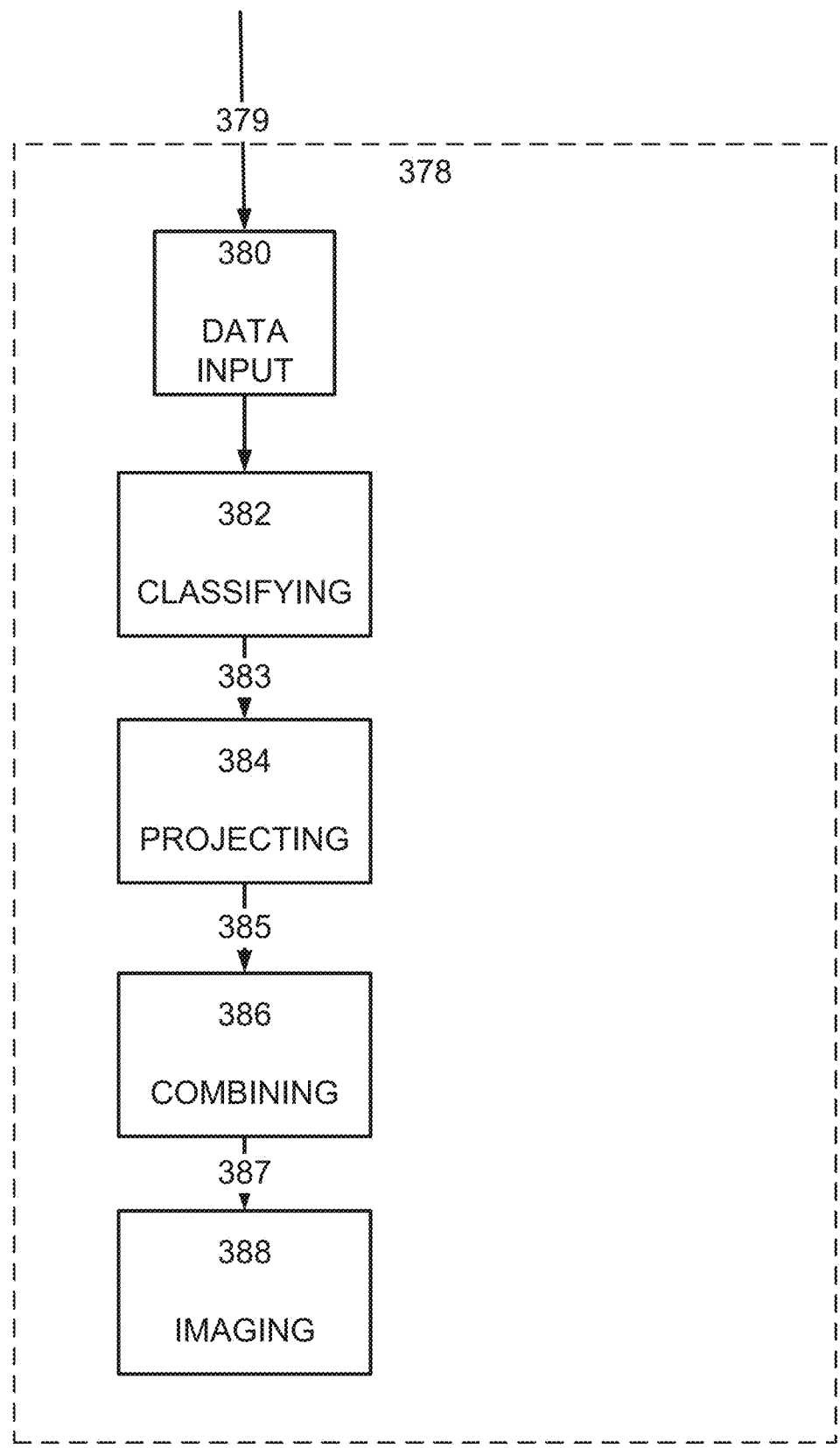

Reference is now made to FIG. 3F, which is a simplified block diagram illustration of a system for imaging an anatomical structure based on electrical readings according to some embodiments of the invention.

FIG. 3F shows components in a system 378 constructed according to an exemplary embodiment of the invention.

The system 378 optionally includes:

a data input component 380 for receiving data points 379 measured from a plurality of electrodes (not shown);

a classifying component 382 for classifying each one of the data points as belonging to one of a plurality of data bins, producing classified data points 383;

a projecting component 384 for projecting data points in a second data bin to data points in a first data bin using a transformation, producing projected data points 385;

a combining component 386 for producing a combined set of data points 387 comprising the data points of the first data bin and the projected data points from the second data bin; and an imaging component 388 for imaging the combined set of data points.

FIG. 3F describes an exemplary embodiment which does not include a pre-processing component for converting output from the data input component. In such an embodiment the data being classified may be electrical readings which do not require additional processing—by way of a non-limiting example, the data being classified may be voltage as measured by an electrode, requiring no pre-processing.

Identifying Corresponding Points in Different Bins

In some embodiments, transforming data point values from a first data bin to a second data bin is optionally based on identifying a set of data points in the first data bin which correspond to data points in the second data bin, and determining a transformation which transforms the corresponding points from the first data bin to the second data bin.

In some embodiments a transformation uses a Coherent Point Drift (CPD) method. In some embodiments the transformation uses a multi-CPD (MCPD) method. A non-limiting example of an MCPD method is described in above-mentioned article "Registration of Multiple Temporally Related Point Sets Using a Novel Variant of the Coherent Point Drift Algorithm: Application to Coronary Tree Matching".

In some embodiments, the transformation which has been determined is optionally applied to some or all of the corresponding data points, calculating transformed values for the some or all of the data points in the set of corresponding data points.

In some embodiments the transformation which has been determined is optionally applied to some or all of the data points in the first data bin, whether belonging to the set of corresponding points or not, calculating transformed values.

It is noted that when a set of corresponding points in the two data bins includes a large number of points, for example, the number of corresponding points is larger than their dimensionality, the transformation determined is potentially accurate.

It is noted that when a set of corresponding points in the two data bins includes a number of points larger than a dimensionality of the data points, the transformation determined is potentially accurate.

Reference is now made to FIG. 4A, which is a simplified flowchart illustration of a method for producing a model of a body organ based on electrical readings according to some embodiments of the invention.

The method of FIG. 4A includes:

measuring at least two data sets of a body organ (440);

determining at least one corresponding data point in each one of the at least two data sets describing the at least one dimension of the body organ which is undergoing repetitive changes (442);

projecting one of the two data sets into another one of the two data sets, based on the corresponding data (444).

In some cases, the repetitive changes in the body organ potentially cause one or more data points in one of the data sets to correspond to one or more data points in another of the data sets. In some cases, the data points correspond regardless of organ's change in time.

In some embodiments the correspondence is optionally based on the corresponding points having been measured at a same location in space, or at a same time along a cycle of the repetitive changes.

By way of a non-limiting example, data measured at a same time along a heartbeat cycle is optionally projected from the one data set onto the other data set.

By way of another non-limiting example, data measured at a same location in a heart chamber, during a different heartbeat, at a same time along the heartbeat cycle, is optionally projected from the one data set onto the other data set.

By way of another non-limiting example, data measured at a same location in a heart chamber, during a different heartbeat, not even at a same time along the heartbeat cycle, is optionally projected from the one data set onto the other data set.

Identifying that data are measured at a same location may involve, in some embodiments, tracking, such as tracking with X-ray or Ultrasound.

Reference is now made to FIG. 4B, which is a simplified flowchart illustration of a method for imaging a patient organ based on electrical readings according to some embodiments of the invention.

The method of FIG. 4B includes:

receiving measurements from a plurality of electrodes (420);

classifying the measurements to a plurality of data bins (422);

identifying a set of corresponding data points in at least a first data bin and a second data bin of the plurality of data bins (424);

calculating a transformation from the corresponding data points in the second data bin to the corresponding data points in the first data bin (426);

projecting data points in the second data bin to data points in the first data bin using the transformation (428);

producing a combined set of data points comprising the data points of the first data bin and the projected data points from the second data bin (430); and imaging the combined set of data points (432).

In some embodiments the transformation is optionally a CPD or multi-CPD transformation.

In some embodiments the transformation is temporally coherent.

Reference is now made to FIG. 5A, which is a simplified flowchart illustration of a method for combining gate-projected data points according to some embodiments of the invention.

FIG. 5A describes, by way of a non-limiting example, obtaining data points which are voltage measurements from an intra-body probe near to and/or inside a patient's heart, and gate-projecting the data points to a common reference data bin.

The method of FIG. 5A includes:

Obtaining data points (V, θ, φ) (302), that is measuring voltage V or voltages at one or more electrode in the probe, and determining a value θ associated with breathing, and determining a value φ associated with the cardiac rhythm. The value θ optionally includes a length of time from a beginning of a breathing cycle, and/or a percentage of progression along the breathing cycle, and/or a type of breathing cycle, such as long, short, panting, sigh. The value φ optionally includes a length of time from a beginning of a cardiac cycle, and/or a percentage of progression along the cardiac cycle, and/or a type of cardiac cycle, such as chaotic, atrial fibrillation, regular, clear, unclear, and/or a phase of the cardiac cycle such a P, Q, R, S, T.

Calculating (R, θ, φ) (304), that is, calculating a location R, which may be a one, two or three dimensional location, for the data points. The calculation is described by the following transformation:

$$V(\theta, \varphi) \xrightarrow{f} R(\theta, \varphi).$$

In some embodiments the calculation f is optionally done by methods described in above-referenced PCT Application WO 2018/130974, for example methods named multidimensional scaling (MDS) and/or spatial coherence, optionally done by methods named Coherent Point Drift (CPD), or multi-CPD (MCPD), which impose spatial coherence on (R, θ, φ).

Calculating (R, $\theta_0$, φ) (306), that is, gate projecting values of data points from data bins associated with different θ values, to a common reference, or from a first data bin of a first θ value to a second data bin, of a second θ value, $\theta_0$. Optionally, data bins associated with multiple different θ values are gate projected to the same $\theta_0$ data bin. For example, the data bin associated with the value $\theta_0$ may be a master-bin. The calculation, or gate projection, from one bin θ to the master-bin $\theta_0$ is described by the following transformation:

$$R(\theta, \varphi) \xrightarrow{g} R(\theta_0, \varphi).$$

In some embodiments the transformation g is optionally spatial coherent, and may be found by a Coherent Point Drift (CPD) algorithm, or a multi-CPD (MCPD) algorithm.

Calculating (R, $\theta_0$, $\varphi_0$) (308), that is, gate projecting values of data points from data bins associated with different φ values, to a common reference, or from a first data bin of a first φ value to a second data bin, of a second φ value, $\varphi_0$. The calculation, or gate projection, from one bin φ to the master-bin $\varphi_0$ is described by the following transformation:

$$R(\theta, \varphi) \xrightarrow{h} R(\theta, \varphi_0).$$

In some embodiments the transformation h is optionally spatial coherent, and may be found by a Coherent Point Drift (CPD) algorithm, or a multi-CPD (MCPD) algorithm.

Following the above-mentioned gate-projections data points from additional data bins are optionally used to produce an image R of the patient's heart. By way of a non-limiting example, before gate projection, data points from a data bin "0" (which may be a master-bin) could have been used to produce an image $R_0$, and following the gate-projection, data points which did not originally occur in data bin "0" are combined by gate-projection onto a set of data points used to produce a new image $R_0$.

In some embodiments the method of FIG. 5A is applied only for a normal rhythm of a heart, that is, for example, non-chaotic, and/or not during atrial fibrillation.

It is noted that though the method above is described in relation to breathing and cardiac beating gate projections, in some embodiments, gate projection may optionally be performed solely for breathing or solely for beating.

An Example Method of Obtaining a g or an h Function

After calculating (R, θ, φ) (304), the following R clouds are obtained: $R_1, R_2, \ldots R_N$, where N is a number of data bins.

In the following description the g function is described, and a similar description is intended to apply to the h function described above.

A g function is optionally calculated for each R cloud: $g_i$: Ri→$R_0$, where $R_0$ may be an optionally arbitrary selection of a data bin "0", also referred to herein as a master-bin.

In some embodiments the g functions are optionally calculated by multi-CPD ('MCPD'), to find a sequence of transformations that is temporally coherent.

In some embodiments the g function is optionally calculated by multi-CPD so that the $g_i$ functions of temporally neighboring data bins be similar, close to each other, smoothly changing.

Reference is now made to FIG. 5B, which is a simplified flowchart illustration of a method for combining gate-projected data points to produce a combined image according to some embodiments of the invention.

FIG. 5B describes in words rather than mathematical symbols, obtaining data points which are voltage measurements from an intra-body probe near to and/or inside a patient's heart, and gate-projecting the data points to a common reference data bin.

The method of FIG. 5B includes:

obtaining data points (402);

producing data sets for each data bin (404);

performing gate projection to account for breathing (406);

performing gate projection to account for cardiac rhythm (408);

using a combined data set including gate-projected values to produce a combined image (410).

Additional non-limiting example methods are further described below.

Reference is now made to FIG. 6A, which is a simplified flowchart of a method for imaging an anatomical structure based on electrical readings according to an exemplary embodiment of the invention.

The method of FIG. 6A includes:

receiving electrical readings from a plurality of electrodes (602);

converting the electrical readings to data points (603);

classifying each one of the data points as belonging to one of a plurality of data bins (604);

identifying a set of corresponding data points in at least a first data bin and a second data bin of the plurality of data bins (605);

projecting data points in the second data bin to data points in the first data bin using a transformation (606);

producing a combined set of data points comprising the data points of the first data bin and the projected data points from the second data bin (607); and imaging the combined set of data points (608).

Reference is now made to FIG. 6B, which is a simplified flowchart of a method for imaging an anatomical structure based on electrical readings according to an exemplary embodiment of the invention.

The method of FIG. 6B includes:

receiving data points measured from a plurality of electrodes (612);

classifying each one of the data points as belonging to one of a plurality of data bins (613);

identifying a set of corresponding data points in at least a first data bin and a second data bin of the plurality of data bins (614);

projecting data points in the second data bin to data points in the first data bin using a transformation (615);

producing a combined set of data points comprising the data points of the first data bin and the projected data points from the second data bin (616); and imaging the combined set of data points (617).

Reference is now made to FIG. 6C, which is a simplified flowchart of a method for imaging an anatomical structure based on electrical readings according to an exemplary embodiment of the invention.

The method of FIG. 6C includes:

receiving electrical readings from a plurality of electrodes (622);

converting the electrical readings to data points (623);

classifying each one of the data points to as belonging to one of a plurality of data bins (624);

projecting data points in a second data bin to data points in a first data bin using a transformation (625);

producing a combined set of data points comprising the data points of the first data bin and the projected data points from the second data bin (626); and imaging the combined set of data points (627).

Reference is now made to FIG. 6D, which is a simplified flowchart of a method for imaging an anatomical structure based on electrical readings according to an exemplary embodiments of the invention.

The method of FIG. 6D includes:

receiving data points measured from a plurality of electrodes (632);

classifying each one of the data points to as belonging to one of a plurality of data bins (633);

projecting data points in a second data bin to data points in a first data bin using a transformation (634);

producing a combined set of data points comprising the data points of the first data bin and the projected data points from the second data bin (635); and imaging the combined set of data points (636).

Classifying Data into Data Bins

In some embodiments, data points are optionally classified into data bins according to types of cardiac and/or respiratory cycles, according to a phase within a cardiac cycle, and optionally further classified in the time domain. For example, data points measured during a P segment of heartbeat may be binned in some embodiments into four bins, for example, data measured during the first quarter of a duration of the P segment may be classified into a first bin, data measured during the second quarter may be classified into a second bin, etc. Some non-limiting examples of data bins based on types of cardiac cycles include sinus rhythm, atrial fibrillation, ventricular fibrillation, arrhythmia, and so on. Some non-limiting examples of types of breathing cycles include breathing at rest, breathing under stress, shallow breathing, deep breathing, and so on.

In some embodiments the time domain data bins may overlap. For example the time domain may be divided into several data bins, in the overlapping ranges of 0-20%, 10-30%, 20-40%, etc.

In some embodiments the time domain data bins may be unequal in length, regardless if they overlap or not. For example the time domain may be divided into 7 data bins, in the ranges of 0-20%, 20-40%, 40-50%, 50-60%, 60-70% and 80-90%, and 90-100%.

In some embodiments the time domain data bins may be both overlapping and unequal in length.

In some embodiments the time domain data bins may be both overlapping and unequal in length.

In some embodiments classifying data bins is optionally based on distinguishing between rhythm states. In some embodiments, the distinguishing is optionally performed by distinguishing between sinusoidal and chaotic heartbeats, as described in the above-mentioned article titled "A real-time atrial fibrillation detection algorithm based on the instantaneous state of heart rate", PLoS ONE 10(9) e0136544er.

In some embodiments classifying data bins is based on distinguishing between various sinusoidal beats (e.g., 80 BPS and 70 BPS), by way of a non-limiting example by using a hidden Markov model.

In some embodiments, the above two methods are combined, for example, by first distinguishing between sinusoidal and chaotic rhythms, and then distinguishing, within the sinusoidal rhythm, between different heartbeat rates.

Correspondence Between Data Bins

In some embodiments the data bins optionally correspond to physiological states of an anatomical structure. In some embodiments, such a state is optionally described by an average value of specific data in the data bin, and/or a standard deviation of the specific data.

In some embodiments, the transformation is performed in series. Optionally, a transformation taking into account a type of cardiac rhythm (sinus, arrhythmia, fibrillation and so on as described elsewhere herein) is performed, optionally followed by a transformation taking into account a phase in the respiratory rhythm, optionally followed by a transformation taking into account a phase in the cardiac correspondence. By way of a non-limiting example, data gathered under one rhythm is optionally projected into data gathered under a different rhythm—for example, a map that was acquired during atrial fibrillation is optionally projected into another map that was acquired during a sinusoidal rhythm.

In some embodiments a transformation may be decomposed to (or generated as) a sum of N individual transformation functions, each characterized by a different spatial frequency.

In some embodiments, especially when N is a large number, for example above 1,000 points, the transformation is a sum of n transformations (where n<N). In some embodiments the number n of functions used to generate the transformation is low relative to N, for example x=3, 5, 10, 20, 50, or 100. Such a combined transfer function is typically sufficient to provide a good and smooth result.

In some embodiments, the transformation from one bin to another may be simplified by generating a transformation that has only low-frequency components. Such a simplified transformation may result in relatively smooth images, which has low tendency to follow noise in the data, and low capability to follow small details in the structure that the data represents. For example, in some embodiments, a transformation configured to transform N points (e.g., 1000 or more) is represented as a sum of N components, characterized by different spatial frequencies (optionally, by N different spatial frequencies). Out of these components, only the n ones characterized by the lowest frequencies, are used for transforming data, and the rest—discarded. In some embodiments, n is between about 10% and about 20% of N, for example, 1000 points may be transformed with a transformation made of between 100 and 200 components. In some embodiments, the number of components, or its ratio to the number of points, may be predetermined. In some embodiments, a cost function may be used for finding transformations with only low-frequency components, for example, by penalizing high-frequency components.

In some embodiments, the transformation of data from one bin to another may be constrained to by applying a "penalty" to the various components of the displacement: the higher the spatial frequency of a component, the larger is the penalty to its contribution. Once a displacement W that minimizes the overall penalty (e.g., a sum, optionally a weighted sum, of the penalty for misfit and the penalty for high spatial frequencies) is obtained, it may be used to displace transform points from the source bin to a target bin. Finding a transformation that minimizes the penalty may be carried out using standard minimization procedures.

In some embodiments, a canonical state (also referred to as a base state or a master state or a base rhythm) is optionally defined as one of the rhythm states (e.g. normal, AF, VF, etc.), and images from other rhythms are projected onto the canonical state. Such a projection may be conceptually similar to having a master image, and projecting other images onto the master image. Projecting other rhythms onto a canonical rhythm is most effective when there is a lot of data measured during each rhythm state, so that a meaningful registration may be obtained despite of substantial differences between the structure of the body part in the canonical state, and said structure in states projected on the canonical state.

In some embodiments an output of each step of the transformation is a projected base rhythm, with a transformed base respiration and a transformed dominant beat, within each one of which are non-base rhythms projected into the normal rhythm; the abnormal respiratory breaths projected into the normal breaths; and the abnormal cardiac beats projected into the normal cardiac beats.

In some embodiments, within each of the normal breath phases and the normal heart beat phases, projection is further performed using a correspondence between the phase data bins of each signal into a base rhythm data bin.

Reference is now made to FIG. 7A, which is a graph 500 showing an example effect of gate-projection on data points according to some embodiments of the invention.

FIG. 7A shows values of data points collected over time, and values of gate-projected data points.

FIG. 7A shows a first dotted line 503 showing values of data points collected along an X-axis 501 of time, in seconds, and a location of the data points along a Y-axis 502, in millimeters, which corresponds to locations of the points in space, similar to the values R described with reference to FIG. 5A.

FIG. 7A also shows a second, solid line 504 showing transformed, or gate-projected, Y values of the same data points after gate-projection.

FIG. 7A shows an example of R data values, measured along the Y-axis 502 before gate projection (503) and after gate projection (504).

As mentioned above, in some embodiments the methods described with reference to the system of FIGS. 3A-3E are applied only for a normal rhythm of a heart, that is, for example, non-chaotic, and/or not during atrial fibrillation.

In some embodiment gate projection is optionally performed between different rhythmus heartbeat rhythms p. In some embodiments gate projection is optionally used to compensate for movement of an image or a model of a heart between different rhythms of a heartbeat of a patient, for example when transiting from standard rhythm (SR), or "normal rhythmus", to atrial fibrillation (AF), for example by applying a function $g_i$ or $h_i$ from AF to SR.

Reference is now made to FIG. 7B, which is a graph showing a normal cardiac rhythm and an abnormal cardiac rhythm differentiated according to some embodiments of the invention.

FIG. 7B shows a duration of each heartbeat cycle along a Y-axis 512, in seconds, and a progression of time at which the heartbeat cycle was measured, as a frame number in a series of time-sequential frames.

A first set of data points 514 is shown as having a normal cardiac cycle of 1.24+/−0.02 seconds.

A second set of data points 513 is shown as having an abnormal cardiac cycle of 1.02+/−0.29 seconds.

In some embodiments, a heartbeat is determined to belong in an abnormal data bin if the heartbeat duration is longer than a normal and/or average heartbeat duration by an amount greater than a threshold value in seconds, and/or in percentage, of normal heartbeat duration.

In some embodiments a normal rhythmus is optionally determined by Markov methods from the data, for example, using Hidden Markov Models.

HMM (Hidden Markov Models) are statistical models that describe a time series by a set of unobserved states, where each state has a probability distribution (e.g., Normal distribution) over the observed output. The model is defined by these distributions and by the transition probability from one state to another.

In some embodiments the normal rhythm is optionally calculated based on the observed sequence of outputs, for example R-R (peak-to-peak period of cardiac rhythm) and/or B-B (peak-to-peak period of breathing rhythm).

For patients that experience extreme AF, data may not be acquired for a normal rhythm and data is acquired and used only from AF cycles.

A non-limiting example of multi-modality imaging using intra-body probe-detected data is now provided. The example is suited for using gate-projection as described herein to improve the imaging by using more data points per image and/or by filling in missing data from an image produced by one data bin with data from a transformed, gate-projected set of values from another data bin.

Reference is now made to FIG. 8, which is a simplified line drawing illustration of methods of gathering position-identifying information using intra-body probes according to some embodiments of the invention.

FIG. 8 shows intra-body probes 11A, 11B, 11C, within a body cavity, according to some exemplary embodiments of the present disclosure. The probes shown may be indicative of different types of data gathering, and do not necessarily imply simultaneous positioning of all the probes.

In some exemplary embodiments an intra-body probe is optionally introduced into a body, and into a body part or to a vicinity of a body part. The intra-body probe is optionally used to produce various measurements, such as electrical measurement, and/or other measurement described herein.

In some embodiments a location of the intra-body probe is optionally tracked using a tracking system dedicated to the tracking.

In some embodiments a location of the intra-body probe is tracked by analyzing signals received by the intra-body probe.

Probes 11A, 11B, 11C are shown in a volume 600 to be mapped, to illustrate acquisition of data, which can be used to assist in refining and/or constructing a model. The probes may acquire data using different modalities of data acquisition, such as measuring electric potential, electric current, temperature, pH, and so on.

Probe 11A is shown in an act of measuring endogenous electrical activity 63 in a region of heart atrium wall tissue 50. Optionally, in some embodiments, measured electrical activity (e.g., an electrogram) is used as an indicator of position of a probe, for example, based on a phase delay with which activity is measured at a particular position, compared to some landmark phase, such as the QRS complex of an electrocardiogram (ECG). Optionally, the phase difference is measured relative to a non-contacting electrode on probe 11A itself (for example, a ring electrode), which potentially helps to cancel surrounding noise. This phase delay is optionally treated as creating a data dimension applicable across a surface of a heart. In some embodiments, such a probe 11A potentially produces measurement data (electrical activity) which can be used to calculate a time relative to a start of the cardiac rhythm, or a phase within the cardiac rhythm.

Probe 11B is shown partially exploring the interior of a root of pulmonary vein 48. Different tissue structures have been found to display noticeably different impedance behaviors which can be gathered by electrodes of an intra-body probe and distinguished through analysis, for example, by a dielectric property analyzer, optionally in communication via an electromagnetic field generator/measurer used to operate electrodes on the probe(s). In particular, in some embodiments of the invention, positions within veins and within heart atria are optionally distinguished according to their impedance properties with positions in veins, for example, having a relatively higher impedance value. In some embodiments, such a probe 11B potentially produces measurement data (electrical activity) which can be analyzed to determine a dielectric property such as impedance, which can be used to estimate a position of the probe, for example as a position at an atrial wall, characterized by an impedance strictly different than the atrial blood pool.

In some embodiments, distinguishable dielectric properties of tissue itself are optionally used as a landmark. Tissue dielectric properties are optionally measured, for example, as described in PCT patent application publication number WO 2016/181316 titled "Contact Quality Assessment by Dielectric Property Analysis", the contents of which are incorporated herein by reference in their entirety. Transitions between two tissue types (and/or any other impedance change landmarks, for example due to tissue wall thickness, scarring, ablation, edema, and the like) are optionally used to register a voltage/spatial mapping to a more accurately determined size. Additionally or alternatively, such landmarks optionally serve in re-identification of tissue positions in case of changes to an electromagnetic field-based frame of reference.

It is noted that such use of landmarks comprises mapping relative to contact with identified structural features of interest directly, as distinguished from mapping relative to spatially-defined coordinates (at which structural features are supposed to exist). Potentially, this is particularly useful when navigation targets such as in heart atrial wall are in continuous movement relative to spatially-defined coordinates. Optionally, both types of information are used together: for example, a spatial coordinate system is established by measurements of voltages in a spatially distributed electromagnetic fields, and tissue landmarks identified by contact measurements from a probe are assigned coordinates as they are encountered.

Probe 11C is shown in contact with a general region 62 of atrium wall tissue 50, that is, a region which is not particularly singled out as a landmark. The inventors have found that it is possible, in some embodiments, to detect an anterior-posterior gradient in the size of voltage fluctuations while in contact with atrial heart wall tissue, due to relatively greater anterior movement as a result of heart contraction. Optionally, this fluctuation gradient itself serves as another part of a frame of reference for defining positions in contact with the heart wall.

In some embodiments of the invention, apart from one or more of the various sensing modalities described herein, a position of an intra-body probe, optionally including electrodes thereon, in a spatial frame of reference is constrained by one or more mechanical and/or geometrical considerations. For example, the range of possible positions and/or orientations of a probe known to have entered a region of tissue from a particular entrance point (a vein, artery, or fossa, for example) is optionally reduced to a plausible subset from all possible positions and/or orientations. Mechanical constraints on probe shape may also be used in position determinations.

A non-limiting example of other modalities for obtaining voltage/spatial mapping information is now provided.

Apart from probe-measured sources, other sources of information useful for establishing and/or refining voltage/spatial mapping are available in some embodiments of the invention. It should be understood that these methods of voltage/spatial mapping can optionally be used jointly with the example of multi-modality imaging using intra-body probe-detected data described above, for example to provide initial anatomical maps and/or to refine a voltage/spatial mapping provided by the example described above. A combination of techniques can be arranged, for example, by use of a merging algorithm which provides suitable weights to various data sources.

To begin with, anatomical data is optionally sourced from 3-D medical images of the patient and/or from anatomical atlas data. Optionally, geometrical anatomical landmarks expected from the anatomical data are identified by moving a probe within a patient until the probe encounters identifiable landmarks, and registering voltages to spatial positions according to a characteristic shape, such as a wall of a sinus or a cavity of a vein, that is seen in the probe travel. Optionally, an overall shape of a voltage-sample based construction of a model X is subjected to a geometrical transformation T to fit an anatomy of a reference geometry Y derived from anatomical data. The transformation $T(X) \approx Y$ is optionally described, e.g., by the parameters of an optimal fit of an affine transformation. Additionally or alternatively, in some embodiments, the transformation is based on a mapping of corresponding landmarks in X and Y; i.e. the transformation T is found by matching landmark sets in the voltage sample-based construction of a model X* with corresponding geometrically located landmarks Y* to find T(X*)≈Y*.

Anatomical data can also provide simple constraints to voltage/spatial mapping, for example, by showing in what general region a heart chamber falls compared to the positions of body surface electrodes.

Optionally, anatomical data may be used for constructing more detailed electromagnetic field simulation data; for example, as described in International Patent Application No. PCT IB2016/052692, filed May 11, 2016 and titled FIDUCIAL MARKING FOR IMAGE-ELECTROMAGNETIC FIELD REGISTRATION, the contents of which are incorporated herein by reference in their entirety. The more detailed electromagnetic field simulation data are optionally used to provide a starting point to assign initial positions of intra-body probe voltage samples. Alternatively or additionally, the more detailed electromagnetic field simulation data may be used as a post-construction constraint (for example, a criterion which can optionally exclude erroneous measurement values).

Reference is now made to FIG. 10A, which is a flowchart illustration of a method of generating an image of a body part according to an exemplary embodiment of the invention.

The image to be generated is a combined image, generated based on a sequence of three or more images of a same body part. The images may overlap partially or wholly. The images may be obtained, for example, from measurements made by an intra-body probe that moves in respect to the body part. For example, the body part may be a blood vessel along which the probe travels. In another example, the body part may be a heart chamber, and the probe may be inside the heart chamber, static (e.g., pressed against a wall of the heart chamber) or roving inside the heart chamber.

Each image shows the body part as captured at a different time, for example, at time differences of less than a second, e.g., of 0.05 seconds, 0.1 seconds, 0.2 seconds, 0.5 seconds, 0.7 seconds, 0.8 seconds, etc. Larger time differences, e.g., of 1 second, 2 seconds, 10 seconds, 20 seconds, 30 seconds, etc., are also possible. Each image captures the body part during a certain time window. In some embodiments, some of these time windows may partially overlap, for example, there may be an overlap between the time windows of each two consecutive images in the sequence. In some embodiments, the overlap between time windows may be small (e.g., less than 20% overlap), large (e.g. 80% or more), or intermediate (e.g., between 20% and 80%). Typically, the larger the overlap, the more similar are the images to each other, and the transformations may be easier to find, although a larger number of images (and transformations) may be required to cover a specific period of time. In some embodiments, the time at which data of each time window was taken may be attributed to a certain point in the window, e.g., the window start, end, middle, etc. A time difference between such two points (e.g., between the middle of two time windows) may be referred to as the time difference between the two time windows.

In some embodiments, each image in the sequence is location-based, i.e., it is made of points representing locations. For example, points in the image may represent locations in space, for example, locations of anatomical landmarks (e.g., the mitral valve, a left atrium appendage, etc.) or any other feature in the body part. In some embodiments, each image in the sequence is measurement-based, i.e., made of points representing readings of values other than locations (e.g., voltages read by electrodes on a probe probing the body part). The readings, however, may be indicative of locations, so that location-based images may be generated from the measurement-based images. In some embodiments, the method may be applied to a sequence of measurement-based images, and produces a result of a single measurement-based image. The measurement-based image may be transformed into a location-based image by any means known in the art. By way of a non-limiting example, one way to transform measurement-based images to location-based images is for a case where the measurements are of voltages measured by electrodes of a probe, when crossing electromagnetic fields are applied to a body part from outside the patient's body, described in the above-mentioned PCT Application WO2018/130974. Alternatively, if the images are received as measurement-based images, they may be transformed into location-based images, and the method may be practiced on these location-based images.

In some embodiments, the images may be provided as point clouds. In some such embodiments, the registration may be practiced on the point clouds, and after a combined point cloud is obtained from a sequence of point clouds, the combined point cloud may be reconstructed to obtain another kind of image, for example, an image of an outer shell of the point cloud. Alternatively, each of the provided point cloud images may be first reconstructed, e.g., into an outer shell image, so the single image is obtained as an outer shell or any other kind of image, reconstructed from the point cloud. In both cases, the reconstruction may be using any reconstruction method known in the art as such, for example, a pivoting ball algorithm.

The method of FIG. 10A includes:

defining a transformation for registering a first image to a second image (1002);

using the defined transformation for registering the first image to the second image (1004); and combining the first image with the second image to provide a single combined image (1006).

In some embodiments, a sequence of transformations is defined, in which each image is registered to another one of the images. The transformations may be of any kind known in the art as a registration transformation. The transformations may be rigid, or non-rigid.

In some embodiments, a specific region is marked on all the images in the sequence. For example, a fiducial marker may be attached to a point in the body part, at least during the imaging process, and thus appear in each of the images in the sequence. The fiducial marker may be, for example, a catheter tip pressed against a point in a heart chamber wall. In such embodiments, the registration transformations may be defined to register the fiducial marker in all the images to each other.

In some embodiments, a processor (e.g., processor 316 of FIG. 3A) may identify an anatomical landmark in the images. In such embodiments, the registration transformations may be defined to register the identified landmarks in all the images in the sequence to each other. In some embodiments such an identified anatomical region may provide a constraint on an algorithm that searches for suitable transformations, and thus may potentially shorten the search, and may improve the quality of the registration achieved. An exemplary method of automatically identifying landmarks from voltage readings of an intra-body probe may be found in PCT Application WO 2018/207128.

In some embodiments, the transformations are defined to be temporally coherent. In this context, temporal coherence is a property of a sequence of transformations. While a single transformation is considered spatially coherent if it transforms points that are near each other in a source image (e.g., in one of the non-master images) to points that are near each other in the target image (e.g., in the master image); a sequence of transformations is temporally coherent if the transformation of points by one transformation is similar to the transformation of the same point by the following (or preceding) transformation in the sequence.

In some embodiments, the sequence of transformations is temporally coherent. A method for ensuring that a sequence of transformations is temporally coherent, is by verifying that the difference between each two sequential transformations provides a transformation that by itself is spatially coherent.

In some embodiments, finding a spatially coherent transformation, e.g., by the above-mentioned CPD algorithm, may include minimizing a cost function, which includes a penalty for high frequency components of the transformation. Finding a temporally coherent sequence of transformations may involve adding to a cost function a penalty term that penalizes for high frequencies in transformations, each of the transformations obtained by subtracting one of the transformations in the sequence from an adjacent (following or preceding) transformation in the sequence.

In some embodiments, a temporally coherent sequence of transformations is optionally used for registering the images in the sequence with each other, for example, by registering all the non-master images with the master image.

In some embodiments, operation of the transformations may be interlaced with the definition of the transformations. Optionally, each transformation (but the first) may be defined to be temporally coherent with a preceding transformation.

Reference is now made to FIG. 10B, which is a flowchart illustration of a method of generating an image of a body part according to an exemplary embodiment of the invention.

FIG. 10B illustrates a method of registering multiple images to a master image.

An image to be generated is optionally a single combined image, generated based on a sequence of at least three (but typically more) partially overlapping images of a same body part. The partially overlapping images may be obtained, for example, from measurements made by an intra-body probe that moves in respect to the body part. For example, the body part may be a blood vessel along which the probe travels. In another example, the body part may be a heart chamber, and the probe may be inside the heart chamber, static (e.g., pressed against a wall of the heart chamber) or roving inside the heart chamber.

Each image in the sequence shows the body part as captured at a different time, for example, at time differences of less than a second, e.g., of 0.05 seconds, 0.1 seconds, 0.2 seconds, 0.5 seconds, 0.7 seconds, 0.8 seconds, etc. Larger time differences, e.g., of 1 second, 2 seconds, 10 seconds, 20 seconds, 30 seconds, etc., are also possible. Each image captures the body part during a certain time window. In some embodiments, parts of some of these time windows may overlap, for example, there may be an overlap between the time windows of each two consecutive images in the sequence. In some embodiments, the overlap between time windows may be small (e.g., less than 20% overlap), large (e.g. 80% or more overlap), or intermediate (e.g., between 20% and 80%). Typically, the larger the overlap, the more similar are the images to each other, and the transformations may be easier to find, although a larger number of images (and transformations) may be required to cover a specific period of time. In some embodiments, the time at which data of each time window was taken may be attributed to a certain point in the window, e.g., the window start, end, middle, etc. A time difference between such two points (e.g., between the middle of two time windows) may be referred to as the time difference between the two time windows.

In some embodiments, each image in the sequence is location-based, i.e., it is made of points representing locations. For example, points in the image may represent locations in space, for example, locations of anatomical landmarks (e.g., the mitral valve, a left atrium appendage, etc.) or any other feature in the body part. In some embodiments, each image in the sequence is measurement-based, i.e., made of points representing readings of values other than locations (e.g., voltages read by electrodes on a probe probing the body part). The readings, however, may be indicative of locations, so that location-based images may be generated from the measurement-based images. In some embodiments, the method may be applied to a sequence of measurement-based images, and produces a result of a single measurement-based image. The measurement-based image may be transformed into a location-based image by any means known in the art. By way of a non-limiting example, one way to transform measurement-based images to location-based images is for a case where the measurements are of voltages measured by electrodes of a probe, when crossing electromagnetic fields are applied to a body part from outside the patient's body, described in the above-mentioned PCT Application WO 2018/130974. Alternatively, if the images are received as measurement-based images, they may be transformed into location-based images, and the method may be practiced on these location-based images.

In some embodiments a number of images in the sequence is at least three, and usually less than 100, for example, 5, 10, 20, 50, or any other number between 3 and 100. The images are optionally ordered in the sequence according to the times of capturing the images. If movement between the body part and the probe is periodic (e.g., in case the body part is the heart or a portion thereof, and the probe is in a beating heart), the images may be ordered according to the phase in a cardiac cycle, in which they were captured. For example, an image taken in the middle of a diastolic phase of a heartbeat may be ordered after an image taken at the beginning of the diastolic phase of a later heartbeat. In some embodiments the order by which the images are arranged plays a role in generating the single, combined, image.

The method of FIG. 10B includes:

defining a sequence of transformations for registering images in the sequence of images to a master image, which is optionally one of the images in the sequence (1012);

using the defined sequence of transformations for registering the images to the master image (1014); and combining the registered images with the master image to provide a combined image (1016).

In some embodiments, the sequence of transformations is defined serially. For example, after a first image is registered with a master image, the first image and the master image are combined, and a transformation is optionally defined to register the combined image with a third image, and so on, optionally to the end of the sequence. In such embodiments, 1012 1014 1016 are executed again and again, and in each execution one of the images is added to the previous ones, so as to generate a final single combined image.

In 1016, co-registered images (i.e., the original images, when registered with each other), are combined to provide a single combined image. In some embodiments it is also possible not to use all the images, but only some of the co-registered images. The combining 1016 may be carried out by generating a single set of points, which includes all the points of the combined images.

In some embodiments, the transformations in the sequence of transformations are defined in 1012 to be temporally coherent. As mentioned above, temporal coherence may be a property of a sequence of transformations. While a single transformation is considered spatially coherent if it transforms points that are near each other in a source image (e.g., in one of the non-master images) to points that are near each other in the target image (e.g., in the master image); a sequence of transformations is temporally coherent if the transformation of points by one transformation is similar to the transformation of the same point by the following (or preceding) transformation in the sequence. In this context "similar" may mean that the two transformations displace the point in about the same direction and about the same distance, so that a sequence of temporally coherent transformations displaces the points in time along substantially smooth trajectories. Optionally or additionally, a sequence of temporally coherent transformations, transforms the points of the source image to the points of the target image along non-crossing (or minimally crossing) trajectories.

One method of ensuring that a sequence of transformations is temporally coherent, includes verifying that the difference between each two sequential transformations provides a transformation that by itself is spatially coherent. In some embodiments, each of the transformations in the sequence is itself spatially coherent, but this is not sufficient to ensure that the sequence is temporally coherent.

In some embodiments, finding a spatially coherent transformation, e.g., by the above-mentioned CPD algorithm, may include minimizing a cost function, which includes a penalty for high frequency components of the transformation. Finding a temporally coherent sequence of transformations may involve adding to a cost function a penalty term that penalizes for high frequencies in transformations, each of which is obtained by subtracting one of the transformations in the sequence from an adjacent (following or preceding) transformation in the sequence. In some embodiments, a temporally coherent sequence of transformations is optionally used for registering the images in the sequence with each other, for example, by registering all the non-master images with the master image.

Reference is now made to FIG. 11A, which is a simplified flowchart illustration of a method for combining N images into one, according to an exemplary embodiment of the invention.

FIG. 11A is a flowchart showing steps in a serial execution of the methods described above, and FIG. 11B is a flowchart showing steps in parallel execution of the methods. Both flow charts begin with receiving N images.

The method of FIG. 11A includes:
receiving N images (1102);
setting a counter i to an initial value, for example i=1 (1104);
defining a registration of image i to image i+1 (1106);
performing the registration of image i to image i+1 (1108);
combining image i with image i+1 (1110), to obtain a new image i+1; and
optionally performing additional method steps involved with management of the method, such as checking whether the counter i has reached an indication that all the images have been processed (1112), incrementing the counter and repeating the process with an additional image (1116), or ending the process (1114).

In FIG. 11A, a registration transformation is defined from each image (i) to a following image (i+1) (1106). The registration is executed (1108), and the obtained registered image is combined into the following image (1110). After the execution of 1116, a new image of the sequence is transformed to and combined with the combined image generated in the preceding execution of 1110.

It is noted that not all the N images have to be received before a registration of a first two images be defined and even performed. The images may be received in parallel to the defining registration and the combining.

Reference is now made to FIG. 11B, which is a simplified flowchart illustration of a method for combining N images into one according to an exemplary embodiment of the invention.

The method of FIG. 11B includes:
receiving N images (1122);
defining one of the images as a master image (1124);
defining N−1 registrations from each non-master image to the master image (1126);
performing the registrations (1128) by transforming the non-master images; and
combining the transformed and master images (1130).

It is noted that not all the N images have to be received before one of the received images is defined as a master image. A master image may be defined among a first few images received, and even a first image can be defined as a master image. Following the definition of a master image, registrations of non-master received images may be defined and even performed. The non-master images may be received in parallel to the defining registration and the combining.

In FIG. 11B, a master image is defined (1124), a registration transformation is defined from each of the N−1 non-master images to the master image (1126); the defined transformations are performed (1128) to obtain N−1 images registered with the master image, and at least some of the registered images and the master image are combined to a single combined image (1130).

In some embodiments, the registration transformations defined in 1126 are defined as a sequence of temporally coherent transformations. In such embodiments, it may be advantageous to know all the images in advance, which may facilitate defining of the sequence of transformations in parallel. For example, a single cost function may be defined, with N−1 penalty terms, each penalizing for spatial incoherence of a difference between two transformations registering two adjacent images to the master image.

In some embodiments, additional N−1 penalty terms may be used to penalize for spatial incoherence of each of the N−1 transformations from the non-master image to the master-image. In some embodiments, temporal coherence may be imposed on the sequence of transformations using other conditions, for example, as describe in the above-mentioned article titled "Registration of Multiple Temporally Related Point Sets Using a Novel Variant of the Coherent Point Drift Algorithm: Application to Coronary Tree Matching".

Reference is now made to FIG. 11C, which is a simplified flowchart illustration of a method of generating a combined image of a body part from a sequence of partially overlapping source images of the body part according to an exemplary embodiment of the invention.

The method of FIG. 11C describes generating a combined image of a body part from a sequence of partially overlapping source images of said body part, each of the partially overlapping source images showing the body part at one of a plurality of different times, the source images being ordered in the sequence according to said different times.

The method of FIG. 11C includes:

defining a temporally coherent sequence of transformations, for registering the partially overlapping source images in the sequence with each other (1140);

registering the source images to each other using the defined temporally coherent sequence of transformations, to obtain co-registered images (1142); and combining at least some of the co-registered images into a combined image (1144).

Reference is now made to FIG. 12, which is a simplified flowchart illustration of a method of generating an image from a stream of data according to an exemplary embodiment of the invention.

The method of FIG. 12 includes:

binning a stream of data into a sequence of bins (1202);

using the data in each bin to produce a corresponding image, to obtain a sequence images, each associated with corresponding bin (1204); and combining the images in the sequence obtained in 1204 into a single, combined, image (1206).

The method of FIG. 12, in some exemplary embodiments thereof, describes a method of generating a single combined image of a moving body part from a stream of measurements, which may be indicative of structure of partially overlapping portions of the body part. For example, the measurements may be taken from a probe (static or moving) that probes the body part as the body part moves, or from a moving probe, where the body part moves in respect to the probe, and may be static or moving with respect to an external reference system.

The method of FIG. 12, includes binning the stream of measurements to a sequence of bins (1202); using, the measurements in each bin to generate an image (1204) of a portion of the body part, so as to obtain a sequence of images that correspond to the sequence of bins; and generate a single combined image (1206) from the sequence of images.

In some embodiments, a sequence of measurements is binned (1202), that is, measurements made at different time windows are associated to different bins. The different time windows optionally overlap with each other. For example, the stream of measurements may include one minute of measurements, 100 measurements per second, each time window may be 1 second long, and each time window may start 50 msec (i.e., 5 measurements, in the present example) after the preceding window starts, so that about 90% of these two windows overlap. The non-overlapping times are the first 50 msec of the first window, and the last 50 msec of the second window. In some embodiments, an overlap ratio (O.R) may be defined as $$O.R = \frac{\text{overlap duration between the two windows}}{\text{total duration of the two windows}}$$

In some embodiments, the overlap ratio is between about 20% and about 90%, for example, 30%, 50%, 70%, etc.

In some embodiments, the binning is based on additional measurements, on ECG measurements. For example, when the body part is the heart, the ECG measurements may associate different time periods with different stages of a heartbeat, such as with a P wave, a QRS complex, and a T wave. In some embodiments, a finer partition of the heartbeat may be used, for example to a P segment, a PR segment, a QRS complex, an ST segment, and a T segment. Other ways of dividing a heartbeat to different stages are also possible. In some embodiments, measurements made during each such heartbeat stage are treated separately. For example, measurements made during the PR segment are optionally binned to a first sequence of bins, and steps 1204 and 1206 are practiced on this sequence of bins alone, to provide a first single image (say a PR single image). Then, measurements made during another heartbeat stage (e.g., ST segment) may be binned to a second sequence of bins, and steps 1204 and 1206 are optionally practiced in this second sequence of bins alone, to obtain a second single image (say an ST single image). Then, the two single images may be registered to each other and combined, e.g., using methods known as such in the field.

In some embodiments, in step 1204, measurements in each bin are used to generate an image of a portion of the body part. For example, the measurements may include voltage measurements at three different frequencies, and each such triplet of measurements may be presented as a point in a Cartesian coordinate system, so as to form a 3D image. In some embodiments, the number of frequencies may be different (e.g., 2 or 5), and the dimensionality of the image may be the same as the number of fields measured. In some embodiments, the measurements may be converted into a location-based image, for example, as taught in above-mentioned PCT Application WO 2018/130974. Using the method of PCT Application WO 2018/130974 or some other method, step 1204 produces a sequence of images, and each image in the sequence corresponds to a respective one of the bins formed in 1202. In some embodiments the bins are of overlapping time windows, and the images in the obtained sequence are of partially overlapping portions of the body part.

In some embodiments, in 1206 a single combined image is generated from the sequence of images generated in 1204, for example, by a method such as described with reference to FIGS. 10A, 10B, 11A, and 11B.

In some embodiments, the stream of measurements is first classified into sub-streams, each including measurements taken when the body part was in a different movement mode, and then the method described with reference to FIG. 12 is practiced on at least one of the sub-streams, optionally independently of the other sub-streams.

Examples of movement modes of a heart may include sinusoidal rhythm (which is a normal case) and chaotic rhythm (characteristic of atrial fibrillations). Different modes of heart rhythms may optionally be distinguished by analyzing ECG signals, and/or by analyzing electric signals from an intra-body probe.

In some embodiments, the binning, the generation of a sequence of images, and the generation of the single combined image are performed separately for every group (i.e., movement mode), to generate for each movement mode a different combined image. These combined images may then be registered to each other and further combined.

Reference is now made to FIG. 13, which is a simplified flowchart illustration of a method for producing a movie of a beating heart from a sequence of images of the beating heart according to an exemplary embodiment of the invention.

The method of FIG. 13 includes:

receiving a sequence of images (1302) of a beating heart;

generating a movie frame from each image in the sequence (1304); and ordering the movie frames according to the order of the images in the sequence (1306), thereby generating the movie.

In some embodiments the method of FIG. 13 describes a method of generating a movie of a beating heart from a sequence of partially overlapping images of the beating heart, captured during different time windows, which may be partially overlapping. The images in the sequence are ordered in the sequence according to the times at which they were captured. For example, according to a certain point in the time window, for example, according to the starting of the windows, according to the endings, or according to the middle of the windows.

The movie is made of a sequence of frames. To show the movie, the frames are displayed according to their order in the sequence of frames.

In some embodiments each frame is based on a sequence of images, and in some embodiments, it is the same sequence of images that is a basis for all the frames. In some embodiments, each frame is generated from the sequence of images according to the method described in FIG. 11B, optionally, using for each frame a different one of the images as a master-image.

In some embodiments the order of each frame in the sequence of frames is optionally the same as the order of the corresponding image that is used as a master-image. For example, the first frame in the movie may be a single combined image generated with the first image as the master-image, the second frame—based on the second image as the master-image, etc.

In some embodiments, the movie may be made for displaying as an infinite loop, so that the first frame is displayed after each display of the last frame. At least in these cases, there may be no significance as to which frame is the first in the sequence, but the order of the frames may make a difference. For example, reversing the order of the frames (or the order of displaying the frames) may result in showing the movie backwards in time.

In some embodiments, the method of FIG. 13 includes two steps: generating a single frame for each image in the sequence of images; and ordering the single frames according to the ordering of the images in the sequence of images.

EXAMPLE(S)

Reference is now made to the following examples, which together with the above descriptions illustrate some embodiments of the invention in a non-limiting fashion.

Reference is now made to FIG. 9, which is an image of a heart produced following gate projection of several data bins into one common reference data bin according to some embodiments of the invention.

FIG. 9 is a first image 701 of a sequence of frames taken of a left atrium during a systole.

The movie (also referred herein as a cine) of which image 701 is a first frame, was made by the method described in FIG. 13, using the method described by FIG. 11B for generating each frame, with each frame in the sequence making the movie being generated with a corresponding image as a master-image.

Data for producing the cine sequence of image frames, for example Frame(0), Frame(1), Frame(2), and so on, was captured at time points referenced, for example, as $T_0$, $T_1$, $T_2$ and so on.

The data was binned into data bins 0, 1, 2 and so on associated with the time points $T_0$, $T_1$, $T_2$.

Each one of the image frames Frame(0), Frame(1), Frame(2) was produced by gate-projecting data from all the data bins into a data bin associated with the time point T associated with the image frame, that is: Frame(0) was produced from data points for $T_0$ and gate-projected data points from $T_1$ to $T_0$ and gate-projected data points from $T_2$ to $T_0$, and so on; Frame(1) was produced from data points for $T_1$ and gate-projected data points from $T_0$ to $T_1$ and gate-projected data points from $T_2$ to $T_1$ and so on; and Frame(2) was produced from data points for $T_2$ and gate-projected data points from $T_0$ to $T_2$ and gate-projected data points from $T_1$ to $T_2$ and so on.

It is expected that during the life of a patent maturing from this application many relevant intra-body probes will be developed and the scope of the term intra-body probe is intended to include all such new technologies a priori.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer-implemented method of generating a combined image of a body part from a sequence of partially overlapping source images of said body part, each of the partially overlapping source images showing the body part at one of a plurality of different times, the source images being ordered in the sequence according to said different times, the method comprising:
   defining a temporally coherent sequence of transformations, for registering the partially overlapping source images in the sequence with each other,
   registering the source images to each other using the defined temporally coherent sequence of transformations, to obtain co-registered images; and
   combining at least some of the co-registered images into a combined image;
   wherein the defining comprises searching for a sequence of transformations using minimization of a cost function that penalizes for temporal incoherence of the sequence of transformations.

2. The method of claim 1 wherein the body part undergoes a periodic change, and the source images are ordered in the sequence according to their phase in a cycle of the periodic change; and wherein the sequence of transformations includes adjustments to account for the periodic change.

3. The method of claim 1, comprising:
   setting one of the source images to be a master image, and the rest of the source images to be non-master images;
   defining for the non-master images, a temporally coherent sequence of transformations, each transformation registering a respective non-master image to the master image,
   transforming each non-master image, using the transformation defined for said non-master image, to obtain a corresponding transformed image; and
   combining at least some of the transformed images and the master image into a single combined image.

4. The method of claim 1, wherein the searching comprises testing sequences of transformations for satisfying the condition that a difference between any two consecutive transformations defined between consecutive source images is spatially coherent.

5. The method of claim 1, wherein searching comprises testing sequences of transformations for satisfying the condition that each transformation of the temporally coherent sequence of transformations is spatially coherent.

6. The method of claim 1, wherein the cost function further penalizes for spatial incoherence of a transformation in the sequence.

7. The method of claim 1, wherein the cost function further penalizes for spatial incoherence of a difference between sequential transformations in the sequence.

8. The method of claim 1, wherein each one of the source images in the sequence shows the body part as imaged during a different time window, and time windows of at least some of the source images in the sequence partially overlap.

9. The method of claim 8, wherein time windows of each two consecutive source images in the sequence partially overlap.

10. The method of claim 1, wherein each one of the source images comprises points representing values of electrical measurements, and the method further comprises transforming the combined image into a transformed combined image comprising points representing locations in space.

11. The method of claim 1, wherein each one of the source images in the sequence comprises points representing locations in space.

12. The method of claim 1, wherein:
   each one of the source images is a point cloud; and
   the combining the co-registered images produces a combined point cloud; and
   further comprising reconstructing the combined image from the combined point cloud.

13. The method of claim 12 wherein the reconstructing the combined image from the combined point cloud comprises using a ball pivoting algorithm.

14. The method of claim 1, wherein a specified location is marked on a plurality of the source images, and the transformations are defined to transform the location marked on said plurality of the source images to a same location.

15. The method of claim 1, further comprising:
   bringing an intra-body probe into the body part or to a vicinity thereof;
   receiving measurements from the intra-body probe; and
   generating the sequence of partially overlapping source images based on the measurements received from the intra-body probe.

16. A non-transient computer readable medium containing program instructions for causing a computer to perform the method of claim 1.

17. The method of claim 1, wherein the source images represent the body part as different respective sparse data matrices representing different respective sets of body part locations.

18. The method of claim 17, wherein at least some of the different sparse data matrices represent the body part locations at different respective times.

19. The method of claim 17, wherein at least some of the different sparse data matrices represent the body part locations at different respective phases of a cyclical body motion.

20. The method of claim 17, wherein at least some of the different sparse data matrices represent the body part locations at different respective times while the body part undergoes different respective modes of a cyclical body motion.

21. The method of claim 1, wherein the penalized temporal incoherence comprises a trend established in earlier transformations of the sequence that does not continue in a following transformation.

22. A system comprising a processor and memory, the memory recording instructions which instruct the processor to:
- define a temporally coherent sequence of transformations for registering the partially overlapping source images in the sequence with each other, using minimization of a cost function that penalizes for temporal incoherence;
- register the source images to each other using the defined temporally coherent sequence of transformations, to obtain co-registered images; and
- combine at least some of the co-registered images into a combined image.

23. The system of claim 22, wherein the source images represent the body part as different respective sparse data matrices representing different sets of body part locations.

* * * * *